US011648184B2

(12) United States Patent
Hara et al.

(10) Patent No.: US 11,648,184 B2
(45) Date of Patent: May 16, 2023

(54) DENTAL COMPOSITION CONTAINING ION SUSTAINED-RELEASE GLASS

(71) Applicant: SHOFU INC., Kyoto (JP)

(72) Inventors: Daisuke Hara, Kyoto (JP); Yuji Sadakane, Kyoto (JP); Katsura Ishikawa, Kyoto (JP); Hidefumi Fujimura, Kyoto (JP); Shuji Sakamoto, Kyoto (JP); Akihiro Nagafuji, Kyoto (JP); Toshiyuki Nakatsuka, Kyoto (JP)

(73) Assignee: SHOFU INC., Kyoto (JP)

(*) Notice: Subject to any disclaimer, the term of this patent is extended or adjusted under 35 U.S.C. 154(b) by 0 days.

(21) Appl. No.: 14/593,103

(22) Filed: Jan. 9, 2015

(65) Prior Publication Data
US 2015/0342838 A1 Dec. 3, 2015

(30) Foreign Application Priority Data

| May 30, 2014 | (JP) | JP2014-113577 |
| May 30, 2014 | (JP) | JP2014-113578 |
| May 30, 2014 | (JP) | JP2014-113579 |
| May 30, 2014 | (JP) | JP2014-113580 |
| May 30, 2014 | (JP) | JP2014-113581 |
| May 30, 2014 | (JP) | JP2014-113582 |
| May 30, 2014 | (JP) | JP2014-113583 |
| May 30, 2014 | (JP) | JP2014-113584 |

(51) Int. Cl.
A61K 6/00 (2020.01)
A61Q 11/00 (2006.01)
A61K 8/19 (2006.01)
A61K 8/21 (2006.01)
A61K 8/25 (2006.01)
A61K 8/26 (2006.01)
A61K 6/70 (2020.01)
A61K 8/81 (2006.01)
A61K 6/20 (2020.01)
A61K 6/77 (2020.01)

(52) U.S. Cl.
CPC .................. A61K 6/70 (2020.01); A61K 6/20 (2020.01); A61K 6/77 (2020.01); A61K 8/19 (2013.01); A61K 8/21 (2013.01); A61K 8/25 (2013.01); A61K 8/26 (2013.01); A61K 8/8152 (2013.01); A61Q 11/00 (2013.01); A61K 2800/56 (2013.01); A61K 2800/81 (2013.01); A61K 2800/882 (2013.01); A61K 2800/95 (2013.01)

(58) Field of Classification Search
CPC ... A61K 6/77; A61K 6/20; A61K 6/70; A61K 8/19; A61K 8/21; A61K 8/25; A61K 8/26; A61K 8/8152; A61K 2800/56; A61K 2800/882; A61K 2800/95; A61K 2800/81; A61Q 11/00
See application file for complete search history.

(56) References Cited

U.S. PATENT DOCUMENTS

| 4,044,762 | A | | 8/1977 | Jacobs | |
| 4,748,198 | A | | 5/1988 | Takahashi et al. | |
| 4,814,362 | A | * | 3/1989 | Billington | A61K 6/0835 523/117 |
| 5,147,202 | A | | 9/1992 | Masuhara et al. | |
| 5,154,762 | A | * | 10/1992 | Mitra | C04B 28/28 106/35 |
| 5,839,900 | A | * | 11/1998 | Billet | A61C 5/08 433/202.1 |
| 6,365,132 | B1 | | 4/2002 | Litkowski et al. | |
| 6,583,197 | B1 | | 6/2003 | Wada et al. | |
| 7,683,103 | B2 | | 3/2010 | Sawada et al. | |
| 8,129,444 | B2 | * | 3/2012 | Hecht | C09J 4/00 106/35 |
| 2003/0050359 | A1 | | 3/2003 | Kimura et al. | |
| 2004/0071638 | A1 | | 4/2004 | Simonton et al. | |
| 2009/0022672 | A1 | | 1/2009 | Reynolds | |
| 2009/0068123 | A1 | | 3/2009 | Takei et al. | |
| 2009/0208428 | A1 | | 8/2009 | Hill et al. | |
| 2010/0086497 | A1 | | 4/2010 | Burwell et al. | |
| 2012/0028223 | A1 | * | 2/2012 | Simonton | A61C 5/00 433/228.1 |

FOREIGN PATENT DOCUMENTS

| EP | 0 997 132 A1 * | 5/2000 |
| JP | S62-277953 A | 12/1987 |
| JP | H02-142718 A | 5/1990 |

(Continued)

OTHER PUBLICATIONS

Hughes et al.: Compatibility studies on polyacrylate and polymethacrylate systems, Applied polymer Science, May 1961.*
Aug. 8, 2014 Office Action issued in JP Patent Application No. 2014-113578.
Jul. 3, 2014 Office Action issued in JP Patent Application No. 2014-113579.

(Continued)

Primary Examiner — Hong Yu
(74) Attorney, Agent, or Firm — Wenderoth, Lind & Ponack, L.L.P.

(57) ABSTRACT

To provide a dental composition wherein the acid buffering capacity can be attained and the acid resistance of the tooth substance can be improved while maintaining very high foul breath inhibition capacity. A dental composition including: ion sustained-release glass; and a carrier for supporting the ion sustained-release glass, wherein the ion sustained-release glass is fluoroaluminoborosilicate glass having a composition range of: 15% to 35% by mass $SiO_2$; 15% to 30% by mass $Al_2O_3$; 5% to 20% by mass $B_2O_3$; 20% to 45% by mass SrO; 5% to 15% by mass F; and 0% to 10% by mass $Na_2O$.

17 Claims, No Drawings

(56) References Cited

FOREIGN PATENT DOCUMENTS

| | | |
|---|---|---|
| JP | H04-60562 A | 2/1992 |
| JP | H07-206470 A | 8/1995 |
| JP | H08-291017 A | 11/1996 |
| JP | H09-315922 A | 12/1997 |
| JP | H10-182393 A | 7/1998 |
| JP | H10-279414 A | 10/1998 |
| JP | H10-330234 A | 12/1998 |
| JP | 2000-312689 A | 11/2000 |
| JP | 2001-288025 A | 10/2001 |
| JP | 2001-516709 A | 10/2001 |
| JP | 2002-114620 A | 4/2002 |
| JP | 2002-167318 A | 6/2002 |
| JP | 3418056 B2 | 6/2003 |
| JP | 3452613 B2 | 9/2003 |
| JP | 2004-168747 A | 6/2004 |
| JP | 2004-527539 A | 9/2004 |
| JP | 2006-016396 A | 1/2006 |
| JP | 2006-225281 A | 8/2006 |
| JP | 2007-314505 A | 12/2007 |
| JP | 2007-326808 A | 12/2007 |
| JP | 2008-127391 A | 6/2008 |
| JP | 4231949 B2 | 3/2009 |
| JP | 2009-525988 A | 7/2009 |
| JP | 2009-539755 A | 11/2009 |
| JP | 2010-047488 A | 3/2010 |
| JP | 2010-215538 A | 9/2010 |
| JP | 2010-229072 A | 10/2010 |
| JP | 4562819 B2 | 10/2010 |
| JP | 4673310 B2 | 4/2011 |
| JP | 2011-098920 A | 5/2011 |
| JP | 2011-132189 A | 7/2011 |
| JP | 2011-229839 A | 11/2011 |
| JP | 2012-505192 A | 3/2012 |
| JP | 2013-163656 A | 8/2013 |
| JP | 5443688 B2 | 3/2014 |
| WO | 02/085319 A1 | 10/2002 |
| WO | 2010/061932 A1 | 6/2010 |
| WO | 2011/016395 A1 | 2/2011 |

OTHER PUBLICATIONS

Aug. 8, 2014 Office Action issued in JP Patent Application No. 2014-113580.
Jul. 3, 2014 Office Action issued in JP Patent Application No. 2014-113581.
Jul. 3, 2014 Office Action issued in JP Patent Application No. 2014-113582.
Jul. 28, 2014 Office Action issued in JP Patent Application No. 2014-113583.
Jul. 28, 2014 Office Action issued in JP Patent Application No. 2014-113584.
Kazuhiro, W. et al. "Anti-plaque characteristics of MMA Self-curing Resin Containing S-PRG Filler." The Journal of Gifu Dental Society, 2013, vol. 39, No. 3. pp. 127-139.
Oct. 6, 2015 Extended Search Report issued in European Patent Application No. 15150487.5.
Oct. 12, 2015 Extended Search Report issued in European Patent Application No. 15150317.4.

* cited by examiner

DENTAL COMPOSITION CONTAINING ION SUSTAINED-RELEASE GLASS

TECHNICAL FIELD

The present invention relates to a dental composition containing ion sustained-release glass that continuously sustained-releases ions.

BACKGROUND

In the case where "decalcification" in which the calcium ion and the phosphate ion flow out from the tooth substance (hydroxyapatite) and "calcification" in which the calcium ion and the phosphate ion are taken into the tooth substance are in equilibrium in the oral cavity, the tooth substance is kept healthy. When the oral cavity becomes more acidic due to drinking and eating, the adhesion of plaque (such as food residue and peeling mucosa), etc., the equilibrium relation between decalcification and calcification is disrupted, and decalcification becomes more dominant. As a result, the calcium ion and the phosphate ion excessively flow out from the tooth substance, leading to dental caries. Saliva plays a very important role in this equilibrium reaction. Since saliva has the calcium ion and the phosphate ion, saliva functions in the oral cavity so as to make calcification dominant. Moreover, bicarbonate, a phosphate, and a protein which are the components of saliva have an acid neutralizing capacity, so that saliva is capable of buffering the acidified oral cavity to neutral. Saliva thus protects the tooth substance from decalcification, by both of the effect of supplying the calcium ion and the phosphate ion and the effect of acid buffering capacity. However, the ion supplying capacity and the acid buffering capacity are limited, which raises the need for a material having a tooth substance strengthening or acid buffering capacity.

It is widely known that the active application of fluoride to the tooth substance is effective for the prevention of dental caries. The fluoride ion forms fluoroapatite when taken into the tooth substance, which contributes to improved acid resistance of the tooth substance and prevention of dental caries. Hence, materials such as fluoride salt-containing dentifrices or fluorine-applying agents are widely used for the prevention of dental caries.

It is also known that saliva has a foul breath inhibition capacity. Unpleasant breath is fundamentally caused by methylmercaptan, hydrogen sulfide, etc. generated as a result of bacterial degradation of plaque. Saliva includes antibacterial agents such as lysozyme, lactoperoxidase, lactoferrin, and secretory immunoglobulin A, and can suppress bacterial growth. If the dryness in the oral cavity continues due to xerostomia (dry mouth), physiological factors (temporary decrease in saliva secretion during sleep, etc.), medication side effects, and the like, the bacterial growth suppression effect of saliva cannot be attained, and bacteria in the oral cavity grow and foul breath becomes evident. Saliva not only protects the tooth substance in decalcification and calcification, etc. but also has the bacterial growth suppression capacity, and so is essential for keeping the oral cavity environment healthy.

Patent Literature (PTL) 1 discloses an edible film for oral hygiene for suppressing bacterial growth by promoting saliva secretion. As a base material for promoting saliva secretion, an edible film for oral hygiene containing an organic acid and in particular citric acid, tartaric acid, fumaric acid, malic acid, succinic acid, or lactic acid is shown as an example. When the edible film containing the above-mentioned organic acid is attached to an elderly person with an insufficient amount of saliva or a patient affected by dry mouth, saliva secretion is promoted and the bacterial growth suppression effect is expected. In the case of normal saliva secretion, however, a significant effect cannot be expected.

PTL 2 discloses an oral cavity care product that contributes to tooth substance recalcification and improved acid resistance. A solid oral cavity composition contains a calcium-containing component, a fluorine-containing component, and a phosphate. The calcium ion sustained-released from the calcium-containing component, the fluoride ion sustained-released from the fluorine-containing component, and/or the phosphate ion sustained-released from the phosphate are expected to recalcify the tooth substance and enhance the acid resistance.

CITATION LIST

Patent Literature

PTL 1: JP 2007-326808 A
PTL 2: JP 2002-167318 A

The conventional technique of promoting saliva secretion or sustained-releasing the calcium ion and the phosphate ion in the oral cavity is useful in promoting tooth substance recalcification, but the recalcified tooth substance is merely reformed into the original hydroxyapatite, and improved acid resistance cannot be expected. The oral cavity care composition for sustained-releasing the fluoride ion is excellent in that the fluoride ion sustained-released from the composition is taken into the tooth substance and form fluoroapatite to thereby improve the acid resistance, but has the following problem. Since the supply source of the calcium ion and the supply source of the fluoride ion are present in the oral cavity care composition, as a result of water being taken into the oral cavity care composition, hardly-soluble salt of calcium fluoride is formed immediately after the calcium ion and the fluoride ion melt. This results in an insufficient effect of improving the acid resistance.

SUMMARY

As a result of conducting intensive study to overcome the problems stated above, the inventors have found out that, by including ion sustained-release glass (a) having a specific composition and a carrier (b) for supporting the ion sustained-release glass (a) in a dental composition, the acid buffering capacity can be attained and the acid resistance of the tooth substance can be improved while maintaining very high foul breath inhibition capacity. The inventors have then completed the present invention. The inventors provide the following invention.

In detail, a dental composition includes: ion sustained-release glass (a); and a carrier (b) for supporting the ion sustained-release glass (a), wherein the ion sustained-release glass (a) is fluoroaluminoborosilicate glass having a composition range of: 15% to 35% by mass $SiO_2$; 15% to 30% by mass $Al_2O_3$; 5% to 20% by mass $B_2O_3$; 20% to 45% by mass SrO; 5% to 15% by mass F; and 0% to 10% by mass $Na_2O$.

Preferably, the ion sustained-release glass (a) is surface-coated with a silane compound (c) and then surface-treated with an acid polymer (d).

Preferably, the ion sustained-release glass (a) sustained-releases a fluoride ion, and further sustained-releases at least one type of ion from among a strontium ion, an aluminum ion, and a borate ion.

The dental composition according to the present invention in which the carrier (b) is a film forming material (e) is suitable for use as a neutralization promoting ion sustained-release dental film that has a thickness of 15 μm to 500 μm.

The dental composition according to the present invention in which the carrier (b) is a film component (f) and an organic solvent (g) is suitable for use as a dental varnish composition.

The dental composition according to the present invention in which the carrier (b) is a gum base (h) is suitable for use as a dental gum composition.

The dental composition according to the present invention in which the carrier (b) is water (i) is suitable for use as an oral cavity care composition.

The dental composition according to the present invention in which the carrier (b) is a thermoplastic resin (j) is suitable for use as a thermoplastic sheet composition for mouthguard or splint production.

The dental composition according to the present invention in which the carrier (b) is a noncrosslinked (meth)acrylate polymer (k) is suitable for use as a two-component mixture ion sustained-release denture base-related material composition composed of a powder material and a liquid material. In this case, the two-component mixture ion sustained-release denture base-related material composition includes: a powder material including the dental composition according to the present invention in which the carrier (b) is a noncrosslinked (meth)acrylate polymer (k); and a liquid material including a monofunctional (meth)acrylate polymerizable monomer (l), wherein at least one of the powder material and the liquid material includes a polymerization initiator (m).

The dental composition according to the present invention in which the carrier (b) is a noncrosslinked (meth)acrylate polymer (k) is suitable for use as a two-component mixture ion sustained-release mucosa modifier composition composed of a powder material and a liquid material. In this case, the two-component mixture ion sustained-release mucosa modifier composition includes: a powder material including the dental composition according to the present invention in which the carrier (b) is a noncrosslinked (meth) acrylate polymer (k); and a liquid material including a plasticizer (n) and an organic solvent (g).

The dental composition according to the present invention is suitable for use as a dental resin temporary sealing material composition that is polymerizable, the dental resin temporary sealing material composition including: a noncrosslinked (meth)acrylate polymer (k); a monofunctional (meth)acrylate polymerizable monomer (l); a hydrophilic polymerizable monomer (p); a polymerization initiator (q); and a plasticizer (n).

It is expected that the ion sustained-released from the ion sustained-release glass (a) used in the present invention improves the acid resistance of the tooth substance, and the acid neutralizing action in the oral cavity and the sustained release of the fluoride ion improve the acid resistance of the tooth substance.

The ion sustained-released from the ion sustained-release glass (a) is taken into the tooth substance and forms various types of apatite, as a result of which the acid resistance is improved. The inventors have found out that, in the case where such an ion that has an acid neutralizing capacity of neutralizing the surrounding oral cavity environment when the environment becomes more acidic is sustained-released, both the improvement of the acid resistance of the tooth substance and the neutralization of the oral cavity environment can be achieved. The inventors have then completed the present invention. Moreover, since the ion is sustained-released from the glass skeleton, there is no counter ion unlike when the ion flows out from a salt compound. The ion can be stably sustained-released because the ion sustained release is not impaired by salt formation.

Another action of the present invention is that the oral cavity environment can be kept in a good state as a result of the sustained release of the ion exhibiting bactericidal action from the ion sustained-release glass. The ion sustained-released from the ion sustained-release glass and exhibiting bactericidal effect is expected to suppress the growth of bacteria that generate methylmercaptan or hydrogen sulfide which causes foul breath. In other words, since the growth of bacteria in the oral cavity is suppressed, foul breath is expected to be prevented.

DETAILED DESCRIPTION

[Dental Composition]

A dental composition according to the present invention includes ion sustained-release glass (a) and a carrier (b) for supporting the ion sustained-release glass (a), wherein an ion resulting from the glass composition is continuously sustained-released from the ion sustained-release glass (a).

—Ion Sustained-Release Glass (a)

The ion sustained-release glass (a) used in the present invention is a glass including at least one type of glass skeleton forming element for forming a glass skeleton and at least one type of glass modifying element for modifying the glass skeleton, and is fluoroaluminoborosilicate glass whose composition range is as follows: $SiO_2$ 15% to 35% by mass, $Al_2O_3$ 15% to 30% by mass, $B_2O_3$ 5% to 20% by mass, SrO 20% to 45% by mass, F 5% to 15% by mass, and $Na_2O$ 0% to 10% by mass. In the present invention, an element that can be either a glass skeleton forming element or a glass modifying element depending on the glass composition, namely, a glass amphoteric element, is included in the category of glass skeleton forming elements. Another specific example of the glass skeleton forming element included in the ion sustained-release glass (a) is phosphorus. Specific examples of the glass modifying element include: halogen elements such as fluorine, bromine, and iodine; alkali metal elements such as sodium and lithium; and alkaline earth metal elements such as calcium and strontium, which may be used singly or in combination. It is preferable to include fluorine, sodium, or strontium as the glass modifying element. A specific example is fluoroaluminoborosilicate glass including strontium or sodium. This glass composition can be checked by instrumental analysis such as elemental analysis, Raman spectrum analysis, or fluorescence X-ray analysis, where it is only necessary that the actual measurement by any of the analysis methods meets the composition ranges.

The method of manufacturing the glass is not particularly limited, and manufacturing methods such as a melting method and a sol-gel method are applicable. Of these, the melting method using a melting furnace is preferable for ease of glass composition design including raw material selection.

The ion sustained-release glass (a) used in the present invention has an amorphous structure, but may partially include a crystalline structure or be a mixture of glass having an amorphous structure and glass having a crystalline structure. Whether or not the glass structure is amorphous can be determined using an analyzer such as an X-ray diffraction analyzer or a transmission electron microscope. The ion sustained-release glass (a) used in the present invention preferably has an amorphous structure which is a homogeneous structure, as various ions are sustained-released according to the equilibrium relationship with the ion concentration in an external environment.

The sustained release of various ions from the ion sustained-release glass (a) used in the present invention is influenced by the particle diameter of the glass, and accordingly the particle diameter needs to be controlled by a method such as wet and/or dry grinding, classification, or screening. The particle diameter (50%) of the ion sustained-release glass used in the present invention is not particularly limited, so long as it is in the range of 0.01 μm to 100 μm. A preferable range is 0.01 μm to 50 μm, and a more preferable range is 0.1 μm to 5 μm. The shape of the glass is not particularly limited, and may be any shape such as spherical, platy, crushed, and scaly. A preferable shape is spherical or crushed. The ion sustained-release glass (a) is preferably an ion sustained-release filler formed by grinding glass.

To enhance the ion sustained releasability from the ion sustained-release glass (a), it is preferable to surface-treat the glass surface for functionalization to increase the ion sustained releasability. Specific examples of the surface treatment material used in the surface treatment include a surface active agent, a fatty acid, an organic acid, an inorganic acid, a monomer, a polymer, each type of coupling material, a silane compound, a metal alkoxide compound, and its partial condensate. Preferably, an acid polymer (d) and a silane compound (c) are used as the surface treatment material.

An example of the method of surface-treating the ion sustained-release glass (a) using the acid polymer (d) and the silane compound (c) as the surface treatment material, in detail, the method of coating the surface of the ion sustained-release glass with a silane compound and then surface-treating the ion sustained-release glass using an acid polymer, is described below.

In an aqueous dispersion containing the ion sustained-release glass (a) finely ground into a desired average particle diameter by grinding or the like, the silane compound (c) expressed by general formula (I) is mixed.

[Chemical Formula 1]

(1)

(in the formula, Z is RO—, X is halogen, Y is OH—, R is an organic group whose carbon number is less than or equal to 8, and n, m, and L are each an integer from 0 to 4 where n+m+L=4). The mixture is hydrolyzed or partially hydrolyzed in the system to generate a silanol compound, which is then condensed and forms a coating on the surface of the ion sustained-release glass (a).

In the above-mentioned polysiloxane treatment method, the hydrolysis and condensation of the silane compound and the polysiloxane treatment on the glass surface are simultaneously performed in the same system. Alternatively, a polysiloxane coating can also be formed efficiently on the surface of the ion sustained-release glass (a) by a surface treatment method of performing the hydrolysis and condensation of the silane compound in another system to generate a low condensate silane compound (oligomer) and mixing it in an aqueous dispersion containing ion sustained-release glass (a). A more preferable method is polysiloxane treatment in which mixture is performed using a commercially-available low condensate silane compound (oligomer) without a low condensate generation process. This method is preferable for the following reason. In the case where a silane compound monomer is used, condensation occurs three-dimensionally and self-condensation is dominant due to the presence of a large amount of water in the polysiloxane treatment process, making it impossible to form a uniform polysiloxane coating on the glass surface.

In the case where a low condensate silane compound (oligomer) is used, on the other hand, a polysiloxane coating can be uniformly formed on the glass surface for each unit that has a polysiloxane main chain of a certain length. The shape of the low condensate silane compound (oligomer) is not particularly limited, though a straight chain is more preferable than a three-dimensional body. The degree of polymerization is preferably in the range of 2 to 20 and more preferably in the range of 2 to 6, given that a greater length causes lower condensation reactivity and results in poor polysiloxane coating formation on the surface of the ion sustained-release glass (a). The molecular weight in this case is in the range of 500 to 600.

The polysiloxane treatment in the aqueous dispersion is performed in a relatively low-speed stirring state. The temperature is in the range of 20° C. to 100° C., and preferably in the range of 20° C. to 50° C. The stirring time is typically in the range of several minutes to several tens of hours, and preferably in the range of 30 minutes to 4 hours. No special method is required for stirring, which can be conducted with a facility typically used in the industry. For example, a stirrer capable of stirring slurry forms, such as a universal mixing stirrer or a planetary mixer, may be used. The stirring temperature may be any temperature at which an aqueous medium does not volatilize, i.e. any temperature less than the boiling point of the aqueous medium. The stirring time needs to be adjusted because the speed of gelation by condensation is influenced by the type or addition amount of the silane compound or low condensate silane compound, the type or particle diameter of the glass and its proportion in the aqueous dispersion, and the type of the aqueous medium or its proportion in the aqueous dispersion. Besides, stirring needs to be performed until the gel is formed. Since excessively fast stirring breaks the gel structure and hinders uniform coating formation, the stirring speed needs to be low.

The aqueous medium is composed of water and alcohol. The addition of alcohol has a significantly advantageous effect of reducing the aggregability of the ion sustained-release glass during drying and improving its cracking property. The alcohol is preferably an alcohol whose carbon number is 2 to 10. In the case where an alcohol whose carbon number exceeds 10 is added, a long time is required to dry and remove the solvent due to high boiling point. Specific alcohols include ethyl alcohol, n-propyl alcohol, isopropyl alcohol, n-butyl alcohol, t-butyl alcohol, isobutyl alcohol, n-pentyl alcohol, isoamyl alcohol, n-hexyl alcohol, n-heptyl alcohol, n-octyl alcohol, and n-dodecyl alcohol. An alcohol whose carbon number is 2 to 4, such as ethyl alcohol, n-propyl alcohol, or isopropyl alcohol, is preferably used. The addition amount of the alcohol is 5 to 100 parts by weight and preferably 5 to 20 parts by weight, with respect to water. The addition amount exceeding 100 parts by weight causes problems such as complicating the drying step. The glass content is in the range of 25 to 100 parts by weight and preferably in the range of 30 to 75 parts by weight, with respect to the aqueous medium. In the case where the content exceeds 100 parts by weight, the speed of gelation by condensation is high, and a uniform polysiloxane coating layer is difficult to be formed. In the case where the content is less than 25 parts by weight, the glass settles out in the stirring state or phase separation occurs in the aqueous medium. The addition amount of the silane compound depends on the particle diameter of the glass. The addition amount of the silane compound is in the range of 0.1 to 10 parts by weight and preferably in the range of 0.1 to 4 parts by weight in terms of $SiO_2$, with respect to the glass. In the case where the addition amount is less than 0.1 parts by weight, an aggregate results as crushing into primary particles is impossible, with there being no polysiloxane coating layer formation effect. In the case where the addition amount exceeds 10 parts by weight, the solidified matter after drying is too hard to be crushed.

The system which is in a "gel" state is dried, has the aqueous medium removed, and solidified. The drying is made up of two steps that are maturation and firing. Maturation is intended to grow the gel structure and remove the aqueous medium, and firing is intended to strengthen the gel structure. Maturation needs to be performed in a static state to keep the gel structure from distortion and remove the aqueous medium, and is preferably performed in a facility such as a box-type hot air dryer. The maturing temperature is in the range of 20° C. to 100° C., and preferably in the range of 40° C. to 80° C. In the case where the temperature is below this range, the aqueous medium cannot be removed sufficiently. In the case where the temperature is above this range, rapid volatilization occurs, and the gel structure may become defective or peel away from the glass surface. The maturing time depends on the capacity of the drier or the like, and may be any time sufficient to remove the aqueous medium.

The firing step includes temperature rise and mooring. Temperature rise is preferably performed gradually over a long time until a target temperature is reached. A rapid temperature change causes poor heat conduction of the gel dispersion, as a result of which a crack may occur in the gel structure. Mooring is firing at a constant temperature. The firing temperature is in the range of 100° C. to 350° C., and preferably in the range of 100° C. to 200° C.

As described above, the aqueous medium is removed from the gel by drying, and a contracted solidified matter is obtained. The solidified matter is in an ion sustained-release glass aggregate state. The solidified matter, however, is not simply an aggregate of ion sustained-release glass, but polysiloxane formed by condensation is present on the boundary surfaces of individual fine particles. Accordingly, when the solidified matter is crushed into a size equivalent to the ion sustained-release glass before the polysiloxane treatment in the next step, the ion sustained-release glass whose surface is coated with polysiloxane is obtained. Here, "crushing into a size equivalent to the ion sustained-release glass before the polysiloxane treatment" means crushing into primary particles of ion sustained-release glass coated with polysiloxane. The difference from the original ion sustained-release glass lies in that the individual fine particles are coated with polysiloxane. The inclusion of a secondary aggregate is, however, allowed to an extent that causes no problem. The solidified matter can be easily crushed by applying a shearing force or an impact force. For example, a Henschel mixer, a cross rotary mixer, a super mixer, or the like may be used for crushing.

—Carrier (b)

The carrier (b) may be any carrier capable of supporting the ion sustained-release glass (a) and being retained in the oral cavity without adhering to oral cavity tissues, and is different from a material such as a composite in that it does not permanently adhere to oral cavity tissues. Examples of the carrier (b) include a film forming material (e), a combination of a film component (f) and an organic solvent (g), a gum base (h), water (i), a thermoplastic resin (j), and a noncrosslinked (meth)acrylate polymer (k), though the carrier (b) is not limited to such.

—Silane Compound (c)

Examples of the silane compound (c) expressed by general formula (I) include tetramethoxysilane, tetraethoxysilane, tetrapropoxysilane, tetraallyloxysilane, tetrabutoxysilane, tetrakis(2-ethylhexyloxy)silane, trimethoxychlorosilane, triethoxychlorosilane, triisopropoxychlorosilane, trimethoxyhydroxysilane, diethoxydichlorosilane, tetraphenoxysilane, tetrachlorosilane, and silicon hydroxide (silicon oxide hydrate). Tetramethoxysilane and tetraethoxysilane are particularly preferable. An aggregate represented by the silane compound expressed by general formula (I) is more preferable.

A low condensate of the silane compound expressed by general formula (I) is more preferable. An example of this is a low condensate silane compound obtained by partially hydrolyzing tetramethoxysilane and tetraethoxysilane and condensing them. These compounds may be used singly or in combination.

An organo silane compound may be added as part of the silane compound expressed by general formula (I) during polysiloxane treatment. Specific examples of the organosiloxane compound include methyltrimethoxysilane, ethyltrimethoxysilane, methoxytripropylsilane, propyltriethoxysilane, hexyltrimethoxysilane, vinyltrimethoxysilane, vinyltriethoxysilane, vinyltri(β-methoxyethoxy)silane, γ-methacryloxypropyltrimethoxysilane, γ-glycidoxypropylmethoxysilane, γ-mercaptopropyltrimethoxysilane, γ-aminopropyltriethoxysilane, 3-aminopropyltriethoxysilane, methyltrichlorosilane, and phenyltrichlorosilane. Methyltrimethoxysilane, ethyltrimethoxysilane, vinyltriethoxysilane, and phenyltrichlorosilane are particularly preferable. These compounds may be used singly or in combination. In such a compound, however, an organic group is present in the polysiloxane layer, and so there is a possibility that distortion occurs during polysiloxane layer formation and a problem with mechanical strength results. Therefore, the addition of the compound needs to be limited to a small amount. Moreover, an alkoxide compound, halide, hydrated oxide, nitrate, or carbonate of another metal may be added as part of the silane compound expressed by general formula (I) during polysiloxane treatment.

The ion sustained-release glass (a) coated with polysiloxane in the above-mentioned step undergoes an acid polymer treatment of reacting with the acid polymer (d), as a result of which the most preferable surface-treated ion sustained-release glass according to the present invention is obtained. The acid polymer treatment may employ a facility typically used in the industry, so long as it is a dry flow stirrer. Examples of such a facility include a Henschel mixer, a super mixer, and a high speed mixer. The reaction of the ion sustained-release glass, on which the polysiloxane coating is formed, with the acid polymer (d) can be made by contacting the ion sustained-release glass with an acid polymer solution by impregnation, spray, or the like. As an example, the polysiloxane-coated ion sustained-release glass is caused to dry flow and, in the flow state, the acid polymer solution is dispersed from above and sufficiently stirred. The method of dispersing the acid polymer solution is not particularly limited, though dropping or spray that enables uniform dispersion is preferable. The reaction is preferably conducted around ambient temperature. If the temperature is high, the reaction between the acid reactive element and the acid polymer accelerates and the acid polymer phase formation is not uniform.

After heat treatment, the heat-treated object can be easily crushed by applying a shearing force or an impact force. The crushing may be performed with, for example, the facility used in the above-mentioned reaction.

A solvent employed for preparing the acid polymer solution used in the reaction may be any solvent for dissolving the acid polymer. Examples of the solvent include water, methanol, ethanol, and acetone. Of these, water is particularly preferable. When water is used, an acid group of the acid polymer dissociates and reacts uniformly with the surface of the ion sustained-release glass. The weight molecular weight of the polymer dissolved in the acid polymer solution is in the range of 2000 to 50000, and preferably in the range of 5000 to 40000. Surface-treated ion sustained-release glass treated with an acid polymer whose weight-average molecular weight is less than 2000 tends to have low ion sustained releasability. An acid polymer whose weight-average molecular weight exceeds 5000 increases the viscosity of the acid polymer solution, and makes it difficult to perform acid polymer treatment. The acid polymer concentration in the acid polymer solution is preferably in the range of 3% to 25% by weight, and more preferably in the range of 8% to 20% by weight. In the case where the acid polymer concentration is less than 3% by weight, the above-mentioned acid polymer phase is weak. In the case where the acid polymer concentration exceeds 25% by weight, the polysiloxane layer (porous) is difficult to be diffused. Besides, problems such as the following arise: the acid-base reaction accelerates upon contact with the ion sustained-release glass, and hardening begins during the reaction and condensation occurs. The addition amount of the acid polymer solution to the polysiloxane-coated ion sustained-release glass is preferably in the range of 6% to 40% by weight, and more preferably in the range of 10% to 30% by weight. Converting this addition amount, an optimal amount of the acid polymer with respect to the polysiloxane-coated ion sustained-release glass is in the range of 1% to 7% by weight, and an optimal amount of water is in the range of 10% to 25% by weight.

—Acid Polymer (d)

The acid polymer that can be used to form the acid polymer reaction phase on the surface of the polysiloxane-coated ion sustained-release glass by the method described above is a copolymer or a homopolymer of a polymerizable monomer having an acid group such as a phosphoric acid residue, a pyrophosphoric acid residue, a thiophosphoric acid residue, a carboxylic acid residue, or a sulfonic acid group. Examples of the polymerizable monomer include acrylic acid, methacrylic acid, 2-chloroacrylic acid, 3-chloroacrylic acid, aconitic acid, mesaconic acid, maleic acid, itaconic acid, fumaric acid, glutaconic acid, citraconic acid, 4-(meth)acryloyloxyethoxycarbonylphthalic acid, 4-(meth)acryloyloxyethoxycarbonylphthalic anhydride, 5-(meth)acryloylaminopentylcarboxylic acid, 11-(meth)acryloyloxy-1,1-undecanedicarboxylic acid, 2-(meth)acryloyloxyethyldihydrogenphosphate, 10-(meth)acryloyloxydecyldihydrogenphosphate, 20-(meth)acryloyloxyeicosyldihydrogenphosphate, 1,3-di(meth)acryloyloxypropyl-2-dihydrogenphosphate, 2-(meth)acryloyloxyethylphenyl phosphoric acid, 2-(meth)acryloyloxyethyl-2'-bromoethyl phosphoric acid, (meth)acryloyloxyethylphenylphosphonate, di(2-(meth)acryloyloxyethyl)pyrophosphate, 2-(meth)acryloyloxyethyldihydrogendithiophosphate, and 10-(meth)acryloyloxydecyldihydrogenthiophosphate. Of these polymers, a homopolymer or a copolymer of α-β unsaturated carboxylic acid that is relatively slow in acid-base reaction with an acid reactive element is preferable. An acrylic acid polymer, an acrylic acid-maleic acid copolymer, and an acrylic acid-itaconic acid copolymer are more preferable.

The ion sustained-release glass (a) used in the present invention has a feature of continuously sustained-releasing an ion species resulting from the glass composition, and is different from temporary release of a large amount by dissolution of a metal fluoride or the like in water. Whether or not the ion sustained-release glass or another filler has ion sustained releasability can be determined by the following method.

0.1 g of the ion sustained-release glass or another filler is added to 100 g of distilled water. The ion sustained-release glass or another filler can be regarded as having ion sustained releasability in the case where the ion concentration (F1) or the element concentration (F1) attributable to the ion species sustain-released in the distilled water when stirred for 1 hour and the ion concentration (F2) or the element concentration (F2) attributable to the ion species sustained-released in the distilled water when stirred for 2 hours satisfy the relationship of the following Expression (1):

$$F2 > F1 \qquad \text{Expression (1)}.$$

Here, F1 or F2 may be the ion concentration analyzed by a fluoride electrode, ion chromatography, etc. Alternatively, the element concentration attributable to the ion species, which is analyzed using an inductively coupled plasma atomic emission spectrophotometer, etc. and correlated with the ion concentration, may be used instead of the ion concentration. If a plurality of types of ions are sustained-released from the ion sustained-release glass, the ion concentrations or element concentrations of all types of ions do not necessarily need to satisfy Expression (1). The ion sustained-release glass may be regarded as having ion sustained releasability in the case where the ion concentration or element concentration of at least one type of ion satisfies Expression (1). The ion sustained-release glass used in the present invention preferably has an acid neutralizing capacity attributable to the ion sustained release effect. The acid neutralizing capacity can be checked by adding 0.1 g of the ion sustained-release glass to 10 g of a lactic acid water solution with pH adjusted to 4.0, and measuring the pH change when stirred for 5 minutes. The ion sustained-release glass can be regarded as having an acid neutralizing capacity in the case where the pH is greater than or equal to 5.5, more preferably greater than or equal to 6.0, and most preferably greater than or equal to 6.5.

[Neutralization Promoting Ion Sustained-Release Dental Film]

The dental composition according to the present invention is suitable for use as a neutralization promoting ion sustained-release dental film, in the case where the carrier (b) is the film forming material (e). In this case, the content of the ion sustained-release glass (a) is preferably in the range of 1% to 35% by weight and more preferably in the range of 5% to 30% by weight, with respect to the total amount of the neutralization promoting ion sustained-release dental film. In the case where the content of the ion sustained-release glass (a) is less than 5% by weight, the amount of sustained-released ion is insufficient, and the tooth substance strengthening effect, the secondary caries suppression effect, and the like cannot be expected. In the case where the content of the ion sustained-release glass (a) exceeds 35% by weight, the neutralization promoting ion sustained-release dental film is weak and difficult to handle.

—Film Forming Material (e)

Examples of the film forming material (e) used as the carrier (b) in the neutralization promoting ion sustained-release dental film according to the present invention include polyvinylpyrrolidone, polyvinylalcohol, polyethyleneglycol, sodium polyacrylate, carboxymethylcellulose, hydroxypropylcellulose, ethylcellulose, hydroxyethylcellulose, hydroxypropylmethylcellulose, hydroxypropylmethylcellulose phthalate (HPMCP), cellulose acetate phthalate (CAP), carboxymethylethylcellulose (CMEC), carboxymethylcellulose potassium, carboxymethylcellulose sodium, carboxymethylcellulose calcium, starch, xanthan gum, karaya gum, alginate sodium, methylcellulose, carboxyvinyl polymer, agar, amylose, pullulan, chitosan, starch, rosin, sodium carboxymethyl starch, plantago testa, galactomannan, Eudragit, casein, alginate alkyl ester, gelatin, hydroxyethylmethyl cellulose, ethyl methacrylate/chloridized trimethylammonium ethyl methacrylate copolymer, dimethylaminoethyl methacrylate/methyl methacrylate copolymer, pullulan, and acrylic acid/methyl methacrylate copolymer. To hold the film forming material (e) on a prosthetic device or an oral cavity tissue and retain it in the oral cavity, the film forming material (e) preferably has a polar group such as a carbonyl group, a hydroxy group, an amide group, an amino group, or a carboxyl group, and starch, alginate sodium, and polyvinylpyrrolidone are suitable. These film components may be used singly or in combination. For example, two or more types of film components that differ in dissolution rate in the oral cavity may be mixed to control the amount of sustained-released ion.

The blending quantity of the film forming material (e) is preferably 60% to 90%. In the case where the blending quantity of the film forming material (e) is less than 60%, it is difficult to form a film. In the case where the blending quantity of the film forming material (e) exceeds 90%, the ion sustained releasability decreases significantly.

The neutralization promoting ion sustained-release dental film according to the present invention may contain a fluoride ion supply material. Specific examples of the fluoride ion supply material include a fluoride salt and a plant-derived fluorine compound.

—Fluoride Salt

Examples of the fluoride salt include lithium fluoride, sodium fluoride, potassium fluoride, rubidium fluoride, cesium fluoride, beryllium fluoride, magnesium fluoride, calcium fluoride, strontium fluoride, barium fluoride, aluminum fluoride, manganese(II) fluoride, iron(II) fluoride, iron (III) fluoride, silver(I) fluoride, diammine silver fluoride, sodium hydrogenfluoride, potassium hydrogenfluoride, sodium fluorophosphates, potassium hexafluorotitanate, sodium hexafluorosilicate, sodium hexafluorophosphate, pentafluoro-2-sodium stannate(II), and potassium hexafluorozirconate. Of these examples of the fluoride salt, lithium fluoride, sodium fluoride, potassium fluoride, magnesium fluoride, calcium fluoride, strontium fluoride, barium fluoride, and calcium fluoride are preferable, and sodium fluoride is most preferable. To control the amount of ion such as the fluoride ion flowing out from the fluoride salt, a fluoride salt functionalized by surface treatment, surface coating, etc. may be used without any limitation. An example of the plant-derived fluorine compound is tea extract fluorine extracted from tea leaves. The fluoride ion supply materials may be used singly or in combination. The blending quantity of the fluoride ion supply material is preferably 0.1% to 10%. In the case where the blending quantity of the fluoride ion supply material is less than 0.1%, the increase of the sustained release amount of the fluoride ion is small. In the case where the blending quantity of the fluoride ion supply material exceeds 10%, the fluoride ion supply material flows out in the oral cavity and as a result the film becomes weak.

The neutralization promoting ion sustained-release dental film according to the present invention may contain a saliva secretion promoter. The saliva secretion promoter is a component for promoting saliva secretion in the oral cavity. When the amount of saliva secretion increases, food residue and light plaque in the oral cavity are washed away, which is effective for the prevention of dental caries. As the saliva secretion promoter, an organic acid is applicable. Specific examples include citric acid, tartaric acid, fumaric acid, malic acid, succinic acid, and lactic acid. The saliva secretion promoters may be used singly or in combination. The blending quantity of the organic acid is preferably 0.05% to 1%. In the case where the blending quantity of the organic acid is less than 0.05%, the promotion of saliva secretion is insufficient. In the case where the blending quantity of the organic acid exceeds 1%, the film has a very strong acid taste and is not suitable for eating.

The neutralization promoting ion sustained-release dental film according to the present invention may contain a saliva buffering capacity improver. The saliva buffering capacity improver is a substance having a function of promptly neutralizing the oral cavity in the case where the pH in the oral cavity decreases. Specific example of the saliva buffering capacity improver include sodium hydrogencarbonate, disodium hydrogenphosphate, calcium hydrogenphosphate, tricalcium phosphate, sodium carbonate, and a basic amino acid such as arginine. The saliva buffering capacity improvers may be used singly or in combination. The neutralization promoting ion sustained-release dental film according to the present invention also sustained-releases the strontium ion in the oral cavity by the effect of the specific ion sustained-release glass contained therein, which is expected to synergistically enhance the saliva buffering capacity.

The blending quantity of the saliva buffering capacity improver is preferably 5% to 20%. In the case where the blending quantity of the saliva buffering capacity improver is less than 5%, the saliva buffering capacity is not exhibited. In the case where the blending quantity of the saliva buffering capacity improver exceeds 20%, the neutralization promoting ion sustained-release dental film is weak and difficult to handle.

The neutralization promoting ion sustained-release dental film according to the present invention may contain an antibacterial agent. Specific examples of the antibacterial agent include: cationic antibacterial agents such as chlorhexidine, cetylpyridinium chloride, benzethonium chloride, benzalkonium chloride, and dequalinium chloride; and nonionic antibacterial agents such as isopropylmethylphenol and halogenated diphenyl ether. The antibacterial agents may be used singly or in combination.

In the case where the specific ion sustained-release glass in the neutralization promoting ion sustained-release dental film according to the present invention contains boric acid, the borate ion is sustained-released in the oral cavity, which is expected to synergistically enhance the antibacterial property or the bacteriostatic property.

The neutralization promoting ion sustained-release dental film according to the present invention may contain a sweetener. As the sweetener, an artificial sweetener which is a noncariogenic sweetener is particularly preferable. The artificial sweetener is not metabolized by bacteria in the oral cavity and hardly produces acid, and therefore does not cause a decrease in pH in the oral cavity. Specific examples of the artificial sweetener include xylitol, maltitol, aspartame, sorbitol, saccharin sodium, sucralose, reduced palatinose, palatinose, mannitol, erythritol, and cyclodextrin. The sweeteners may be used singly or in combination.

The thickness of the neutralization promoting ion sustained-release dental film according to the present invention is preferably 15 µm to 500 µm, more preferably 20 µm to 200 µm, and most preferably 25 µm to 60 µm, in terms of operability. In the case where the thickness of the neutralization promoting ion sustained-release dental film is less than 15 µm, the neutralization promoting ion sustained-release dental film is weak and difficult to handle. In the case where the thickness of the neutralization promoting ion sustained-release dental film exceeds 500 µm, the neutralization promoting ion sustained-release dental film has low flexibility and is difficult to be attached to a complex part.

The shape of the neutralization promoting ion sustained-release dental film may be, but not limited to, a circle, an ellipse, a rectangle, a square, a polygon, or the like, so long as it can be attached to an oral cavity tissue or a prosthetic device. The area of the neutralization promoting ion sustained-release dental film is preferably 0.5 $cm^2$ to 25 $cm^2$. In the case where the area of the neutralization promoting ion sustained-release dental film is less than 0.5 $cm^2$, the ion sustained releasability is insufficient. In the case where the area of the neutralization promoting ion sustained-release dental film exceeds 25 $cm^2$, the neutralization promoting ion sustained-release dental film is difficult to handle.

The neutralization promoting ion sustained-release dental film according to the present invention can be attached to any part of the oral cavity or a prosthetic device, so long as the surface is smooth. For example, the neutralization promoting ion sustained-release dental film can be attached to an oral cavity tissue such as the tooth substance, the tongue, or the palate, or a prosthetic device such as a denture.

The neutralization promoting ion sustained-release dental film according to the present invention may have a multilayer structure in order to control the ion sustained releasability. For example, the ion sustained releasability can be controlled by forming a film of a three-layer structure in which the inner layer is a film layer including the ion sustained-release glass and the two outer layers are made of only the film component. Alternatively, in a neutralization promoting ion sustained-release dental film of a two-layer structure in which one layer is made of the ion sustained-release glass and a readily water-soluble film component and the other layer is made of a hardly water-soluble film component, the ion can be effectively sustained-released only from the readily water-soluble film layer. A film of a multilayer structure can be manufactured, for example, by forming a plurality of films separately and then pressing or welding the films together.

The manufacturing method of the film according to the present invention is not particularly limited, though the following method is preferable as an example. The film forming material and the like are dissolved or swollen in a volatile organic solvent with a boiling point of 100° C. or less, such as water, ethanol, or acetone. After the ion sustained-release glass is dispersed in the dissolved or swollen liquid, it is dried by heating at 100° C. or more to remove the volatile organic solvent, thus obtaining the film.

[Dental Varnish Composition]

The dental composition according to the present invention is suitable for use as a dental varnish composition, in the case where the carrier (b) is the film component (f) and the organic solvent (g). JP 2001-288025 A, JP 2006-16396 A, JP 2008-127391 A, JP S62-277953 A, and US 2004/0071638 each disclose a dental varnish containing a fluoride salt as a fluoride ion supply source, a film component (e.g. a rosin resin, a polymer, an oligomer, a monomer) for thin film formation, and an organic solvent. JP 2001-288025 A, JP 2006-16396 A, and JP 2008-127391 A suggest that: when the dental varnish is applied to the tooth substance, the organic solvent transpires and a thin film made of the film component and the fluoride salt is formed on the surface of the tooth substance, and the fluoride ion of high concentration is continuously released in the oral cavity from the formed thin film, which is expected to strengthen the tooth substance and improve the acid resistance; and for the tooth substance with exposed dentin, the dental varnish can seal dentinal tubules, which is effective in suppressing hyperesthesia. Moreover, since the dental varnish is removable by a toothbrush and the like, the dental varnish can be removed at any timing. JP S62-277953 A discloses a dental varnish containing polystyrene resin and rosin as a film component, where the inclusion of rosin and polystyrene resin as a film component improves the adhesion and the durability. In such a dental varnish, however, the fluoride ion is released by the physical dissolution of the fluoride salt. The film formed on the tooth substance weakens over time due to the dissolution of the fluoride salt, and also the strength of the formed film is weak because the film component is made of only polystyrene resin and rosin. Such factors cause peeling of the film from the tooth substance, and high retentivity on the tooth substance cannot be expected. Besides, since the release of the fluoride ion depends on the dissolution of the fluoride salt, the release period is relatively short, and the continuous release of the fluoride ion cannot be expected. US 2004/0071638 discloses a dental varnish containing glycerin, where the inclusion of glycerin enables more efficient release of the fluoride ion. It is believed that, by including glycerin with high hydrophilicity in the dental varnish, the infiltration of water into the film formed on the tooth substance is facilitated, thus promoting the release of the fluoride ion. However, the release of the fluoride ion is temporary as in JP S62-277953 A (PTL 6), and the continuous release of the fluoride ion cannot be expected. The dental varnish also has a problem in that the film formed on the tooth substance is weak and peels away from the tooth substance in a short time, as in PTL 6. Note that the entire disclosure of each of the above-mentioned documents is incorporated in this specification by reference.

A dental varnish containing only a fluoride salt such as sodium fluoride as a fluoride ion supply source is expected to release the fluoride ion in an initial stage following the film formation on the tooth substance, but the release period is short and so the continuous release of the fluoride ion cannot be expected. The dental varnish thus has a problem in that the acid resistance improvement effect is insufficient because the supply of the fluoride ion to the tooth substance is of short duration. The conventional varnish composition also has a problem in that the film formed on the tooth substance is weak and peels away in a relatively short time. As a result of conducting intensive study to overcome the problems stated above, the inventors have found out that the following effects are achieved by including ion sustained-release glass in the dental varnish composition. In the case where the dental varnish composition according to the present invention is applied onto the tooth substance, the retentivity of the formed film on the tooth substance is improved as compared with the conventional dental varnish, and the strontium ion and the aluminum ion sustained-released from the ion sustained-release glass have the effect of exhibiting the acid buffering capacity which is effective in suppressing dental caries. The inventors have then completed the present invention.

The present invention provides the following various features. The inclusion of the ion sustained-release glass in the dental varnish composition is assumed to significantly improve the strength and thickness of the film formed on the tooth substance, the adhesion of the film to the tooth substance, and the like. Therefore, the dental varnish composition according to the present invention not only improves the retentivity on the tooth substance, but also has excellent effects for healthy oral cavity environment as the fluoride ion is continuously sustained-released in the retention period and influences the strengthening of the tooth substance, the suppression of secondary caries, the suppression of decalcification, the recalcification, and the like. Moreover, by including specific ion sustained-release glass in the dental varnish composition according to the present invention, it is possible to obtain a new dental varnish composition unlike any conventional dental varnish composition, such as: a rechargeable dental varnish composition that can not only sustained-release various ions including the fluoride ion but also take in various ions from outside and sustained-release the ions again; and a dental varnish composition capable of two-step ion sustained release by including a conventionally used metal fluoride salt so that the synergistic effect of the initial sustained release of a large amount of fluoride ion by the metal fluoride salt and the continuous sustained release of various ions by the ion sustained-release glass can be expected.

Another effect of the present invention is as follows. By the inclusion of the specific ion sustained-release glass, the strontium ion or the aluminum ion is sustained-released in the oral cavity. These ions exhibit an acid neutralizing effect. Accordingly, in the case where the oral cavity environment becomes more acidic, the oral cavity environment can be neutralized. The dental caries suppression effect and the acid buffering capacity effect can thus be expected.

Yet another effect of the present invention is as follows. By the inclusion of the specific ion sustained-release glass, the borate ion is sustained-released in the oral cavity. The antibacterial and bacteriostatic effects of the borate ion can suppress the growth of bacteria, which is effective for the prevention of foul breath, periodontal disease, etc.

The content of the ion sustained-release glass (a) is not particularly limited. The content of the ion sustained-release glass (a) is preferably greater than or equal to 5% by weight and more preferably in the range of 5% to 60% by weight, with respect to the total amount of the dental varnish composition. In the case where the content of the ion sustained-release glass (a) is less than 5% by weight, the amount of sustained-released ion is insufficient, and the tooth substance strengthening effect, the secondary caries suppression effect, and the like cannot be expected. In the case where the content of the ion sustained-release glass (a) exceeds 60% by weight, the viscosity of the dental varnish composition is high and a problem such as a decrease in operability arises.

—Film Component (f)

The film component (f) used in the dental varnish composition according to the present invention is not limited so long as it is compatible with or is swollen in the organic solvent (g). Rosin or a high molecular weight organic compound is preferably used as the film component (f). Specific examples of the rosin include hydrogenated rosin, disproportionated rosin, esterified rosin, polymerized rosin, colophonium, copal, and cumarone resin. Of these, hydrogenated rosin, disproportionated rosin, esterified rosin, etc. having excellent color stability are more preferable. The high molecular weight organic compound is not limited so long as it dissolves in the organic solvent and in particular ethanol. A specific example is a high molecular weight organic compound with a molecular weight of about 1000 to 20000, in terms of ethanol affinity. These film components may be used singly or in combination. The content of the film component (f) in the dental varnish composition according to the present invention is preferably in the range of 20% to 80% by mass and more preferably in the range of 30% to 60% by mass, as a film of proper thickness needs to be formed on the tooth substance. In the case where the content of the film component (f) is less than 20% by mass, the formed coating is thin and tends to peel away from the tooth substance. In the case where the content of the film component (f) exceeds 80% by mass, the viscosity of the dental varnish composition is high and the operability decreases.

—Organic Solvent (g)

The organic solvent (g) used in the dental varnish composition according to the present invention is not limited so long as it is compatible with the film component (f). In terms of transpirability, the organic solvent (g) preferably has a boiling point of 105° C. or less in 760 mmHg, and a vapor pressure of 1.0 KPa or more at 20° C. Specific examples include methanol, ethanol, n-propanol, isopropyl alcohol, acetone, methyl ethyl ketone, and methyl methacrylate. Of these organic solvents (g), ethanol and n-hexane are particularly preferable. These organic solvents may be used singly or in combination. The content of the organic solvent (g) is not particularly limited so long as it is in the range where, after the dental varnish composition is applied onto the tooth substance, the organic solvent transpires and forms a coating of proper thickness. The content of the organic solvent (g) is preferably in the range of 5% to 30% by mass, and more preferably in the range of 10% to 30% by mass. In the case where the content of the organic solvent (g) is less than 5% by mass, the film component has high concentration and so has high viscosity, and the operability decreases. In the case where the content of the organic solvent (g) exceeds 30% by mass, the coating formation is inhibited due to insufficient transpiration of the organic solvent.

—Fluoride Salt

The fluoride salt used in the dental varnish composition according to the present invention is not particularly limited, and may be the fluoride salt usable in the neutralization promoting ion sustained-release dental film.

The content of the fluoride salt in the dental varnish composition according to the present invention is not particularly limited, and may be selected from any range. The content of the fluoride salt is preferably in the range of 1% to 10% by mass, and more preferably in the range of 3% to 8% by mass.

In the case where the content of the fluoride salt is less than 1% by mass, the amount of fluoride ion flowing out is small, the effect of the inclusion of the fluoride salt is not evident. In the case where the content of the fluoride salt exceeds 10% by mass, the physical dissolution of the fluoride salt weakens the film formed on the tooth substance, leading to a problem with retentivity.

The dental varnish composition according to the present invention may contain water or a hydrophilic compound, in order to promote the sustained release of ion. The water used in the dental varnish composition according to the present invention is preferably water that is clinically acceptable as a medical component and does not substantially include any harmful impurity. Distilled water (or purified water) or ion-exchange water (or deionized water) is suitable. The hydrophilic compound used in the dental varnish composition according to the present invention desirably mixes with water. Specific examples include glycerin, polyethyleneglycol, polypropyleneglycol, 2-hydroxyethylmethacrylate, and polyethyleneglycol dimethacrylate, and glycerin and polyethyleneglycol are preferable. These water or hydrophilic compounds may be used singly or in combination.

The dental varnish composition according to the present invention may contain a coloring agent. The coloring agent enables adjustment to a color similar to the tooth in order to provide esthetics, or adjustment to a color distinguishable from the tooth in order to improve the removability and the visibility. The coloring agent may be an organic coloring agent or an inorganic coloring agent. Examples of the organic coloring agent include an azo pigment, a phthalocyanine pigment, and a polycyclic pigment. Examples of the inorganic coloring agent include titanium oxide, rutile titanium, anatase titanium, zinc oxide, aluminum oxide, zinc sulfide, yellow iron oxide, ultramarine blue, red iron oxide, carbon black, and graphite. These coloring agents may be used singly or in combination.

The dental varnish composition according to the present invention may contain a sweetener. The sweetener may be the sweetener usable in the neutralization promoting ion sustained-release dental film.

The dental varnish composition according to the present invention may contain a viscosity modifier to uniformly disperse the ion sustained-release glass in the dental varnish composition. Specific examples of the viscosity modifier include cellulose derivative, polyacrylic acid, vinyl alcohol, xanthan gum, silica, polyamide resin, and polyvinylpyrrolidone. Silica or polyvinylpyrrolidone that has high hydrophilicity and does not inhibit the sustained release of ion is most suitable. These viscosity modifiers may be used singly or in combination.

The dental varnish composition according to the present invention is a paste, a gel, or a liquid, and can be applied to the tooth substance using an application such as a brush. When the dental varnish composition is applied to the tooth surface, the organic solvent (g) in the composition transpires and a thin film made of the film component (f) and the ion sustained-release glass (a) is formed on the surface of the tooth substance, and ions are continuously released in the oral cavity from the formed thin film. This can be expected to strengthen the tooth substance, improve the acid resistance, and suppress foul breath. For the tooth substance with exposed dentin, the dental varnish composition can seal dentinal tubules, and so can be also used as a hyperesthesia inhibitor.

The manufacturing method of the dental varnish composition according to the present invention is not particularly limited, though the following method is preferable as an example.

Each material is mixed using a rotary agitation mixer such as a turbula mixer, a centrifugal mixer, or a planetary centrifugal mixer.

[Dental Gum Composition]

The dental composition according to the present invention is suitable for use as a dental gum composition, in the case where the carrier (b) is the gum base (h). The calcium ion and the phosphate included in saliva act on the tooth substance, as a result of which recalcification is exhibited. In a healthy state, the equilibrium between decalcification and calcification is kept on the surface of the tooth substance. When plaque adheres, however, saliva cannot reach the surface of the tooth substance, and the recalcification action by saliva becomes ineffective. As a result, decalcification becomes more dominant, eventually resulting in dental caries. To maintain the healthy state, it is effective to remove plaque adhering to the tooth substance.

The most effective means for removing plaque is brushing in the oral cavity using a toothbrush, i.e. physical removal. As auxiliary means other than brushing, a physical plaque removal method by mastication of a gum composition is known as described in the Japanese Journal of Conservative Dentistry 44(2), 324 to 329. The gum composition is mainly composed of a viscous gum base, and so can capture the plaque formed on the surface of the tooth substance. "The Japanese Journal of Conservative Dentistry 44(2), 324 to 329" also describes that plaque on the tooth substance can be efficiently removed by including calcium carbonate, which is used as an abrasive in a dentifrice, in the gum composition. Moreover, a gum composition containing a noncariogenic sweetener is commercially available. The noncariogenic sweetener is an artificial sweetener that is not metabolized by bacteria in the oral cavity and hardly produces acid and so does not induce dental caries, while having the same sweetness as a conventional cariogenic sweetener such as glucose, fructose, or sucrose. The gum composition containing the noncariogenic sweetener does not induce dental caries and can physically remove plaque, and so is an effective material for the prevention of dental caries. However, the gum composition containing the noncariogenic sweetener has a problem in that its effect is limited only to the prevention of dental caries, and does not involve the improvement in acid resistance of the tooth substance or the capacity of inducing recalcification.

JP 2007-314505 A discloses an antibacterial gum composition containing chitosan oligosaccharide as an antibacterial component. Chitosan is obtained by chemically treating chitin which is a component included in the shells of crabs or shrimps, and has a structure of β-1,4-linked D-glucosamine. Chitosan is a polysaccharide having various deacetylation degrees. While being used as artificial skin for its high affinity for organisms, in recent years chitosan is also reported to have an antibacterial action against $S.\ mutans$ which is a cause of dental caries. The antibacterial gum composition containing chitosan oligosaccharide can suppress the growth of cariogenic bacteria by its antibacterial effect, and keep the oral cavity clean to prevent dental caries.

JP 2009-525988 T and WO 2010/061932 A1 each disclose an oral cavity care composition having a calcium ion supply source and a fluoride ion supply source. JP 2009-525988 T discloses a composition including a stabilized amorphous calcium phosphate (ACP) or stabilized amorphous calcium fluorophosphate (ACFP) composite fluoride and a fluoride ion source. The ACP or ACFP-derived calcium ion and the fluoride ion sustained-released from the fluoride ion source are taken into the decalcified tooth substance, as a result of which fluoroapatite is formed in the tooth substance simultaneously with recalcification, which is expected to improve the acid resistance of the tooth substance as well as recalcification. However, this composition has a problem in that the fluoride ion and the calcium ion flowing out from ACP or ACFP form insoluble calcium fluoride in a moist environment as in the oral cavity and settle out, and so the acid resistance of the tooth substance cannot be improved.

WO 2010/061932 A1 discloses a gum composition containing phosphorylated sugar calcium salt or water-soluble calcium salt as a calcium ion supply source, fluoride as a fluoride ion supply source, and polyphenol. The disclosed invention has a feature that, in the case where the gum composition is present in the oral cavity, the calcium ion, the fluoride ion, and the polyphenol are sustained-released in the saliva and taken into the tooth substance, to improve the acid resistance of the tooth substance and exhibit the recalcification capacity. However, this gum composition has a problem in that the fluoride ion and the calcium ion form insoluble calcium fluoride in a moist environment as in the oral cavity and settle out, and so the acid resistance of the tooth substance cannot be improved, as in JP 2009-525988 A.

A gum composition containing a supply source of calcium ion that induces recalcification and a supply source of fluoride ion that improves the acid resistance of the tooth substance is a useful material in terms of the induction of recalcification and the formation of fluoroapatite. However, since saliva, i.e. water, exists in the actual oral cavity, if the calcium ion source and the fluoride ion source are present in the same composition, nearby ions react with each other and form calcium fluoride at the instant when these ion supply sources dissolve. The calcium fluoride is hardly soluble in water. Accordingly, once the salt formation has occurred, it does not dissolve in saliva and so cannot be expected to recalcify the tooth substance and improve the acid resistance. Note that the entire disclosure of each of the above-mentioned documents is incorporated in this specification by reference.

As a result of conducting intensive study to overcome the problems stated above, the inventors have found out that, by including ion sustained-release glass in the gum composition, the fluoride ion and the strontium ion can be sustained-released in the oral cavity when the gum composition according to the present invention is masticated. The inventors have then completed the present invention. In detail, the inventors provide the following invention.

The blending quantity of the ion sustained-release glass (a) is greater than or equal to 5% by mass, in terms of the amount of sustained-released fluoride ion. The blending quantity of the ion sustained-release glass (a) is preferably 10% to 50% by mass, and more preferably 15% to 40% by mass. In the case where the blending quantity of the ion sustained-release glass (a) is less than 10% by mass, the ion sustained releasability is poor. In the case where the blending quantity of the ion sustained-release glass (a) exceeds 50% by mass, the gum composition is hard and is not suitable for mastication.

The gum composition according to the present invention essentially contains the gum base (h). The gum base means a base material that is included in the gam composition and maintains proper flexibility in the oral cavity, and has an effect of holding ion sustained-release glass, a sweetener, a flavorant, etc. as a mass. When the gum composition is masticated, the gum base remains in the oral cavity last. The gum base may be any well-known gum base. Specific examples include guaiac acid, shellac, jelutong, sorva, a natural resin such as dammar gum, natural chicle, vinyl acetate, polybutene, talc, micro crystalline wax, candelilla wax, glycerine fatty acid ester, hydrogenated oil, sorbitan fatty acid ester, calcium carbonate, rice bran wax, natural rubber, mastic, carnauba wax, gutta-percha, chicle, ester gum, polyisobutylene, styrene butadiene rubber, polylactic acid, natural rubber, natural resin, acetylated monoglyceride, micro crystalline wax, and fatty acid monoglyceride. The gum base (h) is preferably 20% to 60% by mass with respect to the gum composition, in terms of the texture and palatability of the gum composition.

The gum composition according to the present invention may contain a fluoride ion supply material in addition to the ion sustained-release glass (a), to synergistically sustained-release the fluoride ion. Examples of the fluoride ion supply material include a fluoride salt and a plant-derived fluorine compound. The fluoride salt is not particularly limited, and may be the fluoride salt usable in the neutralization promoting ion sustained-release dental film. The plant-derived fluorine compound may be tea extract fluorine extracted from tea leaves. The fluoride ion supply materials may be used singly or in combination.

The gum composition according to the present invention may contain a sweetener. The sweetener may be the sweetener usable in the neutralization promoting ion sustained-release dental film.

The gum composition according to the present invention may contain a saliva secretion promoter. The saliva secretion promoter may be the saliva secretion promoter usable in the neutralization promoting ion sustained-release dental film.

The gum composition according to the present invention may contain a saliva buffering capacity improver. The saliva buffering capacity improver may be the saliva buffering capacity improver usable in the neutralization promoting ion sustained-release dental film. The gum composition according to the present invention also sustained-releases the strontium ion in the oral cavity by the effect of the ion sustained-release glass contained therein, which is expected to synergistically enhance the saliva buffering capacity.

The gum composition according to the present invention may contain an antibacterial agent. The antibacterial agent may be the antibacterial agent usable in the neutralization promoting ion sustained-release dental film. The gum composition according to the present invention also sustained-releases the borate ion in the oral cavity by the effect of the specific ion sustained-release glass contained therein, which is expected to synergistically enhance the antibacterial property or the bacteriostatic property.

The gum composition according to the present invention may include a known material such as gelatin, a flavorant, a gloss agent, a colorant, a thickener, an acidulant, a pH adjuster, etc.

The gum composition according to the present invention may be shaped like a sheet, a tablet, a sphere, etc., and coated with a sugar coating material on the gum surface. The sugar coating material may contain the saliva secretion promoter, the ion sustained-release glass, the antibacterial agent, the sweetener, etc. The gum composition according to the present invention can be masticated in the oral cavity.

The manufacturing method of the gum composition according to the present invention is not particularly limited, though the following method is preferable as an example.

After the gum base is produced using a kneader, a pressure kneader, or the like, the ion sustained-release glass (a) is added to the gum base and kneaded to prepare the gum composition, which is manufactured using a pressure molding machine or a tablet molding machine.

[Oral Cavity Care Composition]

The dental composition according to the present invention is suitable for use as an oral cavity care composition, in the case where the carrier (b) is the water (i). JP 2002-167318

A discloses a solid oral cavity composition containing a calcium-containing component, a fluorine-containing component and/or a phosphate, an organic acid, and a carbonate and/or a hydrogencarbonate. The composition in this prior document comes into contact with saliva and dissolves, as a result of which the calcium ion and the fluoride ion are released. In the initial stage of dissolution of the solid oral cavity composition, the pH is 3 to 4. By the end of dissolution, on the other hand, the pH increases to 5 to 8. This document describes that, by adjusting the pH in the initial stage of dissolution to 3 to 4, the generation and precipitation of the insoluble material is suppressed and the dissolution concentration of the recalcification component is increased, thus producing an effect of promoting recalcification. However, since the critical pH at which enamel is decalcified is about 5.5, it can be easily assumed that the pH of 3 to 4 in the initial stage of dissolution leads to enamel decalcification. Besides, this composition is a solid oral cavity composition that cannot contain water, and accordingly has a problem with use as it takes time to dissolve in saliva after the application in the oral cavity. Further, the effect of the composition is insufficient in, for example, the following point: when the dissolution time is long, the pH increases, and various ions generated by the dissolution react with each other before acting on the tooth substance, thereby forming an insoluble material.

JP 2004-527539 T discloses a dentifrice composition containing calcium carbonate particles treated with a polymer and/or a fatty acid, and fluoride. This document describes that, since the calcium carbonate reacts with the fluoride ion from the fluoride and forms calcium fluoride, the calcium carbonate particles are surface-treated with a polysaccharide and/or a fatty acid to inhibit the reaction, thus enabling the calcium carbonate and the fluoride to coexist. However, surface-treating the calcium carbonate particles makes the release of the calcium ion harder, so that the calcium ion cannot immediately act on the tooth substance when the dentifrice composition is applied into the oral cavity. The effect of recalcification, etc. is therefore insufficient.

JP 2013-163656 A discloses a dentifrice in which at least 60% by weight of the solid component is a calcium compound. According to this prior document, the presence of fluoride is not essential, and the inclusion of the calcium compound at high concentration has an effect of promoting the recalcification of the cementum, dentin, or enamel. Although the effect in the case of including fluoride in the dentifrice composition is not described in this document, when fluoride is included while the calcium compound of high concentration is present, calcium fluoride is likely precipitate, and so the effect of recalcification cannot be expected. Moreover, given that the calcium compound is contained with high concentration, it is assumed that the effect of the calcium compound itself is expected rather than the effect produced by ionizing calcium.

JP H10-330234 A discloses a dentifrice containing a fluorine compound, hydroxyapatite, and xylitol. According to this document, the use of the three components together promotes the recalcification of the tooth surface and so is effective for the prevention of dental caries. However, when the fluorine compound and the hydroxyapatite coexist, the fluoride ion reacts with and is supported by the hydroxyapatite, which results in insufficient recalcification effect on the tooth substance. Since the document has no mention of the prevention of such a reaction, the dentifrice is assumed to change in property over time.

JP H02-142718 A discloses an intraoral composition including a linear polymerized polyelectrolyte, a soluble strontium ion source, and a soluble fluoride ion source. According to this document, while the technique of coexistence of the strontium EDTA complex and the fluoride ion has been used in conventional oral cavity compositions as the strontium ion tends to form an insoluble precipitate with a fluoride, a more effective anti-caries composition is realized by an oral cavity composition in which strontium forms a complex with a linear polymerized polyelectrolyte including a polycarboxyl group, a sulfonate group, or a sulfate group to prevent the formation of a precipitate with a fluoride. However, since the strontium ion forms the complex with the linear polymerized polyelectrolyte, strontium is not present as an ion in the oral cavity composition. When the oral cavity composition in this prior document is applied into the oral cavity, the composition cannot promptly act on the tooth substance and the like, and thus its effect is insufficient.

JP 2011-98920 A discloses a dentifrice including isopropylmethylphenol as a bactericidal component and potassium nitrate, aluminum lactate, or strontium chloride as a hypersensitivity relieving component. According to this prior document, though the coexistence of isopropylmethylphenol and a specific hypersensitivity relieving component causes a disagreeable taste, including a specific flavorant to suppress the disagreeable taste enables the coexistence of isopropylmethylphenol and the specific hypersensitivity relieving component. However, the prior document has no mention of a recalcification component such as calcium, and so the effect of recalcifying the tooth substance cannot be expected.

A dentifrice containing only a fluoride salt such as sodium fluoride as a fluoride ion supply source is expected to release the fluoride ion during brushing, but the fluoride ion alone has only a low level of effectiveness for recalcification and the like. If the calcium ion or the phosphate ion as a recalcification component is provided to coexist with the fluoride ion in order to increase the recalcification effect and the like, an insoluble substance such as calcium fluoride or calcium phosphate is generated and precipitates. Thus, there are problems such as poor storage stability as the paste property changes in the container, and an insufficient effect on the tooth substance as the components are not ionized when the dentifrice is applied into the oral cavity.

This raises the need for an oral cavity care composition that: has excellent storage stability with no problem of generation/precipitation of an insoluble substance even in the case where the fluoride ion coexists with another ionized component; produces the recalcification effect, the decalcification inhibition effect, etc. with the ionized components acting on the tooth substance or oral cavity tissue as promptly as possible upon application into the oral cavity; and is also effective in antibacterial and bacteriostatic action. Note that the entire disclosure of each of the above-mentioned documents is incorporated in this specification by reference.

As a result of conducting intensive study to overcome the problems stated above, the inventors have discovered ion sustained-release glass that can sustained-release a plurality of ions simultaneously, instead of a plurality of compounds that respectively sustained-release components exhibiting the recalcification of the tooth substance, the antibacterial and bacteriostatic action, the acid neutralizing capacity for suppressing the decalcification of the tooth substance, and the like. The inventors have completed the present invention by including the ion sustained-release glass in an oral cavity care composition together with water.

In the oral cavity care composition according to the present invention, various ions are sustained-released into the water from the ion sustained-release glass during storage, and establish the equilibrium relation in a saturation state. Since there is no precipitation of a reaction product caused by the reaction of components, excellent storage stability is attained. Moreover, immediately after the oral cavity care composition according to the present invention is applied into the oral cavity, various ions which have been already formed in the oral cavity care composition promptly act in the oral cavity to exhibit the strengthening of the tooth substance, the suppression of dental caries, the suppression of decalcification, and the acid neutralizing capacity and contribute to recalcification and a healthier oral cavity environment by the prevention of periodontal disease, etc. Further, during the application into the oral cavity, the oral cavity care composition is diluted by saliva and the equilibrium relation is lost, as a result of which the ions are continuously sustained-released from the ion sustained-release glass. Further effects can be expected from this.

The content of the ion sustained-release glass (a) is not particularly limited. The content of the ion sustained-release glass (a) is preferably in the range of 1% to 30% by weight and more preferably in the range of 3% to 30% by weight, with respect to the total amount of the oral cavity care composition. In the case where the content of the ion sustained-release glass is less than 1% by weight, the amount of sustained-released ion is insufficient, and the tooth substance strengthening effect, the secondary caries suppression effect, and the like cannot be expected. In the case where the content of the ion sustained-release glass exceeds 30% by weight, the amounts of various ions released by the oral cavity care composition are saturated. Accordingly, further effects cannot be expected even when more ion sustained-release glass are included. Preferably, the ion sustained-release glass is ground into an ion sustained-release glass filler.

The water (i) usable in the oral cavity care composition according to the present invention is preferably water that is clinically acceptable as a medical component and does not substantially include any impurity harmful to the oral cavity care components according to the present invention. Distilled water (or purified water) or ion-exchange water (or deionized water) is suitable. By the inclusion of the water, various ions are sustained-released from the ion sustained-release glass to the oral cavity care composition until the ions are saturated. This enables prompt action on the tooth substance or soft tissue upon application into the oral cavity. In the case where the oral cavity care composition is in paste form, the water (i) may be used in the range of 1% to 50% by weight, and preferably in the range of 5% to 30% by weight. In the case where the oral cavity care composition is in mouthwash form, the water (i) may be used in the range of 30% to 99% by weight, and preferably in the range of 40% to 90% by weight.

The oral cavity care composition according to the present invention may optionally contain, other than water, additives such as a humectant, an abrasive, a foaming agent, a thickener, a pH adjuster, a sweetener, a flavorant, a colorant, and a solubilizer.

The oral cavity care composition according to the present invention may contain a humectant to prevent congelation and separation and make the oral cavity care composition moist. Specific examples of the humectant include sorbitol, glycerin, ethylene glycol, propylene glycol, 1,3-butyleneglycol, propanediol, polyethyleneglycol, and trehalose. Glycerin and sorbitol are preferable. These humectants may be used singly or in combination. The content of the humectant is 5% to 90% by weight and preferably 10% to 70% by weight, with respect to the oral cavity care composition.

The oral cavity care composition according to the present invention may contain an abrasive to polish the tooth substance and remove plaque and the like. Specific examples of the abrasive include aluminum hydroxide, silicic anhydride, alumina, silica gel, hydrated silicate, aluminum silicate, titanium dioxide, and aluminum lactate. Silicic anhydride that is not reactive with the ions sustained-released from the ion sustained-release filler is preferable. These abrasives may be used singly or in combination. The content of the abrasive is 0% to 60% by weight and preferably 0% to 40% by weight, with respect to the oral cavity care composition. It is desirable not to use a calcium compound such as calcium carbonate which is typically used as an abrasive, because it has a possibility of reacting with the fluoride ion and precipitating.

The oral cavity care composition according to the present invention may contain a foaming agent that has an effect of promptly dispersing the composition components in the oral cavity after the application into the oral cavity. Specific examples include sodium laurylsulfate, N-sodium lauroyl-sarcosine, a nonionic surfactant, and an amphoteric surfactant. Sodium laurylsulfate is preferable. These foaming agents may be used singly or in combination. The content of the foaming agent is 0% to 10% by weight and preferably 0% to 5% by weight, with respect to the oral cavity care composition.

The oral cavity care composition according to the present invention may contain a thickener to integrate the powder component and the liquid component to provide proper viscosity. Specific examples include carboxymethylcellulose sodium, hydroxyethylcellulose, hydroxypropylmethylcellulose, xanthan gum, polyvinyl alcohol, sodium polyacrylate, carboxyvinyl polymer, and gelatin. Carboxymethylcellulose sodium is preferable. These thickeners may be used singly or in combination. The content of the thickener is 0.1% to 10% by weight and preferably 0.5% to 5% by weight, with respect to the oral cavity care composition.

The oral cavity care composition according to the present invention may contain a pH adjuster to adjust the pH. Specific examples include sodium hydroxide, citric acid, sodium citrate, gluconic acid, succinic acid, sodium hydrogencarbonate, sodium phthalate, and sodium succinate. These pH adjusters may be used singly or in combination. The content of the pH adjuster is 0.1% to 10% by weight and preferably 0.5% to 5% by weight, with respect to the oral cavity care composition.

The oral cavity care composition according to the present invention may contain a sweetener to enhance the sense of use. An artificial sweetener which is a noncariogenic sweetener is particularly preferable. Specific examples include xylitol, maltitol, aspartame, sorbitol, saccharin sodium, sucralose, reduced palatinose, palatinose, mannitol, erythritol, maltitol, cyclodextrin, and dipotassium glycyrrhizinate. The sweeteners may be used singly or in combination. The sweetener(s) may be optionally used in the oral cavity care composition according to need.

The oral cavity care composition according to the present invention may contain a flavorant to provide refreshing feeling and a flavor. Specific examples include menthol, anethole, isoamyl acetate, methyl salicylate, thymol, spearmint oil, peppermint oil, lemon oil, cinnamon oil, clove oil, eucalyptus, carvone, limonene, methyl salicylate, and saccharin sodium. These flavorants may be used singly or in combination. The content of the flavorant is 0% to 5% by weight and preferably 0.1% to 2% by weight, with respect to the oral cavity care composition.

The oral cavity care composition according to the present invention may contain a solubilizer to solubilize the oily component. Specific examples include polyoxyethylene hardened castor oil, polyoxyethylene polyoxypropylene cetyl ether, polyoxyethylene polyoxypropylene decyl tetradecyl ether, and polyoxyethylene phytosterol. Polyoxyethylene hardened castor oil is preferable. These solubilizers may be used singly or in combination. The solubilizer(s) may be optionally used in the oral cavity care composition according to need.

The oral cavity care composition according to the present invention is in semisolid form such as a paste, a cream, or a gel, or in mouthwash form. In the case where the oral cavity care composition is in semisolid form, the oral cavity care composition is used to polish the tooth surface by turning a brush or a cup, or clean the tooth surface with a household toothbrush. The oral cavity care composition may also be retained in the oral cavity for a predetermined period using a tray or the like so that various ions sustained-released from the ion sustained-release glass act in the oral cavity for a longer time. In the case where the oral cavity care composition is in mouthwash form, the oral cavity care composition is kept in the oral cavity for a predetermined period and then spit out.

The manufacturing method of the oral cavity care composition according to the present invention is not particularly limited. For example, the oral cavity care composition according to the present invention is manufactured by uniformly mixing the oral cavity care composition using a mixer having a moving vane.

[Thermoplastic Sheet Composition]

The dental composition according to the present invention is suitable for use as a thermoplastic sheet composition for mouthguard or splint production, in the case where the carrier (b) is the thermoplastic resin (j).

A thermoplastic sheet is used to produce an intraorally worn device, such as a mouthguard for protecting an athlete from oral cavity injury or a splint used for the prevention of bruxism or for orthodontics.

A mouthguard produced using a thermoplastic sheet is intraorally worn by a player of contact sport such as boxing, rugby, etc., to prevent oral cavity injury caused by an impact during a game.

In recent years, mouthguards are also used in gym class or athletic meet at elementary schools, for the prevention of oral cavity injury. Mouthguards are thus used for a wider range of ages from children to adults who professionally play contact sports.

Wearing a mouthguard has an effect of preventing oral cavity injury. However, there is a problem in that, since the worn mouthguard covers the teeth, the self-cleansing action by saliva cannot be produced and the risk of dental caries increases. The risk of dental caries is higher particularly for children whose enamel is still not mature.

It is also known that sports drinks consumed during sporting activity are low in pH, and the oral cavity of a person after taking a sports drink is exposed to a low pH environment and the enamel is decalcified. Especially when a mouthguard is worn on the teeth, the self-cleansing action by saliva cannot be produced, so that the pH environment remains low. This has a problem of accelerating enamel decalcification.

A split for bruxism prevention is worn in the oral cavity to prevent direct contact and attrition of upper and lower teeth. A splint for orthodontics, which has been molded to an ideal teeth shape beforehand, is worn in the oral cavity so that the teeth are moved into the desired positions according to the splint shape.

These splints have their effects when worn for a long time. When the splint is worn, however, the splint covers the teeth, and accordingly the self-cleansing action by saliva cannot be produced and the risk of dental caries increases. Especially the splint for bruxism prevention is mainly used during sleep when the amount of saliva secretion is small, and so has a problem in that the growth of dental caries-causing bacteria is activated and the risk of dental caries increases. The splint for orthodontics is used during the day when the wearer eats and drinks, and so has a problem in that ingested food and drink stay on the inner surface of the splint and the risk of dental caries further increases.

The above-mentioned intraorally worn device such as a mouthguard or a splint is produced by heat forming. In detail, the upper surface of the thermoplastic sheet is heated by a heater to soften the thermoplastic sheet. The sufficiently softened thermoplastic sheet is pressed against a teeth gypsum model from above, and vacuum suction is performed from under the teeth gypsum model to mold the thermoplastic sheet into the teeth shape.

However, since the thermoplastic sheet has low thermal conductivity, a phenomenon in which the upper surface of the thermoplastic sheet is high in temperature but the lower surface of the thermoplastic sheet is low in temperature occurs during heating, which adversely affects the compatibility when wearing the molded intraorally worn device. For example, in the case where the intraorally worn device is molded in a state when the temperature of the sheet upper surface has reached an appropriate molding temperature but the temperature of the sheet lower surface is below the appropriate molding temperature, the obtained intraorally worn device fails to reproduce the teeth shape in minute detail and does not have sufficient holding power, and so is poor in compatibility. In the case where the intraorally worn device is molded in a state when the sheet lower surface has reached the molding temperature, on the other hand, the upper surface of the thermoplastic sheet is at a temperature higher than the molding temperature, and the obtained intraorally worn device has significant molding distortion due to thermal contraction, and is poor in compatibility upon wearing. The compatibility is particularly poor in the case of using a thick thermoplastic sheet.

As a result of conducting intensive study to solve the problems stated above, the inventors have found out that a thermoplastic sheet composition to which glass is added according to the present invention has improved thermal conductivity and does not have a temperature difference between the upper and lower surfaces of the sheet during heating, and thus can be molded at a lower temperature.

—Thermoplastic Resin (j)

The thermoplastic resin (j) usable in the thermoplastic sheet composition according to the present invention is not limited, so long as it is a thermosoftening resin. In terms of thermoformability, the softening point of the thermoplastic resin (j) is preferably 50° C. to 300° C., and more preferably 60° C. to 150° C. Specific examples of the thermoplastic resin (j) include polystyrene (PS), acrylic resin (PMMA), polycarbonate (PC), polyethylene terephthalate (PET), polypropylene (PP), polyethylene (PP), ethylene-vinyl acetate copolymer (EVA), polyolefin resin, and styrenic elastomer.

For mouthguard production, ethylene-vinyl acetate copolymer (EVA) and polyolefin resin are preferable as they have shock absorption, and ethylene-vinyl acetate copolymer (EVA) with excellent water absorbability is most preferable in order to promote ion release from the ion sustained-release glass included in the mouthguard.

For splint production, acrylic resin (PMMA), polycarbonate (PC), and polyethylene terephthalate (PET) are preferable in terms of material durability and strength.

The thermoplastic resin used in the present invention may be colored. A commonly used coloring agent may be used here. Preferably, an organic pigment is used.

An opaquer is preferably used as a pigment. Typical opaquers include titanium oxide, carbon black, and iron oxide. Titanium oxide is preferable. The content of the pigment is preferably 0.1 parts to 20 parts by weight and more preferably 0.3 parts to 5 parts by weight, with respect to the thermoplastic resin.

The content of the opaquer is preferably 5 parts to 80 parts by weight with respect to the whole pigment. The color is white when the content of the opaquer is 100 parts by weight.

The size of the thermoplastic sheet composition according to the present invention is not particularly limited. The thermoplastic sheet composition is preferably a quadrilateral of 100 mm to 150 mm, or a circle of 100 mm to 150 mm in diameter. The thickness of the thermoplastic sheet composition is 0.2 mm to 5 mm, and preferably 0.5 mm to 4 mm.

The layer structure of the thermoplastic sheet composition according to the present invention is not limited, so long as it includes the ion sustained-release glass. The thermoplastic sheet composition may have a single-layer structure, or a multilayer structure made up of two or more layers.

In the case where the thermoplastic sheet composition has a multilayer structure made up of two or more layers, the sheet layer including the ion sustained-release glass may be on the tooth surface side or on the side opposite to the tooth surface. The arrangement in which the sheet layer including the ion sustained-release glass is on the tooth surface side is expected to strengthen the tooth substance. The arrangement in which the sheet layer including the ion sustained-release glass is on the side opposite to the tooth surface is expected to create a healthier oral cavity environment.

The content of the ion sustained-release glass (a) is not particularly limited. The content of the ion sustained-release glass (a) is preferably greater than or equal to 5% by weight and more preferably in the range of 10% to 40% by weight, with respect to the total amount of the thermoplastic sheet composition. In the case where the content of the ion sustained-release glass (a) is less than 10% by weight, the amount of ion sustained-released from the thermoplastic sheet composition is small, and the acid neutralizing capacity and tooth substance strengthening effects might be insufficient. In the case where the content of the ion sustained-release glass (a) exceeds 40% by weight, a problem of molding difficulty arises.

The thermoplastic sheet composition according to the present invention may contain water or a hydrophilic compound, in order to promote the sustained release of ion. The water or the hydrophilic compound may be the same as the water or the hydrophilic compound usable in the dental varnish composition.

The thermoplastic sheet composition according to the present invention may contain a coloring agent. The coloring agent may be the same as the coloring agent usable in the dental varnish composition.

The thermoplastic sheet composition according to the present invention may contain a viscosity modifier to uniformly disperse the ion sustained-release glass in the thermoplastic sheet composition. The viscosity modifier may be the same as the viscosity modifier usable in the dental varnish composition.

The thermoplastic sheet composition according to the present invention may contain a fluoride ion supply material. The fluoride ion supply material may be the same as the fluoride ion supply material usable in the neutralization promoting ion sustained-release dental film.

The thermoplastic sheet composition according to the present invention may contain a saliva secretion promoter. The saliva secretion promoter may be the same as the saliva secretion promoter usable in the neutralization promoting ion sustained-release dental film.

The thermoplastic sheet composition according to the present invention may contain a saliva buffering capacity improver. The saliva buffering capacity improver may be the same as the saliva buffering capacity improver usable in the neutralization promoting ion sustained-release dental film.

The thermoplastic sheet composition according to the present invention may contain an antibacterial agent. The antibacterial agent may be the same as the antibacterial agent usable in the neutralization promoting ion sustained-release dental film.

The manufacturing method of the thermoplastic sheet composition according to the present invention is not particularly limited, though the following method is preferable as an example.

The ion sustained-release glass and the resin are mixed by a pressure kneader in the presence of heat, and then molded in sheet form to obtain the thermoplastic sheet composition.

[Two-Component Mixture Ion Sustained-Release Denture Base-Related Material Composition]

The dental composition according to the present invention is suitable for use as a two-component mixture ion sustained-release denture base-related material composition composed of a powder material and a liquid material, in the case where the carrier (b) is the noncrosslinked (meth)acrylate polymer (k).

A complete denture and a partial denture which are each a prosthetic device worn by a patient with missing teeth are each separated into a part corresponding to the teeth, called artificial teeth, and a part corresponding to the gingiva, called a denture base. The denture base is composed of a denture base resin that occupies most of the denture base, and a lining material that lines the mucosal surface of the denture base whose compatibility with the residual ridge has degraded or a quick cure resin for repairing the denture base. As a denture base-related material used not in combination with artificial teeth, a base orthodontic resin for making a retainer which is attached to the palatine portion so that the straightened teeth do not return to the original position is known, too. Various materials are used for such denture base-related materials by corresponding use methods.

The denture base resin is an acrylic resin, a polycarbonate resin, a polyester resin, or the like, and dentists select and use any of such resins depending on cases and the like. Of these, the acrylic resin is most frequently used for its chemical adhesion to artificial teeth. The denture base resin made of the acrylic resin is composed of a powder material containing a noncrosslinked (meth)acrylate polymer as a main component and a liquid material containing a monofunctional (meth)acrylate polymerizable monomer as a main component. The powder material and the liquid material are mixed and swollen to change into a state called a rice cake-like resin, and then packed into a mold in which the artificial teeth are arranged and heated and pressurized so as to be polymerized and hardened, thus forming the denture.

The denture base lining material made of the acrylic resin is composed of a powder material containing a noncrosslinked (meth)acrylate polymer as a main component and a liquid material containing a monofunctional (meth)acrylate polymerizable monomer as a main component, like the denture base resin. The following method is commonly used. The powder material and the liquid material are mixed and, while it still has fluidity, poured onto the mucosal surface of the denture base. After the denture is attached into the oral cavity and held for a predetermined time, the denture is taken out of the oral cavity and, following trimming of excess portions, hardened to line the denture base. While the polymerization and hardening of the lining material progress at ambient temperature after the powder material and the liquid material are mixed, a method of immersion in a hardening promoter aqueous solution of 50° C. to 60° C., i.e. warm water in which a chemical polymerization catalyst is dissolved, for final hardening is also used.

The quick cure resin made of the acrylic resin is composed of a powder material containing a noncrosslinked (meth)acrylate polymer as a main component and a liquid material containing a monofunctional (meth)acrylate polymerizable monomer as a main component, like the denture base resin. The denture base is typically repaired using the quick cure resin by a technique called brush-on. In this method, a process of applying the liquid material to the repair part of the denture base using a brush, collecting an appropriate amount of the powder material with the tip of the brush soaked again with the liquid material, and placing the mixture formed at the tip of the brush on the repair part is repeatedly performed. The polymerization and hardening of the quick cure resin progress at ambient temperature as the powder material and the liquid material are mixed.

The base orthodontic resin made of the acrylic resin is composed of a powder material containing a (meth)acrylate polymer as a main component and a liquid material containing a monofunctional (meth)acrylate polymerizable monomer as a main component, like the denture base resin. When making the retainer, a method called sprinkling whereby a predetermined amount of the powder material is sprinkled onto a palatine portion gypsum model and then the liquid material is dropped from above is often used. While the polymerization and hardening of the base orthodontic resin progress at ambient temperature as the liquid material is sprinkled over the powder material, a method of heating and pressurizing in warm water of 50° C. to 60° C. for final hardening is typically used.

The conventional denture base-related material is mainly composed of a noncrosslinked (meth)acrylate polymer, and so is known to have a problem with machinability upon form correction as the hardened material is low in hardness. For example, if the machinability is poor when correcting the form after making the denture, a part of the denture base-related material sticks to the rotating portion of the grinder, which causes poor workability. Besides, there are cases in which the denture is deformed by frictional heat as a result of grinding or polishing for a long time. Thus, a decrease in function of the denture such as the compatibility with the oral mucosa can ensue. Moreover, in the case where the denture is dropped by mistake, the denture is easily flawed if the surface hardness is low. This not only has a possibility of leading to the breakage of the denture, but also decreases the esthetics due to the flaw. In the case where the denture has many flaws on its surface, stains such as plaque tend to adhere, and bacteria, fungi, and the like grow. This poses a serious problem in terms of hygiene, too.

In the case of the partial denture, the denture is fixed by clasping a remaining tooth called an abutment tooth. However, the abutment tooth is difficult to be cleaned, and also becomes unclean due to the presence of the denture. There is thus a problem in that dental caries develop easily.

JP 4562819 B discloses a coating material composition having excellent surface hardness for coating the surface of a dental curable composition that is made up of di(meth)acrylate having a urethane bond in a molecule, di(meth)acrylate having an oxyethylene unit in a molecule, a volatile compound, and α-ketocarbonyl compound and has a partial oxide of tri-n-butyl boron compound as a polymerization initiator. However, coating the denture surface does not improve the machinability and the denture deformation, though the problem of flaw susceptibility is improved. Besides, a problem of requiring an additional operation step, i.e. coating, arises.

A fluorine sustained-release material as represented by glass ionomer cement is known to have a feature of continuously releasing the fluorine ion though in a small amount and achieve preventive effects such as secondary caries suppression and tooth substance strengthening.

JP 3452613 B discloses a dental resin composition that has fluorine sustained releasability by containing a fluorine-containing cyclic phosphazene compound or a polymer or copolymer with the compound as the repeat unit and is usable for a partial denture or a lining material. Although this patent has a feature of providing fluorine sustained releasability by including the phosphazene compound which is an organic component in the dental composition, the machinability and the surface hardness are unchanged from conventional denture base-related materials, and the problem of flaw susceptibility remains unsolved. There are thus a problem of a decrease in esthetics and a hygienic problem caused by the adhesion of plaque and the like to flaws.

JP 5443688 B discloses a dental fluoride ion sustained-release composition that includes a metal fluoride, a fluorine-containing phosphazene monomer, or the like in addition to an inorganic powder, a polymerizable monomer, and a polymerization initiator and is usable for a dental adhesive material, a dental filling material, a dental coating material, etc.

Although this patent has a feature of providing fluorine sustained releasability by including the metal fluoride, the fluorine-containing phosphazene monomer, or the like in the dental composition, the effects of improving the machinability and the surface hardness are insufficient, and the problem of flaw susceptibility remains unsolved. There are thus a problem of a decrease in esthetics and a hygienic problem caused by the adhesion of plaque and the like to flaws, as with the conventional denture base-related material.

JP H09-315922 A discloses a dental composition or the like having fluorine sustained releasability by containing a fluorinated aromatic compound such as fluorinated pitch.

Although this patent has a feature of providing fluorine sustained releasability by including the fluorinated aromatic compound which is an organic component in the dental composition, the fluorine sustained releasability is poor. Besides, the machinability and the surface hardness are unchanged from conventional denture base-related materials, and the problem of flaw susceptibility remains unsolved.

There are thus a problem of a decrease in esthetics and a hygienic problem caused by the adhesion of plaque and the like to flaws.

JP 4673310 B discloses a polymerizable composition for coating a tooth surface or a dental prosthetic that suppresses the adhesion of plaque and the like by including a chain compound having a fluoroalkyl group at both ends, a polymerizable monomer, and a polymerization initiator. Although this patent can suppress the adhesion of plaque by including the chain compound having the fluoroalkyl group at both ends in the dental composition, the machinability and the surface hardness are unchanged from conventional denture base-related materials, and the problem of flaw susceptibility remains unsolved. There are thus a problem of a decrease in esthetics and a hygienic problem caused by the adhesion of plaque and the like to flaws.

This raises the need for a dental denture base-related material that has high material hardness after hardening and favorable machinability upon form correction, is resistant to stains such as plaque on its surface, suppresses the growth of bacteria, fungi, and the like, and has preventive functions with sustained releasability of various ions including the fluoride ion. The present invention accordingly has an object of providing a dental denture base-related material that has: excellent machinability; high surface hardness; and ion sustained releasability of various ions including the fluoride ion capable of suppressing decalcification of an abutment tooth which tends to become unclean when a partial denture is used.

As a result of conducting intensive study to overcome the problems stated above, the inventors have solved the problems by providing a two-component mixture ion sustained-release denture base-related material composition including a noncrosslinked (meth)acrylate polymer, ion sustained-release glass, a monofunctional (meth)acrylate polymerizable monomer, and a polymerization initiator. Note that the entire disclosure of each of the above-mentioned documents is incorporated in this specification by reference.

The two-component mixture ion sustained-release denture base-related material composition according to the present invention produces the following various effects. The two-component mixture ion sustained-release denture base-related material composition according to the present invention is composed of a powder material including a noncrosslinked (meth)acrylate polymer and ion sustained-release glass and a liquid material including a monofunctional (meth)acrylate polymerizable monomer, and includes a polymerization initiator in at least one of the powder material and the liquid material. Such a two-component mixture ion sustained-release denture base-related material composition exhibits favorable machinability upon form correction and high surface hardness after hardening. The favorable machinability not only contributes to excellent workability, but also shortens the grinding or polishing time and thus reduces the thermal deformation of the denture. As a result, the denture having excellent compatibility with the oral mucosa can be provided. Moreover, the improved surface hardness of the hardened material prevents flaws on the surface and suppresses the growth of bacteria, fungi, and the like, so that the denture excellent in esthetics and hygiene can be provided. In addition, the inclusion of the ion sustained-release glass realizes a rechargeable denture base-related material composition that can not only continuously sustained-release ions such as the fluoride ion but also take in various ions from outside and sustained-release the ions again. Therefore, in addition to suppressing decalcification of an abutment tooth which tends to become unclean especially when a partial denture is used, the two-component mixture ion sustained-release denture base-related material composition according to the present invention has excellent effects for healthy oral cavity environment as it influences the strengthening of the tooth substance, the suppression of secondary caries, the suppression of decalcification, the recalcification, the suppression of bacterial activity, the prevention of periodontal disease, and the like in the surrounding part.

The two-component mixture ion sustained-release denture base-related material composition includes: a powder material including the dental composition according to the present invention in which the carrier (b) is the noncrosslinked (meth)acrylate polymer (k); and a liquid material including the monofunctional (meth)acrylate polymerizable monomer (l), wherein at least one of the powder material and the liquid material includes the polymerization initiator (m).

—Noncrosslinked (Meth)Acrylate Polymer (k)

The noncrosslinked (meth)acrylate polymer (k) usable in the two-component mixture ion sustained-release denture base-related material composition according to the present invention is not particularly limited so long as it swells by the monofunctional (meth)acrylate polymerizable monomer. A polymer formed by homopolymerization of a monofunctional (meth)acrylate polymerizable monomer, a polymer formed by copolymerization of several types of monofunctional (meth)acrylate polymerizable monomers, a polymer formed by copolymerization of a monofunctional (meth)acrylate polymerizable monomer with another monofunctional polymerizable monomer, or the like can be used without any limitation. Specific examples of the noncrosslinked (meth)acrylate polymer include: homopolymers such as polymethyl (meth)acrylate, polyethyl (meth)acrylate, polypropyl (meth)acrylate, polyisopropyl (meth)acrylate, polyisobutyl (meth)acrylate, and polybutyl (meth)acrylate; and copolymers that each combine two or more types from among methyl (meth)acrylate, ethyl (meth)acrylate, propyl (meth)acrylate, isopropyl (meth)acrylate, isobutyl (meth)acrylate, butyl (meth)acrylate, 2-ethyhexyl (meth)acrylate, and the like, though the noncrosslinked (meth)acrylate polymer is not limited to such. These noncrosslinked (meth)acrylate polymers may be used singly or in combination.

Of these noncrosslinked (meth)acrylate polymers, polymethyl methacrylate, polyethyl methacrylate, or a copolymer of methyl methacrylate and ethyl methacrylate is preferably used.

The polymerization method for such a noncrosslinked (meth)acrylate polymer is not limited. Any polymerization method such as emulsion polymerization, suspension polymerization, or the like is applicable. The shape of the noncrosslinked (meth)acrylate polymer is not limited, and may be any of spherical, crushed, and hollow. A preferable shape is spherical. The average particle diameter (50%) of the noncrosslinked (meth)acrylate polymer is not limited so long as it is in the range of 1 µm to 300 µm. A preferable range is 1 µm to 200 µm, and a more preferable range is 5 µm to 150 µm. The weight-average molecular weight of the noncrosslinked (meth)acrylate polymer is not limited so long as it is in the range of 100000 to 2000000. A preferable range is 300000 to 1700000, and a more preferable range is 500000 to 1500000.

A material obtained by a secondary treatment such as composite treatment or surface modification treatment, e.g. coating the surface of an organic filler, an inorganic filler, an organic-inorganic composite filler, an organic-inorganic compound, an organic-inorganic pigment, or the like with the noncrosslinked (meth)acrylate polymer, may also be used without limitation.

The content of the noncrosslinked (meth)acrylate polymer in the two-component mixture ion sustained-release denture base-related material composition according to the present invention is not limited so long as it is in the range of 10% to 80% by weight. A preferable range is 20% to 80% by weight, and a more preferable range is 30% to 70% by weight. In the case where the content of the noncrosslinked (meth)acrylate polymer is less than 10% by weight, the monofunctional (meth)acrylate polymerizable monomer is excessive and the polymerization shrinkage of the resin component is significant, causing a problem such as a decrease in dimensional accuracy, e.g. compatibility, of the denture base. In the case where the content of the noncrosslinked (meth)acrylate polymer exceeds 80% by weight, the noncrosslinked (meth)acrylate polymer is excessive and hardening is not uniform, causing a problem such as a decrease in material strength.

The two-component mixture ion sustained-release denture base-related material composition according to the present invention includes the ion sustained-release glass (a), wherein ions resulting from the glass composition are continuously sustained-released from the glass.

The content of the ion sustained-release glass (a) is preferably in the range of 1% to 60% by weight and more preferably in the range of 3% to 60% by weight, with respect to the total amount of the two-component mixture ion sustained-release denture base-related material composition. In the case where the content of the ion sustained-release glass (a) is less than 1% by weight, the amount of sustained-released ion is insufficient, and the tooth substance strengthening effect, the secondary caries suppression effect, and the like cannot be expected. In the case where the content of the ion sustained-release glass (a) exceeds 60% by weight, the viscosity of the two-component mixture ion sustained-release denture base-related material composition is high and a problem such as a decrease in operability arises.

—Monofunctional (Meth)Acrylate Polymerizable Monomer (l)

The monofunctional (meth)acrylate polymerizable monomer (l) usable in the two-component mixture ion sustained-release denture base-related material composition according to the present invention may be any (meth)acrylate polymerizable monomer having a well-known monofunctional acrylate group and/or methacrylate group typically used in the dental field, without limitation. The monofunctional (meth)acrylate polymerizable monomer in the present invention inclusively means both an acryloyl group-containing polymerizable monomer and a methacryloyl group-containing polymerizable monomer.

Specific examples of the monofunctional (meth)acrylate polymerizable monomer (l) include: (meth)acrylic esters such as methyl (meth)acrylate, ethyl (meth)acrylate, butyl (meth)acrylate, hexyl (meth)acrylate, glycidyl (meth)acrylate, lauryl (meth)acrylate, cyclohexyl (meth)acrylate, benzyl (meth)acrylate, allyl (meth)acrylate, 2-ethoxyethyl (meth)acrylate, glycerol (meth)acrylate, isobonyl (meth)acrylate, 2-hydroxyethyl (meth)acrylate, 2-hydroxypropyl (meth)acrylate, 3-hydroxypropyl (meth)acrylate, 1,2-dihydroxypropyl (meth)acrylate, 1,3-dihydroxypropyl (meth)acrylate, and 2,3-dihydroxypropyl (meth)acrylate; silane compounds such as γ-(meth)acryloyloxypropyltrimethoxysilane and γ-(meth)acryloyloxypropyltriethoxysilane; and nitrogen-containing compounds such as 2-(N,N-dimethylamino)ethyl(meth)acrylate and N-methylol (meth)acrylamide.

The content of the monofunctional (meth)acrylate polymerizable monomer (l) in the two-component mixture ion sustained-release denture base-related material composition according to the present invention is not limited so long as it is in the range of 20% to 90% by weight. A preferable range is 20% to 60% by weight, and a more preferable range is 20% to 40% by weight. In the case where the content of the monofunctional (meth)acrylate polymerizable monomer is less than 20% by weight, the hardenability of the resin component decreases, causing a problem with the material property of the hardened material. In the case where the content of the monofunctional (meth)acrylate polymerizable monomer exceeds 90% by weight, the polymerization shrinkage of the resin component is significant, causing a problem such as a decrease in dimensional accuracy, e.g. compatibility, of the denture base.

—Polymerization Initiator (m)

The polymerization initiator (m) usable in the two-component mixture ion sustained-release denture base-related material composition according to the present invention is not particularly limited, and may be any well-known radical generator used in the dental field. Typically, polymerization initiators (m) are mainly classified into a type (chemical polymerization initiator) that initiates polymerization by mixture, a type (thermal polymerization initiator) that initiates polymerization by heating, and a type (photopolymerization initiator) that initiates polymerization by light irradiation, and any of the polymerization initiators may be used in the present invention without limitation. These polymerization initiators may be used singly or in combination, regardless of the polymerization mode or the polymerization method.

Specific examples of the polymerization initiator include: organic peroxides such as benzoyl peroxide, p-chlorobenzoyl peroxide, 2,4-dichlorobenzoyl peroxide, acetyl peroxide, lauroyl peroxide, tertiary butyl peroxide, cumene hydroperoxide, 2,5-dimethyl-2,5-di(benzoylperoxy)hexane, 2,5-dihydroperoxide, methyl ethyl ketone peroxide, and tertiary butyl peroxybenzoate; and azo compounds such as azobisisobutyronitrile, azobisisobutyric acid methyl, and azobiscyanovaleric acid. Of these, an organic peroxide is preferable, and benzoyl peroxide is more preferable. Such a polymerization initiator is also used in the manufacturing stage of the noncrosslinked (meth)acrylate polymer which is the component (k), and the remaining polymerization initiator may be used as the polymerization initiator (m) in the two-component mixture ion sustained-release denture base-related material composition according to the present invention. In other words, in the case where the polymerization initiator used in the manufacturing stage of the noncrosslinked (meth)acrylate polymer remains in the noncrosslinked (meth)acrylate polymer, the polymerization initiator need not be added to the powder material of the two-component mixture ion sustained-release denture base-related material composition according to the present invention.

These polymerization initiators may be used singly or in combination, regardless of the polymerization method. The polymerization initiator may be subject to a secondary treatment such as microencapsulation, to stabilize polymerization or delay polymerization.

The photopolymerization initiator may be a photosensitizer, a photosensitizer/photopolymerization promoter, or the like, though not limited to such.

Specific examples of the photosensitizer include: α-diketones such as benzyl, camphorquinone, α-naphthyl, acetonaphthone, p,p'-dimethoxybenzyl, p,p'-dichlorobenzylacetyl, pentanedione, 1,2-phenanthrenequinone, 1,4-phenanthrenequinone, 3,4-phenanthrenequinone, 9,10-phenanthrenequinone, and naphthoquinone; benzoin alkylethers such as benzoin, benzoin methyl ether, and benzoin ethyl ether; thioxanthones such as thioxanthone, 2-chlorothioxanthone, 2-methylthioxanthone, 2-isopropylthioxanthone, 2-methoxythioxanthone, 2-hydroxythioxanthone, 2,4-diethylthioxanthone, and 2,4-diisopropylthioxanthone; benzophenones such as benzophenone, p-chlorobenzophenone, and p-methoxybenzophenone; acylphosphine oxides such as 2,4,6-trimethylbenzoyl-diphenylphosphine oxide, and bis(2,6-dimethoxybenzoyl)-2,4,4-trimethylpentylphosphine oxide; α-aminoacetophenones such as 2-benzyl-dimethylamino-1-(4-morpholinophenyl)-butanone-1 and 2-benzyl-diethylamino-1-(4-morpholinophenyl)-propanone-1; ketals such as benzyl dimethyl ketal, benzyl diethyl ketal, and benzyl(2-methoxyethyl ketal); and titanocenes such as bis(cyclopentadienyl)-bis[2,6-difluoro-3-(1-pyrrolyl)phenyl]-titanium, bis(cycpentadienyl)-bis(pentafluorophenyl)-titanium, and bis(cyclopentadienyl)-bis(2,3,5,6-tetrafluoro-4-disiloxyphenyl)-titanium.

Specific examples of the photopolymerization promoter include: tertiary amines such as N,N-dimethylaniline, N,N-diethylaniline, N,N-di-n-butylaniline, N,N-dibenzylaniline, p-N,N-dimethyl-toluidine, m-N,N-dimethyl-toluidine, p-N,N-diethyl-toluidine, p-bromo-N,N-dimethylaniline, m-chloro-N,N-dimethylaniline, p-dimethylaminobenzaldehyde, p-dimethylaminoacetophenone, p-dimethylaminobenzoic acid, p-dimethylaminobenzoic acid ethyl ester, p-dimethylaminobenzoic acid amino ester, N,N-dimethylanthranylic acid methyl ester, N,N-dihydroxyethylaniline, p-N,N-dihydroxyethyl-toluidine, p-dimethylaminophenyl alcohol, p-dimethylaminostylene, N,N-dimethyl-3,5-xylidine, 4-dimethylaminopyridine, N,N-dimethyl-α-naphthylamine, N,N-dimethyl-β-naphthylamine, tributylamine, tripropylamine, triethylamine, N-methyldiethanolamine, N-ethyldiethanolamine, N,N-dimethylhexylamine, N,N-dimethyldodecylamine, N,N-dimethylstearylamine, N,N-dimethylaminoethyl methacrylate, N,N-diethylaminoethyl methacrylate, and 2,2'-(n-butylimino)diethanol; secondary amines such as N-phenylglycine; barbituric acids such as 5-butylbarbituric acid, and 1-benzyl-5-phenylbarbituric acid; tin compounds such as dibutyltin diacetate, dibutyltin dilaurate, dioctyltin dilaurate, dioctyltin diverthatate, dioctyltinbis(mercaptoacetic acid isooctyl ester) salt, and tetramethyl-1,3-diacetoxydistannoxane; aldehyde compounds such as lauryl aldehyde and terephthalaldehyde; and sulfur-containing compounds such as dodecyl mercaptan, 2-mercaptobenzoxazole, 1-decanethiol, and thiosalicylic acid.

For improved photopolymerization promoting ability, it is effective to add, in addition to the above-mentioned photopolymerization promoter, oxycarboxylic acids such as citric acid, malic acid, tartaric acid, glycolic acid, gluconic acid, α-oxyisobutyric acid, 2-hydroxypropanoic acid, 3-hydroxypropanoic acid, 3-hydroxybutanoic acid, 4-hydroxybutanoic acid, and dimethylol propionic acid.

These polymerization initiators may be used singly or in combination, regardless of the polymerization method. The polymerization initiator may be subject to a secondary treatment such as microencapsulation, to stabilize polymerization or delay polymerization.

The chemical polymerization initiator may be a redox type polymerization initiator system composed of an organic peroxide/amine compound, an organic peroxide/amine compound/sulfinate, or an organic peroxide/amine compound/borate compound, or an organic metal type polymerization initiator system that reacts with oxygen or water to initiate polymerization. The sulfinate or the borate compound can further initiate polymerization by reacting with a polymerizable monomer having an acidic group, though the present invention is not limited to such.

Specific examples of the organic peroxide include benzoyl peroxide, p-chlorobenzoyl peroxide, 2,4-dichlorobenzoyl peroxide, acetyl peroxide, lauroyl peroxide, tertiary butyl peroxide, cumene hydroperoxide, 2,5-dimethyl-2,5-di(benzoylperoxy)hexane, 2,5-dihydroperoxide, methyl ethyl ketone peroxide, and tertiary butyl peroxybenzoate.

The amine compound is preferably a secondary amine or a tertiary amine in which an amine group is attached to an aryl group, as an example. Specific examples include p-N,N-dimethyl-toluidine, N,N-dimethyl aniline, N-β-hydroxyethyl-aniline, N,N-di(β-hydroxyethyl)-aniline, p-N,N-di(β-hydroxyethyl)-toluidine, N-methyl-aniline, and p-N-methyl-toluidine.

Specific examples of the sulfinate include benzenesulfinic sodium, benzenesulfinic lithium, and p-toluenesulfinic sodium.

Specific examples of the borate compound include sodium salt, lithium salt, potassium salt, magnesium salt, tetrabutylammonium salt, and tetramethylammonium salt of trialkylphenyl boron, trialkyl(p-fluorophenyl) boron (alkyl group is n-butyl group, n-octyl group, n-dodecyl group, etc.), and the like.

Specific examples of the organic metal type polymerization initiator include organic boron compounds such as triphenylborane, tributylborane, and tributylborane partial oxide.

These polymerization initiators may be used singly or in combination, regardless of the polymerization method. The polymerization initiator may be subject to a secondary treatment such as microencapsulation, to stabilize polymerization or delay polymerization.

In a denture base material other than a thermal polymerization type denture base resin hardened by thermal polymerization, the chemical polymerization initiator that initiates polymerization by mixture immediately before use is preferably used from among these polymerization initiators. The use of the chemical polymerization initiator is most desirable for its simplicity. Of the chemical polymerization initiators, a combination of an organic peroxide and a tertiary amine is more preferable, and a combination of benzoyl peroxide and a tertiary amine such as p-N,N-dimethyl-toluidine or p-N,N-di(β-hydroxyethyl)-toluidine is most preferable.

The content of the polymerization initiator (m) in the two-component mixture ion sustained-release denture base-related material composition according to the present invention can be selected as appropriate depending on use. A preferable range is 0.1% to 5% by weight and a more preferable range is 0.1% to 2% by weight, with respect to 100% by weight the total polymerizable monomer. In the case where the content of the polymerization initiator (m) is less than 0.1% by weight, the polymerization hardenability is insufficient, and the desired material property or performance cannot be achieved. In the case where the content of the polymerization initiator (m) exceeds 5% by weight, the polymerization hardening accelerates, which causes a problem with operability such as reduced operation time. Besides, rapid polymerization induces a larger residual stress, leading to a problem with dimensional stability such as the produced denture being deformed.

A multifunctional (meth)acrylate polymerizable monomer usable in the two-component mixture ion sustained-release denture base-related material composition according to the present invention may be any (meth)acrylate polymerizable monomer having a well-known multifunctional acrylate group and/or methacrylate group typically used in the dental field, without limitation. The multifunctional (meth)acrylate polymerizable monomer in the present invention inclusively means both an acryloyl group-containing polymerizable monomer and a methacryloyl group-containing polymerizable monomer.

Specific examples of the multifunctional (meth)acrylate polymerizable monomer are as follows.

Examples of an aromatic bifunctional (meth)acrylate polymerizable monomer include 2,2-bis(4-(meth)acryloyloxyphenyl)propane, 2,2-bis(4-(meth)acryloyloxyethoxyphenyl)propane, 2,2-bis(4-(meth)acryloyloxydiethoxyphenyl)propane, 2,2-bis(4-(meth)acryloyloxytetraethoxyphenyl)propane, 2,2-bis(4-(meth)acryloyloxypentaethoxyphenyl)propane, 2,2-bis(4-(meth)acryloyloxydipropoxyphenyl)propane, 2(4-(meth)acryloyloxyethoxyphenyl)-2(4-(meth)acryloyloxydiethoxyphenyl) propane, 2(4-(meth)acryloyloxydiethoxyphenyl)-2(4-(meth)acryloyloxytriethoxyphenyl) propane, 2(4-(meth)acryloyloxydipropoxyphenyl)-2(4-(meth)acryloyloxytriethoxyphenyl)propane, 2,2-bis(4-(meth)acryloyloxydipropoxyphenyl)propane, and 2,2-bis(4-(meth)acryloyloxyisopropoxyphenyl)propane.

Examples of an aliphatic bifunctional (meth)acrylate polymerizable monomer include ethyleneglycoldi(meth)acrylate, diethyleneglycoldi(meth)acrylate, triethyleneglycoldi(meth)acrylate, butyleneglycoldi(meth)acrylate, neopentylglycoldi(meth)acrylate, polyethyleneglycoldi(meth)acrylate, 1,3-butanedioldi(meth)acrylate, 1,4-butanedioldi(meth)acrylate, 1,6-hexanedioldi(meth)acrylate, 2-hydroxypropyl-1,3-di(meth)acrylate, 3-hydroxypropyl-1,2-di(meth)acrylate, pentaerythritoldi(meth)acrylate, 2-trimethylammoniumethyl(meth)acrylchloride, (meth)acrylamide, 2-hydroxyethyl(meth)acrylamide, and polyethyleneglycoldi(meth)acrylate (the number of oxyethylene groups is not less than 9).

Examples of a trifunctional (meth)acrylate polymerizable monomer include trimethylolpropanetri(meth)acrylate, trimethylolethanetri(meth)acrylate, trimethylolmethanetri(meth)acrylate, and pentaerythiritoltri(meth)acrylate.

Examples of a tetrafunctional (meth)acrylate polymerizable monomer include pentaerythritoltetra(meth)acrylate and ditrimethylolpropanetetra(meth)acrylate.

Examples of an urethane (meth)acrylate polymerizable monomer include di(meth)acrylate having bifunctional, trifunctional, or higher-functional urethane bond guided from an adduct of a polymerizable monomer having a hydroxyl group such as 2-hydroxyethyl(meth)acrylate, 2-hydroxypropyl(meth)acrylate, or 3-chloro-2-hydroxypropyl(meth)acrylate and a diisocyanate compound such as methylcyclohexanediisocyanate, methylenebis(4-cyclohexylisocyanate), hexamethylenediisocyanate, trimethylhexamethylenediisocyanate, isophoronediisocyanate, diisocyanatemethylmethylbenzene, or 4,4-diphenylmethanediisocyanate.

The content of the multifunctional (meth)acrylate polymerizable monomer in the two-component mixture ion sustained-release denture base-related material composition according to the present invention is not limited so long as it is in the range of 1% to 60% by weight. A preferable range is 1% to 50% by weight, and a more preferable range is 1% to 30% by weight. In the case where the content of the multifunctional (meth)acrylate polymerizable monomer is less than 1% by weight, the effect of adding the multifunctional (meth)acrylate polymerizable monomer cannot be attained as the crosslink density of the resin component is low. In the case where the content of the multifunctional (meth)acrylate polymerizable monomer exceeds 60% by weight, the amount of addition is excessive and the polymerization shrinkage of the resin component is significant, causing a problem such as deformation in denture production.

The organic solvent usable in the two-component mixture ion sustained-release denture base-related material composition according to the present invention is not particularly limited, and may be any well-known organic solvent. Specific examples of the organic solvent include: alcohols such as methanol, ethanol, isopropyl alcohol, and isobutyl alcohol; ketones such as methyl ethyl ketone and acetone; and alkyl halides such as dichloromethane, chloroform, and carbon tetrachloride, though the organic solvent is not limited to such. These organic solvents may be used singly or in combination. Of the organic solvents, alcohols are preferable, and ethanol, isopropyl alcohol, etc. are more preferable.

The content of the organic solvent in the two-component mixture ion sustained-release denture base-related material composition according to the present invention can be adjusted as appropriate depending on the use method, the purpose of use, the composition, etc. The content of the organic solvent is not limited so long as it is in the range of 0.1% to 30% by weight. A preferable range is 0.1% to 10% by weight, and a more preferable range is 0.1% to 5% by weight. In the case where the content of the organic solvent is less than 0.1% by weight, the swelling property and the like are the same as in the case where the organic solvent is not included, and the effect of adding the organic solvent cannot be attained. In the case where the content of the organic solvent exceeds 30% by weight, a problem with the material property such as a decrease in strength of the hardened material arises.

The filling material usable in the two-component mixture ion sustained-release denture base-related material composition according to the present invention is not particularly limited, and may be any of an organic component, an inorganic component, and their mixture or compound so long as it does not swell by the monofunctional (meth)acrylate polymerizable monomer.

Specific examples of the filling material include: metal hydroxides such as aluminum hydroxide, calcium hydroxide, and magnesium hydroxide; carbonates such as calcium carbonate and strontium carbonate; metal oxides such as aluminum oxide; metal fluorides such as barium fluoride, calcium fluoride, and strontium fluoride; inorganic filling materials such as talc, kaolin, clay, mica, hydroxyapatite, silica, and quartz; elastomers such as polyvinyl acetate, polyvinyl alcohol, and styrene-butadiene rubber; organic filling materials such as a crosslinked (meth)acrylate polymer formed by copolymerizing a monofunctional (meth)acrylate polymerizable monomer and a polymerizable monomer having two or more functional groups; and organic-inorganic composite filling materials such as a filling material obtained by polymerized-coating the surface of an inorganic filling material with a polymerizable monomer, a filling material obtained by mixing and polymerizing an inorganic filling material and a polymerizable monomer and grinding the result into an appropriate particle diameter, and a filling material obtained by dispersing a filling material in a polymerizable monomer beforehand and subjecting it to emulsion polymerization or suspension polymerization, though the filling material is not limited to such.

These filling materials may be used singly or in combination.

The filling material may have any shape such as spherical, acicular, platy, crushed, or scaly. The average particle diameter (50%) of the filling material is not particularly limited so long as it is in the range of 0.1 μm to 100 μm. A preferable range is 1 μm to 50 μm, and a more preferable range is 1 μm to 10 μM.

The surface of the filling material may be made multifunctional by a surface treatment using a surface treatment agent or the like. The surface-treated filling material may be used without limitation. Specific examples of the surface treatment agent used to make the surface of the filling material multifunctional include a surface active agent, a fatty acid, an organic acid, an inorganic acid, each type of coupling material, and a metal alkoxide compound. Specific examples of the surface treatment method include a method of spraying the surface treatment agent from above in a state where the filling material is fluid, a method of dispersing the filling material in a solution including the surface treatment agent, and a method of forming multiple layers of several types of surface treatment agent on the surface of the filling material. The surface treatment agent and the surface treatment method are, however, not limited to such. These surface treatment agents or surface treatment methods may be used singly or in combination.

The content of the filling material in the two-component mixture ion sustained-release denture base-related material composition according to the present invention is not particularly limited. The content of the filling material is preferably in the range of 1% to 50% by weight and more preferably in the range of 1% to 20% by weight, with respect to the total amount of the two-component mixture ion sustained-release denture base-related material composition. In the case where the content of the filling material is less than 1% by weight, the effect of adding the filling material cannot be attained, and the surface hardness and the machinability are hardly improved. In the case where the content of the filling material exceeds 50% by weight, the content of the noncrosslinked (meth)acrylate polymer in the two-component mixture ion sustained-release denture base-related material composition is low, and the monofunctional (meth) acrylate polymerizable monomer and the like do not penetrate and swell uniformly. As a result, a problem with the material property arises. Besides, the transparency of the hardened material decreases, which leads to an esthetic problem.

The manufacturing method of the two-component mixture ion sustained-release denture base-related material composition according to the present invention is not particularly limited, though the following method is preferable as an example. The ion sustained-release glass and the polymerization initiator are dispersed in the noncrosslinked (meth)acrylate polymer to obtain the powder material. Further, the monofunctional (meth)acrylate polymerizable monomer is mixed with the multifunctional (meth)acrylate polymerizable monomer to obtain the liquid material.

In addition to the components described above, the following components may be optionally added to the two-component mixture ion sustained-release denture base-related material composition according to the present invention depending on need: a vehicle such as fumed silica, an ultraviolet absorber such as 2-hydroxy-4-methylbenzophenone, a polymerization inhibitor such as hydroquinone, hydroquinone monomethyl ether, or 2,5-ditertiary butyl-4-methylphenol, an antitarnish agent, an antimicrobial, a color pigment, and other conventionally known additives.

[Two-Component Mixture Ion Sustained-Release Mucosa Modifier Composition]

The dental composition according to the present invention is suitable for use as a two-component mixture ion sustained-release mucosa modifier composition composed of a powder material and a liquid material, in the case where the carrier (b) is the noncrosslinked (meth)acrylate polymer (k). In this case, the two-component mixture ion sustained-release mucosa modifier composition includes: a powder material including the dental composition according to the present invention in which the carrier (b) is the noncrosslinked (meth)acrylate polymer (k); and a liquid material including the plasticizer (n) and the organic solvent (g).

Since the above-mentioned denture is formed in accordance with the patient's mucosal surface, the denture fits well to the patient's mucosa at the start of use, and normally exhibits the effects of recovering functions such as mastication, swallowing, and pronunciation without any trouble. If the denture is continuously used for a long time, however, the compatibility with the denture base may degrade due to absorption by the patient's alveolar ridge and the like.

In the case where the compatibility between the mucosal surface and the denture base degrades, the denture strongly touches some part, which can cause reddening and swelling of the oral mucosa. In such a case, the denture base needs to be remade. A commonly employed technique is to restore the mucosal surface from reddening and swelling while reducing the burden on the patient, in a state where a soft material called a mucosa modifier is applied to the denture base. After this, a technique called lining or backing is used to remake the denture base to be more compatible with the patient's mucosal surface by replacing the mucosa modifier with a hardening material called a denture base lining material.

Such a mucosa modifier is composed of a powder material containing a noncrosslinked (meth)acrylate polymer as a main component and a liquid material containing a plasticizer and an organic solvent such as ethanol as main components. The following method is commonly used. The powder material and the liquid material are mixed and, while it still has fluidity, piled up on the mucosal surface of the denture base. Once the fluidity has decreased, the denture is attached into the oral cavity and held for a predetermined time, and then the denture is taken out of the oral cavity and trimming of excess portions is performed.

The conventional dental mucosa modifier composition is mainly composed of a noncrosslinked (meth)acrylate polymer and a plasticizer, and so is known to not only have poor operability as the powder material and the liquid material do not mix well with each other but also have a problem with applicability to the denture base and machinability upon form correction as the composition remains very soft even in a mixed and swollen state. For example, if the machinability is poor when correcting the form during mucosa modification, a part of the dental mucosa modifier composition sticks to the rotating portion of the grinder, which causes poor workability. Besides, since the conventional mucosa modifier is not hardenable, stains such as plaque tend to adhere to the mucosal surface, and bacteria, fungi, and the like grow. This poses a serious problem in terms of hygiene, too.

In the case of the partial denture, the denture is conventionally fixed by clasping a remaining tooth called an abutment tooth. However, the abutment tooth is difficult to be cleaned, and also becomes unclean due to the presence of the denture. There is thus a problem in that dental caries develop easily.

The mucosa modifier thus has many problems in the use method and the harsh environment in the oral cavity. As a conventional technique to solve these problems, a method of improving a material for coating the mucosa modifier or the entire denture including the mucosa modifier has been proposed. An example of such a technique is an invention of including, in the mucosa modifier or the coating material, a component resistant to stains, a component for improving the machinability, or a component for sustained-releasing ions such as fluorine.

JP 4673310 B discloses a polymerizable composition for coating a tooth surface or a dental prosthetic that suppresses the adhesion of plaque and the like by including a chain compound having a fluoroalkyl group at both ends, a polymerizable monomer, and a polymerization initiator. Although this patent can suppress the adhesion of plaque by including the chain compound having the fluoroalkyl group at both ends in the dental composition, the chain compound is an organic component and the material hardness is not significantly improved, and so the machinability is insufficient and the problem of poor workability remains. The composition also has the demerits of lower operability as the powder material and the liquid material do not mix well, and lower applicability when applying the mixture to the denture base. Besides, the growth of bacteria, fungi, and the like remains unsolved, posing a serious problem in terms of hygiene, too.

JP 4231949 B discloses a dental mucosa modifier that includes organopolysiloxane, organohydrogenpolysiloxane, a silicone resin filling material, and a hydrosilylation catalyst to improve the machinability. Although this patent can improve the machinability by including the silicone resin filling material in the dental mucosa modifier, the silicone resin filling material is an organic component and the material hardness is not significantly improved, and so its effect is insufficient and the problem of poor workability remains. The composition also has the demerits of lower operability as the powder material and the liquid material do not mix well, and lower applicability when applying the mixture to the denture base. Besides, the growth of bacteria, fungi, and the like remains unsolved, posing a serious problem in terms of hygiene, too.

JP 3452613 B discloses a dental resin composition that has fluorine sustained releasability by containing a fluorine-containing cyclic phosphazene compound or a polymer or copolymer with the compound as the repeat unit and is usable for a partial denture or a lining material. Although this patent has a feature of providing fluorine sustained releasability by including the phosphazene compound in the dental composition, the phosphazene compound is an organic component and the machinability and the surface hardness are unchanged from conventional techniques, and so the problem of poor workability remains. The composition also has the demerits of lower operability as the powder material and the liquid material do not mix well, and lower applicability when applying the mixture to the denture base. Besides, the growth of bacteria, fungi, and the like remains unsolved, posing a serious problem in terms of hygiene, too.

This raises the need for a dental mucosa modifier composition that has favorable mixture between a powder material and a liquid material, has favorable workability when applying the mixture which has lost fluidity after mixture and swelling to a denture base and favorable machinability upon form correction, suppresses the growth of bacteria, fungi, and the like, and has preventive functions with sustained releasability of various ions including the fluoride ion. The present invention accordingly has an object of providing a dental mucosa modifier composition that has: excellent mixture between a powder material and a liquid material; excellent applicability and machinability; and ion sustained releasability of various ions including the fluoride ion capable of suppressing decalcification of an abutment tooth which tends to become unclean when a partial denture is used. Note that the entire disclosure of each of the above-mentioned documents is incorporated in this specification by reference.

As a result of conducting intensive study to overcome the problems stated above, the inventors have realized properties suitable for a mucosa modifier and solved the problems by providing a two-component mixture ion sustained-release mucosa modifier composition that includes a noncrosslinked (meth)acrylate polymer and ion sustained-release glass in the powder material of the mucosa modifier and includes a plasticizer and an organic solvent in the liquid material. The present invention is based on these findings.

The two-component mixture ion sustained-release mucosa modifier composition according to the present invention is composed of a powder material including a noncrosslinked (meth)acrylate polymer and ion sustained-release glass and a liquid material including a plasticizer and an organic solvent. Such a two-component mixture ion sustained-release mucosa modifier composition has favorable mixture between the powder material and the liquid material, facilitates the application of the mixture to the denture base, and exhibits favorable machinability upon form correction as the material has proper hardness. The favorable machinability prevents stains such as plaque on the material surface and suppresses the growth of bacteria, fungi, and the like, so that the denture excellent in esthetics and hygiene can be provided. In addition, the inclusion of the ion sustained-release glass realizes a rechargeable mucosa modifier composition that can not only continuously sustained-release ions such as the fluoride ion but also take in various ions from outside and sustained-release the ions again. Therefore, in addition to suppressing decalcification of an abutment tooth which tends to become unclean especially when a partial denture is used, the two-component mixture ion sustained-release mucosa modifier composition according to the present invention has excellent effects for healthy oral cavity environment as it influences the strengthening of the tooth substance, the suppression of secondary caries, the suppression of decalcification, the recalcification, the suppression of bacterial activity, the prevention of periodontal disease, and the like in the surrounding part.

The noncrosslinked (meth)acrylate polymer (k) usable in the two-component mixture ion sustained-release mucosa modifier composition according to the present invention may be the noncrosslinked (meth)acrylate polymer (k) usable in the two-component mixture ion sustained-release denture base-related material composition.

The content of the noncrosslinked (meth)acrylate polymer (k) in the two-component mixture ion sustained-release mucosa modifier composition according to the present invention is not limited so long as it is in the range of 10% to 80% by weight. A preferable range is 20% to 80% by weight, and a more preferable range is 30% to 70% by weight. In the case where the content of the noncrosslinked (meth)acrylate polymer (k) is less than 10% by weight, the plasticizer is excessive and the elasticity cannot be maintained, causing a problem such as a decrease in operability and mucosa modification capacity. In the case where the content of the noncrosslinked (meth)acrylate polymer (k)

exceeds 80% by weight, the noncrosslinked (meth)acrylate polymer (k) is excessive and the mixed and swollen material is too hard, causing a problem such as a decrease in operability.

The content of the ion sustained-release glass (a) is preferably in the range of 1% to 60% by weight and more preferably in the range of 3% to 60% by weight, with respect to the total amount of the two-component mixture ion sustained-release mucosa modifier composition. In the case where the content of the ion sustained-release glass is less than 1% by weight, the amount of sustained-released ion is insufficient, and the tooth substance strengthening effect, the secondary caries suppression effect, and the like cannot be expected. In the case where the content of the ion sustained-release glass exceeds 60% by weight, the viscosity of the two-component mixture ion sustained-release mucosa modifier composition is high and a problem such as a decrease in operability arises.

—Plasticizer (n)

The plasticizer (n) usable in the two-component mixture ion sustained-release mucosa modifier composition according to the present invention is not particularly limited, and may be any well-known plasticizer. Specific examples of the plasticizer include: phthalate esters such as dimethyl phthalate, diethyl phthalate, dibutyl phthalate, diheptyl phthalate, dioctyl phthalate, di-isodecyl phthalate, butyl benzyl phthalate, diisononyl phthalate, ethyl phthalyl ethyl glycolate, and butyl phthalyl butyl glycolate; dibasic acid esters other than phthalic acid, such as dibutyl adipate, dibutyl diglycol adipate, dibutyl sebacate, dioctyl sebacate, dibutyl maleate, and dibutyl fumarate; glycerol esters such as glycerol triacetate; phosphate esters such as tributyl phosphate, trioctyl phosphate, and triphenyl phosphate; and carboxylate esters such as benzyl benzoate, ethyl benzoate, butyl benzoate, and amyl benzoate, though the plasticizer is not limited to such. These plasticizers may be used singly or in combination.

Of these plasticizers, carboxylate esters are preferable, and benzyl benzoate, dibutyl sebacate, dibutyl phthalate, etc. are more preferable.

The content of the plasticizer (n) in the two-component mixture ion sustained-release mucosa modifier composition according to the present invention can be adjusted as appropriate depending on the use method, the purpose of use, the composition, etc. The content of the plasticizer (n) is not limited so long as it is in the range of 1% to 70% by weight. A preferable range is 1% to 60% by weight, and a more preferable range is 20% to 50% by weight. In the case where the content of the plasticizer (n) is less than 1% by weight, the noncrosslinked (meth)acrylate polymer is excessive and the mixed and swollen material is too hard, causing a problem such as a decrease in operability. In the case where the content of the plasticizer (n) exceeds 60% by weight, the plasticizer is excessive and the elasticity cannot be maintained, causing a problem such as a decrease in operability and mucosa modification capacity.

The organic solvent (g) usable in the two-component mixture ion sustained-release mucosa modifier composition according to the present invention is not particularly limited, and may be any well-known organic solvent. Specific examples of the organic solvent (g) include: alcohols such as methanol, ethanol, isopropyl alcohol, and isobutyl alcohol; ketones such as methyl ethyl ketone and acetone; and alkyl halides such as dichloromethane, chloroform, and carbon tetrachloride, though the organic solvent is not limited to such. These organic solvents may be used singly or in combination.

Of the organic solvents, alcohols are preferable, and ethanol, isopropyl alcohol, etc. are more preferable.

The content of the organic solvent (g) in the two-component mixture ion sustained-release mucosa modifier composition according to the present invention can be adjusted as appropriate depending on the use method, the purpose of use, the composition, etc. The content of the organic solvent (g) is not limited so long as it is in the range of 1% to 30% by weight. A preferable range is 1% to 20% by weight, and a more preferable range is 5% to 15% by weight. In the case where the content of the organic solvent (g) is less than 1% by weight, the swelling speed of the noncrosslinked (meth)acrylate polymer and the plasticizer is slow, and the operability as the mucosa modifier decreases. In the case where the content of the organic solvent (g) exceeds 30% by weight, a problem with the material property such as a significant change of the material property caused by the elution of the organic solvent arises.

—Filling Material (o)

The filling material (o) usable in the two-component mixture ion sustained-release mucosa modifier composition according to the present invention is not particularly limited, and may be any of an organic component, an inorganic component, and their mixture or compound so long as it does not swell by the plasticizer and the organic solvent.

Specific examples of the filling material (o) include: metal hydroxides such as aluminum hydroxide, calcium hydroxide, and magnesium hydroxide; carbonates such as calcium carbonate and strontium carbonate; metal oxides such as aluminum oxide; metal fluorides such as barium fluoride, calcium fluoride, and strontium fluoride; inorganic filling materials such as talc, kaolin, clay, mica, hydroxyapatite, silica, and quartz; elastomers such as polyvinyl acetate, polyvinyl alcohol, and styrene-butadiene rubber; organic filling materials such as a crosslinked (meth)acrylate polymer formed by copolymerizing a monofunctional (meth)acrylate polymerizable monomer and a polymerizable monomer having two or more functional groups; and organic-inorganic composite filling materials such as a filling material obtained by polymerized-coating the surface of an inorganic filling material with a polymerizable monomer, a filling material obtained by mixing and polymerizing an inorganic filling material and a polymerizable monomer and grinding the result into an appropriate particle diameter, and a filling material obtained by dispersing a filling material in a polymerizable monomer beforehand and subjecting it to emulsion polymerization or suspension polymerization, though the filling material is not limited to such. These filling materials may be used singly or in combination.

The filling material may have any shape such as spherical, acicular, platy, crushed, or scaly. The average particle diameter (50%) of the filling material is not particularly limited so long as it is in the range of 0.1 µm to 100 µm. A preferable range is 1 µm to 50 µm, and a more preferable range is 1 µm to 10 µm.

The surface of the filling material may be made multifunctional by a surface treatment using a surface treatment agent or the like. The surface-treated filling material may be used without limitation, Specific examples of the surface treatment agent used to make the surface of the filling material multifunctional include a surface active agent, a fatty acid, an organic acid, an inorganic acid, each type of coupling material, and a metal alkoxide compound. Specific examples of the surface treatment method include a method of spraying the surface treatment agent from above in a state where the filling material is fluid, a method of dispersing the filling material in a solution including the surface treatment agent, and a method of forming multiple layers of several types of surface treatment agent on the surface of the filling material. The surface treatment agent and the surface treatment method are, however, not limited to such. These surface treatment agents or surface treatment methods may be used singly or in combination.

The content of the filling material in the two-component mixture ion sustained-release mucosa modifier composition according to the present invention is not particularly limited. The content of the filling material is preferably in the range of 1% to 50% by weight and more preferably in the range of 1% to 20% by weight, with respect to the total amount of the two-component mixture ion sustained-release mucosa modifier composition. In the case where the content of the filling material is less than 1% by weight, the effect of adding the filling material cannot be attained, and the machinability is hardly improved. In the case where the content of the filling material exceeds 50% by weight, the content of the noncrosslinked (meth)acrylate polymer in the two-component mixture ion sustained-release mucosa modifier composition is low, and the monofunctional (meth)acrylate polymerizable monomer and the like do not penetrate and swell uniformly. As a result, a problem with the material property arises.

The manufacturing method of the two-component mixture ion sustained-release mucosa modifier composition according to the present invention is not particularly limited, though the following method is preferable as an example. The ion sustained-release glass is dispersed in the noncrosslinked (meth)acrylate polymer to obtain the powder material. Further, the plasticizer is mixed with the organic solvent to obtain the liquid material.

In addition to the components described above, the following components may be optionally added to the two-component mixture ion sustained-release mucosa modifier composition according to the present invention depending on need: a vehicle such as fumed silica, an ultraviolet absorber such as 2-hydroxy-4-methylbenzophenone, a (meth)acrylate polymerizable monomer, a polymerization initiator, a polymerization inhibitor such as hydroquinone, hydroquinone monomethyl ether, or 2,5-ditertiary butyl-4-methylphenol, an antitarnish agent, an antimicrobial, a color pigment, and other conventionally known additives.

[Dental Resin Temporary Sealing Material Composition]

The dental composition according to the present invention is suitable for use as a polymerizable dental resin temporary sealing material composition that includes the noncrosslinked (meth)acrylate polymer (k), the monofunctional (meth)acrylate polymerizable monomer (l), the hydrophilic polymerizable monomer (p), the polymerization initiator (q), and the plasticizer (n).

A dental resin temporary sealing material is a provisional filling material used to, after removing caries that have occurred in a tooth and forming a cavity, temporarily seal the cavity in dental treatment. Conventional dental resin temporary sealing materials are mainly classified into two types, i.e. photopolymerization type and chemical polymerization type. In current clinical practice, a dentist selects one of the types and uses the selected type depending on the case, the site, the application period, etc. The chemical polymerization type is widely used in terms of cost and ease of filling operation and removal operation. Chemical polymerization type resin temporary sealing materials are, however, defective in sealability. Cases where the tooth substance is decalcified by plaque invasion from the marginal region have been confirmed in actual clinical practice, generating concerns about the occurrence of post-operative pain or secondary caries after prosthesis attachment.

JP 2010-215538 A discloses a resin temporary sealing material that contains rosin or sandarac to improve the adhesion to cavity walls and exhibit excellent sealability. Merely containing rosin or sandarac in the resin temporary sealing material, however, causes a decrease in material property and tends to induce deformation of the hardened material due to mastication, though the adhesion to cavity walls is improved. As a result, a gap occurs in the marginal region, creating a situation where plaque invades and decalcifies the tooth substance easily. Note that the entire disclosure of the above-mentioned document is incorporated in this specification by reference.

There is the need for a resin temporary sealing material that has both excellent sealability of enabling temporary sealing for a predetermined period in a cavity while adhering to cavity walls and excellent removability of enabling easy removal of the temporary sealing material upon removal, and can suppress decalcification of the tooth substance in the cavity by releasing various ions including a fluoride ion.

The dental resin temporary sealing material composition according to the present invention includes the filling material, the hydrophilic polymerizable monomer, and the plasticizer. Hence, the adhesion to cavity walls can be improved and, since there is little dimensional change during hardening, excellent sealability in a cavity can be attained. In addition, the dental resin temporary sealing material composition has proper flexibility and hardness, and so the material deformation can be minimized even under harsh conditions in the mouth. The dental resin temporary sealing material composition thus has excellent retentivity in the cavity, and excellent removability of enabling easy removal of the hardened material. Since the hardened material is flexible, the biting pressure during mastication involving contact with the antagonist can be alleviated to reduce stimulation. Furthermore, in the case where the dental resin temporary sealing material composition contains the ion sustained-release glass, the dental resin temporary sealing material composition has a preventive function such as suppressing decalcification of the tooth substance by releasing various ions including a fluoride ion toward the tooth substance of the cavity walls.

—Noncrosslinked (Meth)Acrylate Polymer (k)

The noncrosslinked (meth)acrylate polymer (k) swells by the monofunctional (meth)acrylate polymerizable monomer (swelling is a phenomenon in that a substance absorbs a solvent and expands. In the dental field, swelling means a sand-like, rice cake-like, or rubber-like thickening behavior as a result of absorption of a monofunctional (meth)acrylate polymerizable monomer into a powder material mainly composed of a (meth)acrylate polymer). As the noncrosslinked (meth)acrylate polymer, a polymer formed by homopolymerization of a (meth)acrylate polymerizable monomer, a polymer formed by copolymerization of a plurality of (meth)acrylate polymerizable monomers, a polymer formed by copolymerization with another polymerizable monomer, or the like can be used without any limitation.

Preferable specific examples of the noncrosslinked (meth)acrylate polymer (k) include: homopolymers such as polymethyl (meth)acrylate, polyethyl (meth)acrylate, polypropyl (meth)acrylate, polyisopropyl (meth)acrylate, polyisobutyl (meth)acrylate, and polybutyl (meth)acrylate; and copolymers that each combine two or more types from among methyl (meth)acrylate, ethyl (meth)acrylate, propyl (meth)acrylate, isopropyl (meth)acrylate, isobutyl (meth)acrylate, butyl (meth)acrylate, and the like. These noncrosslinked (meth)acrylate polymers may be used singly or in combination.

Of these noncrosslinked (meth)acrylate polymers, polymethyl methacrylate, polyethyl methacrylate, or a copolymer of methyl methacrylate and ethyl methacrylate is preferably used.

The polymerization method for such a noncrosslinked (meth)acrylate polymer is not limited. Any polymerization method such as emulsion polymerization, suspension polymerization, or the like is applicable. The shape of the noncrosslinked (meth)acrylate polymer is particulate. Preferable shapes include spherical, crushed, and hollow, without limitation. A particularly preferable shape is spherical. The average particle diameter (50%) of the noncrosslinked (meth)acrylate polymer is not limited so long as it is in the range of 5 μm to 150 μm. A preferable range is 10 μm to 150 μm, and a more preferable range is 20 μm to 140 μm. The weight-average molecular weight of the noncrosslinked (meth)acrylate polymer is not limited so long as it is in the range of 50000 to 1500000. A preferable range is 100000 to 1400000, and a more preferable range is 200000 to 1300000.

The content of the noncrosslinked (meth)acrylate polymer is not limited so long as it is in the range of 44% to 64% by weight. A preferable range is 49% to 64% by weight.

In the case where the content of the noncrosslinked (meth)acrylate polymer is less than 44% by weight, for example, the following problem arises: the monofunctional (meth)acrylate polymerizable monomer or the hydrophilic polymerizable monomer is excessive and penetration and swelling are not uniform, which decreases the flexibility of the hardened material and causes the hardened material to become too hard for removal. In the case where the content of the noncrosslinked (meth)acrylate polymer exceeds 64% by weight, for example, the following problem arises: the noncrosslinked (meth)acrylate polymer is excessive and hardening is not uniform, and so the hardened material cannot be removed at once during removal.

The content of the dental composition according to the present invention in the dental resin temporary sealing material composition according to the present invention is preferably in the range of 3% to 21% by weight and more preferably in the range of 3% to 18% by weight, with respect to the total weight of the dental resin temporary sealing material. In the case where the content of the dental composition is less than 3% by weight, the content of the noncrosslinked (meth)acrylate polymer is high. This accelerates penetration and swelling of the monofunctional (meth)acrylate polymerizable monomer, the hydrophilic polymerizable monomer, and the like, and makes it impossible to ensure a sufficient operation time. Besides, the operability for reproducing the anatomical form during filling to the cavity decreases, and the sealability is adversely affected such as the hardened material being deformed or falling off due to mastication or the like. In the case where the content of the dental composition exceeds 21% by weight, the content of the noncrosslinked (meth)acrylate polymer in the dental resin temporary sealing material is low. This hinders uniform penetration and swelling of the monofunctional (meth)acrylate polymerizable monomer, the hydrophilic polymerizable monomer, and the like, leading to problems in material property, sealability, removability, etc.

—Monofunctional (Meth)Acrylate Polymerizable Monomer (l)

The monofunctional (meth)acrylate polymerizable monomer (l) may be any (meth)acrylate polymerizable monomer having a well-known monofunctional acryloyl group and/or methacryloyl group typically used in the dental field, so long as it is other than the hydrophilic polymerizable monomer (p). The monofunctional (meth)acrylate polymerizable monomer in the present invention inclusively means both an acryloyl group-containing polymerizable monomer and a methacryloyl group-containing polymerizable monomer.

Specific examples of the monofunctional (meth)acrylate polymerizable monomer (l) are as follows.

Examples of the monofunctional (meth)acrylate polymerizable monomer include: (meth)acrylic esters such as methyl (meth)acrylate, ethyl (meth)acrylate, butyl (meth)acrylate, hexyl (meth)acrylate, glycidyl (meth)acrylate, lauryl (meth)acrylate, cyclohexyl (meth)acrylate, benzyl (meth)acrylate, allyl (meth)acrylate, 2-ethoxyethyl (meth)acrylate, glycerol (meth)acrylate, and isobonyl (meth)acrylate; silane compounds such as γ-(meth)acryloyloxypropyltrimethoxysilane and γ-(meth)acryloyloxypropyltriethoxysilane; and nitrogen-containing compounds such as 2-(N,N-dimethylamino)ethyl(meth)acrylate and N-methylol (meth)acrylamide.

The content of the monofunctional (meth)acrylate polymerizable monomer is not limited so long as it is in the range of 4% to 16% by weight. In the case where the content of the monofunctional (meth)acrylate polymerizable monomer is less than 4% by weight, the hardenability of the resin component decreases, causing a problem in material property of the hardened material. In the case where the content of the monofunctional (meth)acrylate polymerizable monomer exceeds 16% by weight, the polymerization shrinkage of the resin component is significant, causing a problem such as a decrease in cavity sealability.

—Hydrophilic Polymerizable Monomer (p)

The hydrophilic polymerizable monomer (p) is not limited, so long as it has at least one polymerizable group and at least 5 parts by weight dissolve in 100 parts by weight water at 23° C.

In the present invention, the hydrophilicity is evaluated by the following method.

100 g of distilled water is put in a sample bottle, and 5 g of the polymerizable monomer is added to it and mixed to be uniform. The sample is then left for 24 hours. The solubility is regarded as greater than or equal to 5% in the case where the distilled water and the polymerizable monomer are colorless and transparent, and less than or equal to 5% in the case where the distilled water and the polymerizable monomer are white.

Specific examples of the hydrophilic polymerizable monomer (p) include 2-hydroxyethyl (meth)acrylate, 2-hydroxypropyl (meth)acrylate, 3-hydroxypropyl (meth)acrylate, 1,2-dihydroxypropyl (meth)acrylate, 1,3-dihydroxypropyl (meth)acrylate, 2,3-dihydroxypropyl (meth)acrylate, 2-hydroxypropyl-1,3-di(meth)acrylate, 3-hydroxypropyl-1,2-di(meth)acrylate, pentaerythritol di(meth)acrylate, 2-trimethylammoniumethyl (meth)acrylchloride, (meth)acrylamide, 2-hydroxyethyl (meth)acrylamide, and polyethylene glycol di(meth)acrylate (the number of oxyethylene groups is greater than or equal to 9), though the hydrophilic polymerizable monomer is not limited to such.

These hydrophilic polymerizable monomers may be used singly or in combination. Of these hydrophilic polymerizable monomers, a hydrophilic polymerizable monomer that dissolves by 10 parts by weight or more in 100 parts by weight water at 23° C. is preferable, and a hydrophilic polymerizable monomer that dissolves by 20 parts by weight or more in 100 parts by weight water at 23° C. is more preferable. Specific examples of the hydrophilic polymerizable monomer include 2-hydroxyethyl (meth)acrylate, polyethylene glycol di(meth)acrylate (the number of oxyethylene groups is 9), polyethylene glycol di(meth)acrylate (the number of oxyethylene groups is 14), and polyethylene glycol di(meth)acrylate (the number of oxyethylene groups is 23), though the hydrophilic polymerizable monomer is not limited to such.

To enable the dental resin temporary sealing material composition according to the present invention to exhibit excellent sealability to cavity walls after hardening, flexible material property, low water absorbability, stable hardness by water immersion, little dimensional change, and the like, the inclusion of a hydrophilic polymerizable monomer having at least two polymerizable groups is preferable, and the inclusion of both a hydrophilic polymerizable monomer having one polymerizable group and a hydrophilic polymerizable monomer having at least two polymerizable groups is more preferable.

The content of the hydrophilic polymerizable monomer is not limited so long as it is in the range of 4% to 13% by weight. A preferable range is 6% to 13% by weight.

In the case where the content of the hydrophilic polymerizable monomer is less than 4% by weight, the affinity for the cavity walls which are hydrophilic is poor, leading to a decrease in cavity sealability. In the case where the content of the hydrophilic polymerizable monomer exceeds 13% by weight, the polymerization hardenability of the resin component is low, causing problems such as an increased water absorption rate and significant dimensional change.

—Polymerization Initiator (q)

The polymerization initiator (q) that can be used in the dental resin temporary sealing material composition according to the present invention is not particularly limited, and may be a well-known radical precursor used in the dental field. Typically, polymerization initiators (q) are mainly classified into a type (photopolymerization initiator) that initiates polymerization by light irradiation and a type (chemical polymerization initiator) that initiates polymerization by mixture immediately before use, and preferably used.

The photopolymerization initiator may be a photosensitizer, or a combination of a photosensitizer and a photopolymerization promoter, though not limited to such.

Specific examples of the photosensitizer include: α-diketones such as benzyl, camphorquinone, α-naphthyl, acetonaphthone, p,p'-dimethoxybenzyl, p,p'-dichlorobenzylacetyl, pentanedione, 1,2-phenanthrenequinone, 1,4-phenanthrenequinone, 3,4-phenanthrenequinone, 9,10-phenanthrenequinone, and naphthoquinone; benzoin alkylethers such as benzoin, benzoin methyl ether, and benzoin ethyl ether; thioxanthones such as thioxanthone, 2-chlorothioxanthone, 2-methylthioxanthone, 2-isopropylthioxanthone, 2-methoxythioxanthone, 2-hydroxythioxanthone, 2,4-diethylthioxanthone, and 2,4-diisopropylthioxanthone; benzophenones such as benzophenone, p-chlorobenzophenone, and p-methoxybenzophenone; acylphosphine oxides such as 2,4,6-trimethylbenzoyl-diphenylphosphine oxide, and bis(2,6-dimethoxybenzoyl)-2,4,4-trimethylpentylphosphine oxide; α-aminoacetophenones such as 2-benzyl-dimethylamino-1-(4-morpholinophenyl)-butanone-1 and 2-benzyl-diethylamino-1-(4-morpholinophenyl)-propanone-1; ketals such as benzyl dimethyl ketal, benzyl diethyl ketal, and benzyl(2-methoxyethyl ketal); and titanocenes such as bis(cyclopentadienyl)-bis[2,6-difluoro-3-(1-pyrrolyl)phenyl]-titanium, bis(cycpentadienyl)-bis(pentafluorophenyl)-titanium, and bis(cyclopentadienyl)-bis(2,3,5,6-tetrafluoro-4-disiloxyphenyl)-titanium.

Specific examples of the photopolymerization promoter include: tertiary amines such as N,N-dimethylaniline, N,N-diethylaniline, N,N-di-n-butylaniline, N,N-dibenzylaniline, p-N,N-dimethyl-toluidine, m-N,N-dimethyl-toluidine, p-N,N-diethyl-toluidine, p-bromo-N,N-dimethylaniline, m-chloro-N,N-dimethylaniline, p-dimethylaminobenzaldehyde, p-dimethylaminoacetophenone, p-dimethylaminobenzoic acid, p-dimethylaminobenzoic acid ethyl ester, p-dimethylaminobenzoic acid amino ester, N,N-dimethylanthranylic acid methyl ester, N,N-dihydroxyethylaniline, p-N,N-dihydroxyethyl-toluidine, p-dimethylaminophenyl alcohol, p-dimethylaminostylene, N,N-dimethyl-3,5-xylidine, 4-dimethylaminopyridine, N,N-dimethyl-α-naphthylamine, N,N-dimethyl-β-naphthylamine, tributylamine, tripropylamine, triethylamine, N-methyldiethanolamine, N-ethyldiethanolamine, N,N-dimethylhexylamine, N,N-dimethyldodecylamine, N,N-dimethylstearylamine, N,N-dimethylaminoethyl methacrylate, N,N-diethylaminoethyl methacrylate, and 2,2'-(n-butylimino)diethanol; secondary amines such as N-phenylglycine; barbituric acids such as 5-butylbarbituric acid, and 1-benzyl-5-phenylbarbituric acid; tin compounds such as dibutyltin diacetate, dibutyltin dilaurate, dioctyltin dilaurate, dioctyltin diverthatate, dioctyltinbis(mercaptoacetic acid isooctyl ester) salt, and tetramethyl-1,3-diacetoxydistannoxane; aldehyde compounds such as lauryl aldehyde and terephthalaldehyde; and sulfur-containing compounds such as dodecyl mercaptan, 2-mercaptobenzoxazole, 1-decanethiol, and thiosalicylic acid.

For improved photopolymerization promoting ability, it is effective to add, in addition to the above-mentioned photopolymerization promoter, oxycarboxylic acids such as citric acid, malic acid, tartaric acid, glycolic acid, gluconic acid, α-oxyisobutyric acid, 2-hydroxypropanoic acid, 3-hydroxypropanoic acid, 3-hydroxybutanoic acid, 4-hydroxybutanoic acid, and dimethylol propionic acid.

The chemical polymerization initiator may be a redox type polymerization initiator system composed of an organic peroxide/amine compound, an organic peroxide/amine compound/sulfinate, or an organic peroxide/amine compound/borate compound, or an organic metal type polymerization initiator system that reacts with oxygen or water to initiate polymerization. The sulfinate or the borate compound can further initiate polymerization by reacting with a polymerizable monomer having an acidic group, though the present invention is not limited to such.

Specific examples of the organic peroxide include benzoyl peroxide, p-chlorobenzoyl peroxide, 2,4-dichlorobenzoyl peroxide, acetyl peroxide, lauroyl peroxide, tertiary butyl peroxide, cumene hydroperoxide, 2,5-dimethyl-2,5-di(benzoylperoxy)hexane, 2,5-dihydroperoxide, methyl ethyl ketone peroxide, and tertiary butyl peroxybenzoate.

The amine compound is preferably a secondary amine or a tertiary amine in which an amine group is attached to an aryl group, as an example. Specific examples include p-N,N-dimethyl-toluidine, N,N-dimethyl aniline, N-β-hydroxyethyl-aniline, N,N-di(β-hydroxyethyl)-aniline, p-N,N-di(β-hydroxyethyl)-toluidine, N-methyl-aniline, and p-N-methyl-toluidine.

Specific examples of the sulfinate include benzenesulfinic sodium, benzenesulfinic lithium, and p-toluenesulfinic sodium.

Specific examples of the borate compound include sodium salt, lithium salt, potassium salt, magnesium salt, tetrabutylammonium salt, and tetramethylammonium salt of trialkylphenyl boron, trialkyl(p-fluorophenyl) boron (alkyl group is n-butyl group, n-octyl group, n-dodecyl group, etc.), and the like.

Specific examples of the organic metal type polymerization initiator include organic boron compounds such as triphenylborane, tributylborane, and tributylborane partial oxide.

As a thermal polymerization initiator by heating or warming, not only the above-mentioned organic peroxide but also an azo compound such as azobisisobutyronitrile, azobisisobutyric acid methyl, or azobiscyanovaleric acid is preferably used.

These polymerization initiators may be used singly or in combination, regardless of the polymerization mode or the polymerization method. The polymerization initiator may be subject to a secondary treatment such as microencapsulation, to stabilize polymerization or delay polymerization.

Of these polymerization initiators, the chemical polymerization initiator that initiates polymerization by mixture immediately before use is preferably used. The use of the chemical polymerization initiator is most desirable for its simplicity. Of the chemical polymerization initiators, a combination of an organic peroxide and a tertiary amine is more preferable, and a combination such as an aromatic amine in which an amino group such as p-N,N-dimethyl aminobenzoic acid ethyl and benzoyl peroxide are directly attached to a benzene ring or an aliphatic amine that has a double bond in a molecule of N,N-dimethylaminoethylmethacrylate or the like is most preferable.

The content of the polymerization initiator can be selected as appropriate depending on use. A preferable range is 0.1 to 5 parts by weight and a more preferable range is 0.1 to 2 parts by weight, with respect to 100 parts by weight the total polymerizable monomer combining the monofunctional (meth)acrylate polymerizable monomer and the hydrophilic polymerizable monomer. In the case where the content of the polymerization initiator is less than 0.1 parts by weight, the polymerization hardenability is insufficient, and the desired material property or performance cannot be achieved. In the case where the content of the polymerization initiator exceeds 5 parts by weight, the polymerization hardening accelerates, which causes a problem with operability such as the difficulty of the filling operation to the cavity. Besides, the hardened material becomes harder with polymerization, which causes a problem with removability such as the difficulty of removing the hardened material from the cavity upon removal.

—Plasticizer (n)

The plasticizer (n) is not particularly limited, and may be any well-known plasticizer. Specific examples of the plasticizer (n) include: phthalate esters such as dimethyl phthalate, diethyl phthalate, dibutyl phthalate, diheptyl phthalate, dioctyl phthalate, di-isodecyl phthalate, butyl benzyl phthalate, diisononyl phthalate, ethyl phthalyl ethyl glycolate, and butyl phthalyl butyl glycolate; dibasic acid esters other than phthalic acid, such as dibutyl adipate, dibutyl diglycol adipate, dibutyl sebacate, dioctyl sebacate, dibutyl maleate, and dibutyl fumarate; glycerol esters such as glycerol triacetate; phosphate esters such as tributyl phosphate, trioctyl phosphate, and triphenyl phosphate; and carboxylate esters such as benzyl benzoate, ethyl benzoate, butyl benzoate, and amyl benzoate, though the plasticizer is not limited to such. These plasticizers may be used singly or in combination. Of these plasticizers, carboxylate esters are preferable, and benzyl benzoate, ethyl benzoate, butyl benzoate, and amyl benzoate are particularly preferable.

The content of the plasticizer (n) can be adjusted as appropriate depending on the use method, the purpose of use, the composition, etc. The content of the plasticizer is not limited so long as it is in the range of 5% to 25% by weight. A preferable range is 8% to 25% by weight. In the case where the content of the plasticizer is less than 5% by weight, the hardened material lacks flexibility, which causes a problem such as a failure to remove the hardened material at once upon removal. In the case where the content of the plasticizer exceeds 25% by weight, the plasticizer flows out over time after temporary sealing, and so a dimensional change occurs. This may lead to lower sealability of the cavity.

The following components may be optionally added to the dental resin temporary sealing material composition according to the present invention depending on need: a polymerizable monomer having two or more non-hydrophilic functional groups as a cross linker, a vehicle such as fumed silica, an ultraviolet absorber such as 2-hydroxy-4-methylbenzophenone, a polymerization inhibitor such as hydroquinone, hydroquinone monomethyl ether, or 2,5-ditertiary butyl-4-methylphenol, an antitarnish agent, an antimicrobial, a color pigment, and other conventionally known additives.

The package form of the dental resin temporary sealing material composition according to the present invention is not particularly limited, and any package form such as powder-liquid, powder-paste, paste-liquid, paste-paste, and one paste may be used. A preferable package form is powder-liquid or powder-paste.

The manufacturing method of the dental resin temporary sealing material composition according to the present invention is not particularly limited, though the following method is preferable as an example. The ion sustained-release glass and the polymerization initiator are dispersed in the non-crosslinked (meth)acrylate polymer to obtain the powder material. Further, the monofunctional (meth)acrylate polymerizable monomer, the hydrophilic polymerizable monomer, and the plasticizer are mixed to obtain the liquid material.

Examples

Examples of the present invention and comparative examples are described in detail below, though the present invention is not limited to these examples.

(1) Ion Sustained-Released Glass and Each Filler
[Measurement of Element Content Resulting from Ion Sustained-Released from Ion Sustained-Release Glass and Each Filler]

0.1 g of the ion sustained-release glass or filler was added to 100 g of distilled water, and stirred for 1 hour. The element concentration resulting from each ion sustained-released in a solution filtered by an analytical syringe filter (Chromatdisk 25A, pore size: 0.2 μm, GL Sciences Inc.) is denoted by F1. Likewise, 0.1 g of the ion sustained-release glass or filler was added to 100 g of distilled water, and stirred for 2 hours. The element concentration resulting from each ion sustained-released in a solution filtered by the same operation is denoted by F2. Regarding fluorine, the fluoride ion was measured using a fluoride ion composite electrode (Model 9609, Orion Research Inc.) and an ion meter (Model 720A, Orion Research Inc.), and the measurement was used for conversion to the fluorine element concentration. Upon measurement, 0.5 ml of TISABIII (manufactured by Orion Research Inc.) was added as an ionic strength adjuster. Calibration was performed using standard solutions of 0.1 ppm, 1 ppm, 10 ppm, and 50 ppm (500 ppm of fluorine). The other elements (Na, B, Al, Sr) were calculated by measurement, using an inductively coupled plasma atomic emission spectrophotometer (ICPS-8000, Shimadzu Corporation). Calibration was performed using standard solutions of 0.1 ppm, 1 ppm, 10 ppm, and 50 ppm. In the case where the measured elements were not within the calibration, the measurement was conducted with dilution according to need.

[Evaluation of Acid Neutralizing Capacity of Ion Sustained-Release Glass and Each Filler]

The acid neutralizing capacity of the ion sustained-release glass or filler used in the present invention was evaluated by the following method. 0.1 g of the ion sustained-release glass or filler was added to 10 g of a lactic acid water solution with pH adjusted to 4.0, and stirred for 5 minutes. The pH was then measured using a pH meter (D-51, HORIBA, Ltd.) for evaluation.

[Manufacture of Ion Sustained-Release Glass 1]

The raw materials that are silicon dioxide, aluminum oxide, boron oxide, sodium fluoride, and strontium carbonate (glass composition: SiO2 23.8% by mass, Al2O3 16.2% by mass, B2O3 10.5% by mass, SrO 35.6% by mass, Na2O 2.3% by mass, F 11.6% by mass) were uniformly mixed using a ball mill to prepare the raw material mixture, and the raw material mixture was molten in a melting furnace at 1400° C. The melt was then taken out of the melting furnace, and cooled on a cool steel plate, a roll, or in water to create glass. After introducing 4 kg of alumina pebbles of 6 mmφ in diameter into an alumina pot (internal volume: 3.6 liters) of a four-tier vibration mill, 500 g of the glass obtained above was introduced and grinded for 40 hours, thus obtaining the ion sustained-release glass 1. The 50% average particle diameter of the ion sustained-release glass 1 measured by a laser diffraction particle size measuring instrument (microtrack SPA, Nikkiso Co., Ltd.) was 1.2 μm. The element content (ion content only in the case of fluoride ion) resulting from the ion released from the ion sustained-release glass 1 was measured and its conformity with Expression (1) was determined. The result is shown in Table 1.

[Manufacture of Ion Sustained-Release Glass 2]

The following polysiloxane treatment and acid polymer treatment were performed to obtain the surface-treated ion sustained-release glass 2.

500 g of the above-mentioned ion sustained-release glass 1 and a silane compound (a low condensate of a silane compound obtained by stirring 5 g of tetramethoxysilane, 1000 g of water, and 100 g of ethanol for 2 hours at ambient temperature beforehand) were cast into a universal mixing stirrer and stirred and mixed for 90 minutes. The mixture was then heat-treated at 140° C. for 30 hours, thus obtaining the heat-treated object. The heat-treated object was crushed using a Henschel mixer, to obtain polysiloxane-coated ion sustained-release glass. While stirring 500 g of the polysiloxane-coated glass, an acid polymer water solution (polyacrylic acid water solution, polymer concentration: 13% by weight, weight-average molecular weight: 20000, Nacalai Tesque, Inc.) was sprayed using a Henschel mixer. Heat treatment (at 100° C. for 3 hours) was then performed to manufacture the surface-treated ion sustained-release glass 2. The 50% average particle diameter of the ion sustained-release glass 2 measured by a laser diffraction particle size measuring instrument (microtrack SPA: Nikkiso Co., Ltd.) was 1.3 μm. The element content (ion content only in the case of fluoride ion) resulting from the ion released from the surface-treated ion sustained-release glass 2 was measured and its conformity with Expression (1) was determined. The result is shown in Table 1.

[Manufacture of Ion Sustained-Release Glass 3]

The raw materials that are silicon dioxide, aluminum oxide, boron oxide, sodium fluoride, and strontium carbonate were mixed, and the mixture was molten at 1400° C. to obtain glass (glass composition: SiO2 19.8% by mass, Al2O3 19.8% by mass, B2O3 11.7% by mass, SrO 35.0% by mass, Na2O 2.3% by mass, F 11.4% by mass). The glass was then grinded for 10 hours using a vibration mill, thus obtaining the glass 3. 500 g of the glass 3 and a silane compound (a low condensate of a silane compound obtained by stirring 10 g of tetramethoxysilane, 1500 g of water, 100 g of ethanol, 70 g of methanol, and 50 g of isopropanol for 2 hours at ambient temperature beforehand) were cast into a universal mixing stirrer and stirred and mixed for 90 minutes. The mixture was then heat-treated at 140° C. for 30 hours, thus obtaining the heat-treated object. The heat-treated object was crushed using a Henschel mixer, to obtain polysiloxane-coated ion sustained-release glass. While stirring 500 g of the polysiloxane-coated glass, an acid polymer water solution (polyacrylic acid water solution, polymer concentration: 13% by weight, weight-average molecular weight: 20000, Nacalai Tesque, Inc.) was sprayed using a Henschel mixer. Heat treatment (at 100° C. for 3 hours) was then performed to manufacture the surface-treated ion sustained-release glass 3.

The 50% average particle diameter of the surface-treated ion sustained-release glass 3 measured by a laser diffraction particle size measuring instrument (microtrack SPA, Nikkiso Co., Ltd.) was 3.1 μm. The element content (ion content only in the case of fluoride ion) resulting from the ion released from the surface-treated ion sustained-release glass 3 was measured and its conformity with Expression (1) was determined. The result is shown in Table 1.

[Non-Ion Sustained-Release Filler]

The following filler was used as a non-ion sustained-release filler.

FLX: FUSELEX X (silica filler, particle diameter=2.1 μm, Tatsumori Ltd.)

SOC5: Admafine SO-C5 which is a silica filler (silica filler, average particle diameter=1.6 μm, Admatechs)

NaF: sodium fluoride powder (Nacalai Tesque, Inc.)

The element content (ion content only in the case of fluoride ion) resulting from the ion released from the filler was measured and its conformity with Expression (1) was determined. The result is shown in Table 1.

TABLE 1

Details of ion sustained-release glass and filler

| | | | Ion sustained-release glass | | | Non-ion sustained-release filler | | |
|---|---|---|---|---|---|---|---|---|
| | | | Ion sustained-release glass 1 | Ion sustained-release glass 2 | Ion sustained-release glass 3 | FLX | SOC5 | NaF |
| Average particle diameter | | | 1.2 | 1.3 | 3.1 | — | 1.6 | — |
| Element concentration (ppm) | F1 | F | 8.9 | 21.3 | 15.5 | 0.0 | 0.0 | 453.0 |
| | | Na | 1.2 | 1.5 | 0.9 | 0.0 | 0.0 | 452.8 |
| | | B | 2.3 | 2.8 | 1.9 | 0.0 | 0.0 | 0.0 |
| | | Al | 0.2 | 0.1 | 0.1 | 0.0 | 0.0 | 0.0 |
| | | Sr | 9.2 | 14.6 | 9.5 | 0.0 | 0.0 | 0.0 |
| | F2 | F | 12.5 | 32.3 | 22.5 | 0.0 | 0.0 | 453.0 |
| | | Na | 1.5 | 2.3 | 1.6 | 0.0 | 0.0 | 452.8 |
| | | B | 2.5 | 3.7 | 3.6 | 0.0 | 0.0 | 0.0 |
| | | Al | 0.3 | 0.2 | 0.05 | 0.0 | 0.0 | 0.0 |
| | | Sr | 9.7 | 21.3 | 12.4 | 0.0 | 0.0 | 0.0 |
| Acid neutralizing capacity (pH) | | | 6.6 | 6.8 | 6.8 | 4.1 | 4.1 | 4.0 |
| Conformity with F2 > F1 (Expression 1) | | | Conforming | Conforming | Conforming | Nonconforming | Nonconforming | Nonconforming |

0.1 g of the ion sustained-release glass or filler was added to 10 g of a lactic acid water solution with pH adjusted to 4.0, and stirred for 5 minutes. The following results were then obtained. The pH of the ion sustained-release glass was greater than or equal to 6.5, indicating that the ion sustained-release glass has the acid neutralizing capacity. The pH of the non-ion sustained-release filler was, on the other hand, almost unchanged at about 4, indicating that the non-ion sustained-release filler does not have the acid neutralizing capacity. Moreover, the element content (ion content only in the case of fluoride ion) sustained-released from the ion sustained-release glass conforms to Expression (1), whereas the element content (ion content only in the case of fluoride ion) sustained-released from the non-ion sustained-release filler does not conform to Expression (1).

(2) Neutralization Promoting Ion Sustained-Release Dental Film

Examples and comparative examples of the neutralization promoting ion sustained-release dental film are described below.

The following test methods are used to evaluate the performance of the neutralization promoting ion sustained-release dental film prepared in each of the examples and the comparative examples.

[Measurement of Element Content Resulting from Ion Sustained-Released from Neutralization Promoting Ion Sustained-Release Dental Film]

The neutralization promoting ion sustained-release dental film cut to 18 mm×18 mm was attached onto a glass plate (18 mm×18 mm), and the glass plate sample was immersed in 5 mL of distilled water. The glass plate sample was taken out of the distilled water after 1 hour, and immersed again in 5 mL of new distilled water. This operation was performed three times in total. As a result, three solutions including ions released from the neutralization promoting ion sustained-release dental film into the distilled water in the period of 0 to 1 hour, the period of 1 to 2 hour, and the period of 2 to 3 hour were obtained. The element content resulting from each ion in each of these solutions was measured by the same measurement method mentioned above. In the case where the measured elements were not within the calibration, the measurement was conducted with dilution according to need.

[Film Thickness of Neutralization Promoting Ion Sustained-Release Dental Film]

The thickness of the neutralization promoting ion sustained-release dental film was measured at 5 positions using a micrometer (MDC25SB, Mitutoyo Corporation). The average value is shown as the average film thickness in Tables 2 and 3.

[Evaluation of Acid Neutralizing Capacity of Neutralization Promoting Ion Sustained-Release Dental Film]

The neutralization promoting ion sustained-release dental film of 15 mm×15 mm was attached to a glass plate (18 mm×18 mm), and immersed in 5 mL of a lactic acid water solution (with pH adjusted to 4.0). The pH of the lactic acid water solution after 6 hours and after 24 hours was measured using a pH meter (D-51, HORIBA, Ltd.).

[Evaluation of Foul Breath Suppression Effect of Neutralization Promoting Ion Sustained-Release Dental Film]

To evaluate the foul breath suppression effect of each of the examples and the comparative examples, the following test was conducted on 5 persons. The neutralization promoting ion sustained-release dental film cut to 18 mm×18 mm was attached onto the tongue of each test subject, and the breath after 30 minutes was compared with the breath before the attachment for evaluation. In the breath comparison, the sulfur compound concentration (VSC value) in the oral cavity resulting from hydrogen sulfide, methylmercaptan, dimethyl sulfide, etc. in the breath was measured (XP-Breath-Tron, New Cosmos Electric Co., Ltd.), and the value of VSC(1) in the breath before the attachment and the value of VSC(2) in the breath 30 minutes after the attachment were compared. The foul breath reduction rate (%)= $(1-VSC(2)/VSC(1))\times 100$ was calculated based on the evaluation result. The average value of the 5 persons is shown in Tables 2 and 3.

The following shows the names and abbreviations of the components used in the examples of the neutralization promoting ion sustained-release dental film according to the present invention and the comparative examples.

—Film Forming Material
starch: potato starch
PVP: polyvinylpyrrolidone (630000 in molecular weight, Tokyo Chemical Industry Co., Ltd.)
—Fluoride Ion Supply Material
NaF: sodium fluoride powder (Nacalai Tesque, Inc.)

—Sweetener
xylitol
—Saliva Secretion Promoter
citric acid

The manufacturing method of the neutralization promoting ion sustained-release dental film containing the ion sustained-release glass or the non-ion sustained-release filler described above is as follows. The components constituting each neutralization promoting ion sustained-release dental film shown in Tables 2 and 3 were added in 4000 g of distilled water so that the components are 100 g in total, heated and stirred at 80° C. for 1 hour, and then dried under reduced pressure at 90° C. for 20 hours, thus obtaining the neutralization promoting ion sustained-release dental film. The composition and the evaluation result of the neutralization promoting ion sustained-release dental film are shown in Table 2.

In Examples 1 to 6 which are each the neutralization promoting ion sustained-release dental film containing the ion sustained-release glass, F, Na, B, Al. and Sr ions were stably sustained-released over a long period of time. These ions sustained-released in the oral cavity are expected to improve the acid resistance of the tooth substance, enhance the acid buffering capacity, and prevent foul breath. Moreover, the acid neutralizing capacity evaluation suggests that the neutralization promoting ion sustained-release dental film has high acid neutralizing capacity, as the neutralization promoting ion sustained-release dental film neutralized the lactic acid water solution of pH 4.0 to about pH 6 after 6 hours and to near neutral after 24 hours. The foul breath suppression evaluation shows a reduction in VSC value by 36% to 62%, indicating that the neutralization promoting ion sustained-release dental film is effective in foul breath suppression.

TABLE 2

Examples of neutralization promoting ion sustained-release film

| | | | Example 1 | Example 2 | Example 3 | Example 4 | Example 5 | Example 6 |
|---|---|---|---|---|---|---|---|---|
| Component (wt %) | Ion sustained-release glass | Ion sustained-release glass 1 | 5 | — | — | 10 | — | 5 |
| | | Ion sustained-release glass 2 | — | 15 | — | 20 | 20 | — |
| | | Ion sustained-release glass 3 | — | — | 20 | — | — | 10 |
| | Non-ion sustained-release filler | FLX | 5 | — | — | — | — | 3 |
| | | SOC5 | — | — | — | — | 5 | — |
| | Film forming material | Starch | 85.9 | 83.8 | — | 10 | — | 17 |
| | | PVP | — | — | 74.4 | 58.9 | 71.9 | 62.9 |
| | Fluoride ion supply material | NaF | — | — | — | — | 1 | 1 |
| | Sweetener | Xylitol | 4 | 1 | 5.5 | 1 | 2 | 1 |
| | Saliva secretion promoter | Citric acid | 0.1 | 0.2 | 0.1 | 0.1 | 0.1 | 0.1 |
| | Total | | 100 | 100 | 100 | 100 | 100 | 100 |
| Average film thickness (μm) | | | 30 | 30 | 25 | 30 | 50 | 40 |
| Element concentration (ppm) | 0~1 hour | F | 0.6 | 2.2 | 3.1 | 3 | 5 | 3.9 |
| | | Na | 0.6 | 1.8 | 3.2 | 2.9 | 2.4 | 1.3 |
| | | B | 0.3 | 0.9 | 1.4 | 1.3 | 0.9 | 0.7 |
| | | Al | 0.1 | 0.4 | 0.8 | 0.9 | 0.5 | 0.9 |
| | | Sr | 0.8 | 2.5 | 3.3 | 3.9 | 2.3 | 1.2 |
| | 1~2 hour | F | 0.3 | 1.5 | 2.3 | 1.8 | 1.4 | 1.8 |
| | | Na | 0.2 | 1.6 | 1.9 | 1.3 | 1.2 | 1.9 |
| | | B | 0.3 | 0.2 | 0.4 | 0.3 | 0.3 | 0.3 |
| | | Al | 0.1 | 0.5 | 0.8 | 0.6 | 0.4 | 0.5 |
| | | Sr | 1.3 | 1.5 | 2.2 | 1.8 | 0.8 | 0.9 |
| | 2~3 hour | F | 0.2 | 1 | 1.8 | 1.5 | 1.3 | 1.1 |
| | | Na | 0.2 | 1.2 | 1.8 | 1.9 | 1.2 | 1.1 |
| | | B | 0.1 | 0.2 | 0.4 | 0.3 | 0.2 | 0.3 |
| | | Al | 0.1 | 0.3 | 0.6 | 0.5 | 0.4 | 0.3 |
| | | Sr | 0.7 | 1.3 | 1.8 | 1.5 | 1.2 | 0.6 |
| Acid neutralizing capacity | After 6 hours | | 5.8 | 5.8 | 6.1 | 6 | 5.9 | 5.9 |
| | After 24 hours | | 6.3 | 6.7 | 6.6 | 6.9 | 6.7 | 6.4 |
| Foul breath reduction rate | | | 36% | 52% | 55% | 51% | 62% | 56% |

TABLE 3

Comparative examples of neutralization promoting ion sustained-release film

| Component (wt %) | | | Comparative Example 1 | Comparative Example 2 | Comparative Example 3 | Comparative Example 4 |
|---|---|---|---|---|---|---|
| Component (wt %) | Ion sustained-release glass | Ion sustained-release glass 1 | — | — | — | — |
| | | Ion sustained-release glass 2 | — | — | — | — |
| | | Ion sustained-release glass 3 | — | — | — | — |
| | Non-ion sustained-release filler | FLX | 15 | — | 5 | — |
| | | SOC5 | — | 10 | 5 | — |
| | Film forming material | Starch | 79.9 | — | 70 | 47 |
| | | PVP | — | 85 | 14 | 47 |
| | Fluoride ion supply material | NaF | — | — | 1 | 1 |
| | Sweetener | Xylitol | 5 | 5 | 5 | 5 |
| | Saliva secretion promoter | Citric acid | 0.1 | — | — | — |
| | Total | | 100 | 100 | 10 | 100 |
| Film thickness (μm) | | | 30 | 30 | 25 | 35 |
| Element concentration (ppm) | 0~1 hour | F | 0 | 0 | 1.2 | 1.3 |
| | | Na | 0 | 0 | 0 | 0 |
| | | B | 0 | 0 | 0 | 0 |
| | | Al | 0 | 0 | 0 | 0 |
| | | Sr | 0 | 0 | 0 | 0 |
| | 1~2 hour | F | 0 | 0 | 0 | 0 |
| | | Na | 0 | 0 | 0 | 0 |
| | | B | 0 | 0 | 0 | 0 |
| | | Al | 0 | 0 | 0 | 0 |
| | | Sr | 0 | 0 | 0 | 0 |
| | 2~3 hour | F | 0 | 0 | 0 | 0 |
| | | Na | 0 | 0 | 0 | 0 |
| | | B | 0 | 0 | 0 | 0 |
| | | Al | 0 | 0 | 0 | 0 |
| | | Sr | 0 | 0 | 0 | 0 |
| Acid neutralizing capacity | | After 6 hours | 4.1 | 4 | 4.1 | 4.1 |
| | | After 24 hours | 4.1 | 4.1 | 4.1 | 4.1 |
| Foul breath reduction rate | | | 3% | 5% | −2% | 3% |

In Comparative Examples 1 and 2 which are each the neutralization promoting ion sustained-release dental film not containing the ion sustained-release glass, no ion was sustained-released, suggesting that the neutralization promoting ion sustained-release dental film has no effect of improving the acid resistance of the tooth substance and the like. In Comparative Examples 3 and 4 which are each the neutralization promoting ion sustained-release dental film containing only sodium fluoride as an ion supply source, the sustained release of the fluoride ion was observed in the initial period of 0 to 1 hour, but the fluoride ion was subsequently not sustained-released, so that the improvement of the acid resistance of the tooth substance is hardly expected. Moreover, the acid neutralizing capacity evaluation indicates that the neutralization promoting ion sustained-release dental film has no acid neutralizing capacity. The foul breath suppression evaluation shows almost no change in VSC value, indicating that the neutralization promoting ion sustained-release dental film has no foul breath suppression effect.

(3) Dental Varnish Composition

Examples and comparative examples of the dental varnish composition are described below.

The following test methods are used to evaluate the performance of the dental varnish composition prepared in each of the examples and the comparative examples.

[Measurement of Element Content Resulting from Ion Sustained-Released from Dental Varnish Composition]

Masking tape (50 μm in thickness) having a hole of 4 mm in diameter was attached to a glass plate (18 mm×18 mm), and the dental varnish composition was applied into the hole of 4 mm in diameter, and leveled to a thickness of about 50 μm. This glass plate sample 1 was immersed in 5 mL of distilled water. The glass plate sample 1 was taken out of the distilled water after 1 hour, and immersed again in 5 mL of new distilled water. This operation was performed three times in total. As a result, three solutions including ions released from the dental varnish composition into the distilled water in the period of 0 to 1 hour, the period of 1 to 2 hour, and the period of 2 to 3 hour were obtained. The element content resulting from each ion in each of these solutions was measured by the same measurement method mentioned above. In the case where the measured elements were not within the calibration, the measurement was conducted with dilution according to need.

[Evaluation of Acid Neutralizing Capacity of Dental Varnish Composition]

Masking tape (50 μm in thickness) having a hole of 10 mm in diameter was attached to a glass plate (18 mm×18 mm), and the dental varnish composition was applied into the hole of 10 mm in diameter, and leveled to a thickness of about 50 μm. This glass plate sample 2 was immersed in 5 mL of a lactic acid water solution (with pH adjusted to 4.0). The pH of the lactic acid water solution after 6 hours and after 24 hours was measured using a pH meter (D-51, HORIBA, Ltd.).

[Evaluation of Retentivity of Film Formed on Tooth Substance by Application of Dental Varnish Composition]

The dental root portion was removed from bovine lower jaw permanent central incisors removed after slaughter, and the dental crown portion was cut to obtain a bovine tooth strip. The bovine tooth strip was embedded with an epoxy resin. The embedded bovine tooth was ground using a #600 waterproof abrasive paper while pouring water to expose enamel, and then washed with water and dried. The varnish composition was applied to the bovine enamel surface, and incubated at 37° C. with a humidity of 80% for 30 minutes. After this, the sample was subjected to 1000 heat cycles (immersion for 1 minute per cycle) of 5° C. to 60° C., and the retentivity of the varnish on the resulting bovine enamel surface was evaluated.

In the retentivity evaluation, the following rating was used: A when the rate of varnish retention on the bovine enamel is greater than or equal to 80%, B when the rate of varnish retention on the bovine enamel is greater than or equal to 30% and less than 80%, and C when the remaining varnish is less than 30%.

[Evaluation of Foul Breath Suppression Effect]

To evaluate the foul breath suppression effect of each of the examples and the comparative examples, the following test was conducted on 5 persons. The varnish composition was applied to the tooth surface (masticating surface, buccal surface, and lingual surface) of each test subject 20 years of age or older whose 28 teeth except wisdom teeth are all healthy, and the breath after 2 hours was compared with the breath before the application for evaluation. In the breath comparison, the sulfur compound concentration (VSC value) in the oral cavity resulting from hydrogen sulfide, methylmercaptan, dimethyl sulfide, etc. in the breath was measured (XP-Breath-Tron, New Cosmos Electric Co., Ltd.), and the value of VSC(1) in the breath before the application and the value of VSC(2) in the breath 2 hours after the application were compared. The foul breath reduction rate (%)=(1−VSC(2)/VSC(1))×100 was calculated based on the evaluation result. The average value of the 5 persons is shown in Tables 4 and 5.

The following shows the names and abbreviations of the components used in the examples of the dental varnish composition according to the present invention and the comparative examples.

—Film Component
rosin A: PINECRYSTAL (hydrogenated rosin, Arakawa Chemical Industries, Ltd.)
rosin B: white chrysanthemum rosin (rosin, Arakawa Chemical Industries, Ltd.)
oligomer A: UN-9200A (15000 in molecular weight, urethane methacrylate oligomer, Negami Chemical Industrial Co., Ltd.)
oligomer B: UN-3320HA (1500 in molecular weight, urethane methacrylate oligomer, Negami Chemical Industrial Co., Ltd.)
—Organic Solvent
EtOH: HPLC ethanol (Nacalai Tesque, Inc.)
acetone: HPLC acetone (Nacalai Tesque, Inc.)
—Viscosity Modifier
PVP: polyvinylpyrrolidone (630000 in molecular weight, Tokyo Chemical Industry Co., Ltd.)

The composition and the evaluation result of each varnish composition prepared according to the quantities shown in Tables 4 and 5 are shown in Tables 4 and 5. Each varnish composition was prepared by charging the raw materials into a container and stirring them for 24 hours using a turbula mixer (T2F: Shinmaru Enterprises Corporation) to ensure the dispersion, before put to the test.

TABLE 4

Examples of dental varnish composition

| Component (wt %) | | | Example 7 | Example 8 | Example 9 | Example 10 | Example 11 | Example 12 |
|---|---|---|---|---|---|---|---|---|
| Component (wt %) | Ion sustained-release glass | 1 | 30.0 | — | — | — | 20.0 | — |
| | | 2 | — | 30.0 | — | 30.0 | — | — |
| | | 3 | — | — | 30.0 | — | — | 25.0 |
| | Non-ion sustained-release filler | SOC5 | — | — | — | — | — | — |
| | | NaF | — | — | 5.0 | 5.0 | — | 5.0 |
| | Film component | Rosin A | 40.0 | 45.0 | 35.0 | — | — | 25.0 |
| | | Rosin B | — | — | — | 35.0 | — | — |
| | | Oligomer A | — | — | — | — | 55.0 | — |
| | | Oligomer B | — | — | — | — | — | 15.0 |
| | Organic solvent | EtOH | 30.0 | — | 20.0 | — | 25.0 | 30.0 |
| | | Acetone | — | 25.0 | — | 20.0 | — | — |
| | Viscosity modifier | PVP | — | — | 10.0 | 10.0 | — | — |
| Total | | | 100 | 100 | 100 | 100 | 100 | 100 |
| Element concentration (ppm) | 0~1 hour | F | 3.8 | 2.2 | 6.8 | 6.6 | 4.5 | 7.2 |
| | | Na | 2.4 | 2.6 | 5.6 | 4.3 | 3.4 | 2.6 |
| | | B | 1.8 | 1.3 | 2.2 | 1.8 | 1.9 | 1.9 |
| | | Al | 0.2 | 0.2 | 0.7 | 0.7 | 0.5 | 0.9 |
| | | Sr | 3.3 | 5.1 | 5.5 | 4.4 | 4.8 | 2.5 |
| | 1~2 hour | F | 0.9 | 0.7 | 1.1 | 0.9 | 1.3 | 1.2 |
| | | Na | 0.7 | 1.3 | 2.0 | 3.3 | 1.5 | 2.2 |
| | | B | 0.4 | 0.4 | 0.4 | 0.2 | 0.8 | 0.8 |
| | | Al | 0.2 | 0.2 | 0.2 | 0.2 | 0.3 | 0.4 |
| | | Sr | 1.8 | 1.5 | 2.0 | 1.1 | 2.4 | 2.2 |
| | 2~3 hour | F | 0.7 | 0.7 | 0.7 | 0.9 | 0.8 | 0.8 |
| | | Na | 0.4 | 0.4 | 0.7 | 0.7 | 0.4 | 0.4 |
| | | B | 0.2 | 0.2 | 0.2 | 0.2 | 0.3 | 0.3 |
| | | Al | 0.2 | 0.2 | 0.2 | 0.2 | 0.3 | 0.3 |
| | | Sr | 1.5 | 1.5 | 1.3 | 0.9 | 1.4 | 1.5 |
| Acid neutralizing capacity evaluation | | After 6 hours | 6.3 | 6.2 | 6.3 | 6.3 | 5.9 | 6.0 |
| | | After 24 hours | 6.7 | 6.7 | 6.8 | 6.6 | 6.4 | 6.5 |
| Retentivity of varnish coating | | | ○ | ○ | ○ | ○ | ○ | ○ |
| Foul breath reduction rate (%) | | | 52 | 63 | 69 | 63 | 50 | 59 |

The varnish composition of each of Examples 7 to 12 sustained-released ions not only in the period of 0 to 1 hour but also in the period of 1 to 2 hour and the period of 2 to 3 hour. In addition, the varnish composition exhibited favorable retentivity even after 1000 heat cycles, so that the ions can be sustained-released to the tooth substance for a long time. This is expected to produce the effects such as tooth substance strengthening and secondary caries suppression. Moreover, acid neutralizing capacity evaluation suggests that the varnish composition has high acid neutralizing capacity, as the varnish composition neutralized the lactic acid water solution of pH 4.0 to about pH 6 after 6 hours and to about pH 6.5 after 24 hours. The foul breath suppression evaluation indicates the obvious foul breath suppression effect in the case of applying the varnish composition according to the present invention to the tooth surface.

neutralizing capacity evaluation indicates that Comparative Examples 5 to 8 had no acid neutralizing capacity. Besides, each varnish composition containing a filler that does not have ion sustained releasability had no foul breath suppression effect.

The present invention provides the following various features. The inclusion of the ion sustained-release glass in the dental varnish composition is assumed to significantly improve the strength and thickness of the film formed on the tooth substance, the adhesion of the film to the tooth substance, and the like. Therefore, the dental varnish composition according to the present invention not only improves the retentivity on the tooth substance, but also has excellent effects for healthy oral cavity environment as the fluoride ion is continuously sustained-released in the retention period and influences the strengthening of the tooth

TABLE 5

Comparative examples of dental varnish composition

| | | | Comparative Example 5 | Comparative Example 6 | Comparative Example 7 | Comparative Example 8 |
|---|---|---|---|---|---|---|
| Component (wt %) | Ion sustained-release glass | 1 | — | — | — | — |
| | | 2 | — | — | — | — |
| | | 3 | — | — | — | — |
| | Non-ion sustained-release filler | SOC5 | 30 | — | 35 | — |
| | | NaF | — | 10 | 5 | — |
| | Film component | Rosin A | 50 | — | — | 40 |
| | | Rosin B | — | 60 | — | — |
| | | Oligomer A | — | — | 30 | 15 |
| | | Oligomer B | — | — | — | — |
| | Organic solvent | EtOH | 20 | 20 | 20 | 25 |
| | | Acetone | — | — | — | — |
| | Viscosity modifier | PVP | — | 10 | 10 | 20 |
| | Total | | 100 | 100 | 100 | 100 |
| Element concentration (ppm) | 0~1 hour | F | 0 | 4.8 | 2.4 | 0 |
| | | Na | 0 | 4.2 | 2 | 0 |
| | | B | 0 | 0 | 0 | 0 |
| | | Al | 0 | 0 | 0 | 0 |
| | | Sr | 0 | 0 | 0 | 0 |
| | 1~2 hour | F | 0 | 0.2 | 0.2 | 0 |
| | | Na | 0 | 0 | 0.2 | 0 |
| | | B | 0 | 0 | 0 | 0 |
| | | Al | 0 | 0 | 0 | 0 |
| | | Sr | 0 | 0 | 0 | 0 |
| | 2~3 hour | F | 0 | 0 | 0 | 0 |
| | | Na | 0 | 0 | 0.7 | 0 |
| | | B | 0 | 0 | 0 | 0 |
| | | Al | 0 | 0 | 0 | 0 |
| | | Sr | 0 | 0 | 0 | 0 |
| Acid neutralizing capacity evaluation | After 6 hours | | 4.1 | 4 | 4 | 4 |
| | After 24 hours | | 4.1 | 4.1 | 4.1 | 4.1 |
| Retentivity of varnish coating | | | ◯ | X | ◯ | X |
| Foul breath reduction rate (%) | | | 0 | −1 | 5 | 3 |

Comparative Example 5 containing only silica filler as a filler component had favorable retentivity after the heat cycles, but sustained-released no ion. Comparative Example 6 containing only sodium fluoride as a filler completely dissolved in the period of 0 to 1 hour, and subsequently sustained-released no ion. Besides, since the sodium fluoride completely dissolved, the retentivity of the varnish coating was insufficient. Comparative Example 7 which is the varnish composition containing silica filler and sodium fluoride as a filler had favorable varnish coating retentivity, but sustained-released ions only in the period of 0 to 1 hour, failing to provide the sufficient acid resistance of the tooth substance. Comparative Example 8 containing no filler component not only sustained-released no ion but also had a weak varnish coating, where no varnish coating remained on the tooth substance after 1000 heat cycles. The acid substance, the suppression of secondary caries, the suppression of decalcification, the recalcification, and the like. Moreover, by including specific ion sustained-release glass in the dental varnish composition according to the present invention, it is possible to obtain a new dental varnish composition unlike any conventional dental varnish composition, such as: a rechargeable dental varnish composition that can not only sustained-release various ions including the fluoride ion but also take in various ions from outside and sustained-release the ions again; and a dental varnish composition capable of two-step ion sustained release by including a conventionally used metal fluoride salt so that the synergistic effect of the initial sustained release of a large amount of fluoride ion by the metal fluoride salt and the continuous sustained release of various ions by the ion sustained-release glass can be expected.

Another effect of the present invention is as follows. By the inclusion of the specific ion sustained-release glass, the strontium ion or the aluminum ion is sustained-released in the oral cavity. These ions exhibit an acid neutralizing effect. Accordingly, in the case where the oral cavity environment becomes more acidic, the oral cavity environment can be neutralized. The dental caries suppression effect and the acid buffering capacity effect can thus be expected.

Yet another effect of the present invention is as follows. By the inclusion of the specific ion sustained-release glass, the borate ion is sustained-released in the oral cavity. The antibacterial and bacteriostatic effects of the borate ion can suppress the growth of bacteria, which is effective for the prevention of foul breath, periodontal disease, etc.

(4) Gum Composition

Examples and comparative examples of the gum composition are described below.

The following test methods are used to evaluate the performance of the gum composition prepared in each of the examples and the comparative examples.

[Measurement of Element Content Resulting from Ion Sustained-Released from Gum Composition]

A bovine enamel sample with a diameter of 5 mm and a thickness of 1 mm was attached to a collision section of a mastication tester, 10 ml of distilled water and the tabular gum composition (15 mm×10 mm, about 1.0 g) were added into the chamber, and mechanical mastication was conducted with 30 strokes per minute. The distilled water was exchanged at intervals of 5 minutes, and the mechanical mastication of 15 minutes in total (the distilled water exchanged twice) was carried out. As a result, three solutions including ions released from the gum composition into the distilled water in the period of 0 to 5 minutes, the period of 5 to 10 minutes, and the period of 10 to 15 minutes were obtained. The element content (ion content only in the case of fluoride ion) resulting from each ion in each of these solutions was measured by the same measurement method mentioned above. In the case where the measured elements were not within the calibration, the measurement was conducted with dilution according to need.

[Evaluation of Acid Neutralizing Capacity of Gum Composition]

A polyethylene sample with a diameter of 5 mm and a thickness of 1 mm was attached to a collision section of a mastication tester, 10 ml of a lactic acid water solution (with pH adjusted to 4.0) and the tabular gum composition (15 mm×10 mm, about 1.0 g) were added into the chamber, and mechanical mastication was conducted with 30 strokes per minute. The mechanical mastication was conducted for 15 minutes, and the pH was measured using a pH meter (D-51, HORIBA, Ltd.).

[Evaluation of Foul Breath Suppression Effect]

To evaluate the foul breath suppression effect of each of the examples and the comparative examples, the following test was conducted on 5 persons. Each test subject masticated a tabular gum composition (15 mm×10 mm, about 1.0 g) for 15 minutes, and the breath before the mastication of the gum and the breath after the mastication of the gum were compared for evaluation. In the breath comparison, the sulfur compound concentration (VSC value) in the oral cavity resulting from hydrogen sulfide, methylmercaptan, dimethyl sulfide, etc. in the breath was measured (XP-Breath-Tron, New Cosmos Electric Co., Ltd.), and the value of VSC(1) in the breath before the mastication and the value of VSC(2) in the breath after the mastication for 15 minutes were compared. The foul breath reduction rate=(1−VSC(2)/VSC(1))×100 was calculated based on the evaluation result. The average value of the 5 persons is shown in Tables 7 and 8.

The following shows the names and abbreviations of the components used in the examples of the gum composition according to the present invention and the comparative examples.

—Gum Base Raw Material chicle gutta-percha vinyl acetate resin polyisobutylene micro crystalline wax (Nippon Seiro Co., Ltd.)

ester gum

—Filler

FLX: FUSELEX X (silica filler, average particle diameter=2.1 μm, Tatsumori Ltd.)

SOC5: silica filler (SO-C5, average particle diameter=1.6 μm, Admatechs)

—Fluoride Ion Supply Material

NaF: sodium fluoride powder (Nacalai Tesque, Inc.)

—Sweetener xylitol sucralose cyclodextrin

—Saliva Secretion Promoter citric acid

Each composition shown in Table 7 that includes a gum base A or a gum base B shown in Table 6 was kneaded using a kneader in a state of being heated at 50° C. so as to disperse uniformly, and then molded in tabular form using an extruder. The molded gum composition was further stretched to a thickness of about 2 mm using a stretching machine, and cut to a predetermined size (15 mm×10 mm, about 1.0 g). The evaluation result obtained by testing the cut tabular gum composition is shown in Table 7.

TABLE 6

| | Composition of gum base | | |
|---|---|---|---|
| | Raw material name | Gum base A | Gum base B |
| Blending ratio to gum base | Chicle | 7 | — |
| | Gutta-percha | 3 | — |
| | Vinyl acetate resin | 25 | 60 |
| | Polyisobutylene | 40 | 5 |
| | Micro crystalline wax (Nippon Seiro Co., Ltd.) | 25 | 15 |
| | Ester gum | — | 20 |

TABLE 7

Examples of gum composition

| | | | Example 13 | Example 14 | Example 15 | Example 16 | Example 17 | Example 18 |
|---|---|---|---|---|---|---|---|---|
| Component (wt %) | Ion sustained-release glass | Ion sustained-release glass 1 | 15 | — | — | 10 | — | 5 |
| | | Ion sustained-release glass 2 | — | 15 | — | 20 | 20 | — |
| | | Ion sustained-release glass 3 | — | — | 25 | — | — | 10 |
| | Non-ion sustained-release filler | FLX | 5 | — | — | — | — | — |
| | | SOC5 | — | — | — | — | 5 | — |
| | Gum base | Gum base A | 40 | 50 | 20 | 20 | — | 10 |
| | | Gum base B | — | — | 20 | 20 | 40 | 30 |
| | Fluoride ion supply material | NaF | — | — | — | — | 0.5 | 0.5 |
| | Sweetener | Xylitol | 36.9 | 35 | — | 20 | 34.5 | 40.5 |
| | | Sucralose | — | — | 34 | — | — | — |
| | | Cyclodextrin | 3 | — | 1 | 10 | — | 3.5 |
| | Saliva secretion promoter | Citric acid | 0.1 | — | — | — | — | 0.5 |
| Total | | | 100 | 100 | 100 | 100 | 100 | 100 |
| Element concentration (ppm) | 0~5 minutes | F | 1.6 | 2.9 | 2.8 | 3.5 | 4.5 | 4.8 |
| | | Na | 1.6 | 2.9 | 2.7 | 3.2 | 4.8 | 4.9 |
| | | B | 0.4 | 0.8 | 0.9 | 0.7 | 0.7 | 0.6 |
| | | Al | 0.8 | 1.3 | 1.5 | 1.2 | 1.3 | 1.3 |
| | | Sr | 2.2 | 3.9 | 3.6 | 3.6 | 3.5 | 4 |
| | 5~10 minutes | F | 2 | 3.8 | 3.6 | 3.2 | 3.5 | 3.6 |
| | | Na | 2 | 2.3 | 2.6 | 2.9 | 4.2 | 4.2 |
| | | B | 0.3 | 0.6 | 0.7 | 0.7 | 0.7 | 0.5 |
| | | Al | 0.6 | 0.9 | 1 | 1 | 0.9 | 0.9 |
| | | Sr | 1.9 | 3.5 | 3.6 | 2.8 | 3.1 | 3.9 |
| | 10~15 minutes | F | 1.8 | 3.2 | 3.5 | 3.3 | 3.3 | 3.3 |
| | | Na | 1.2 | 1.8 | 2.1 | 2 | 3.3 | 2.8 |
| | | B | 0.5 | 0.8 | 0.4 | 0.5 | 0.3 | 0.5 |
| | | Al | 0.6 | 0.6 | 1.2 | 1.2 | 1.1 | 0.7 |
| | | Sr | 1.8 | 3.5 | 3.1 | 3.5 | 3.2 | 3.2 |
| Acid neutralizing capacity | After 15 minutes | | 6.4 | 6.7 | 6.5 | 6.6 | 6.6 | 6.5 |
| Foul breath reduction rate (%) | | | 58 | 67 | 74 | 75 | 71 | 59 |

The gum composition of each of Examples 13 to 18 continuously sustained-released the fluoride ion and the strontium ion during mastication. The gum composition also exhibited stable ion sustained releasability with little change in the ion sustained-release amount with time, and so is expected to improve the acid resistance of the tooth substance. Moreover, the acid neutralizing capacity evaluation suggests that the gum composition is effective in the suppression of dental caries, as the mastication for 15 minutes neutralized the lactic acid water solution to pH 6.4 or more, i.e. near neutral. The gum composition of each of Examples 13 to 18 was also found to be effective in the suppression of foul breath, as the mastication of the gum composition contributed to a reduction of foul breath by 58% to 75% as compared with before mastication.

TABLE 8

Comparative examples of gum composition

| | | | Comparative Example 9 | Comparative Example 10 | Comparative Example 11 |
|---|---|---|---|---|---|
| Component (wt %) | Ion sustained-release glass | Ion sustained-release glass 1 | — | — | — |
| | | Ion sustained-release glass 2 | — | — | — |
| | | Ion sustained-release glass 3 | — | — | — |
| | Non-ion sustained-release filler | FLX | 20 | — | — |
| | | SOC5 | — | 20 | — |
| | Gum base | Gum base A | 30 | 40 | — |
| | | Gum base B | 10.5 | — | 49.5 |
| | Fluoride ion supply material | NaF | 0.5 | — | 0.5 |

TABLE 8-continued

| | | | Comparative Example 9 | Comparative Example 10 | Comparative Example 11 |
|---|---|---|---|---|---|
| | Sweetener | Xylitol | 38.9 | 40 | 9.8 |
| | | Suoralose | — | — | 40 |
| | | Cyclodextrin | — | — | 0.2 |
| | Saliva secretion promoter | Citric acid | 0.1 | — | — |
| Total | | | 100 | 100 | 100 |
| Element concentration (ppm) | 0~5 minutes | F | 1.9 | 0 | 1.2 |
| | | Na | 1.9 | 0 | 1.2 |
| | | B | 0 | 0 | 0 |
| | | Al | 0 | 0 | 0 |
| | | Sr | 0 | 0 | 0 |
| | 5~10 minutes | F | 0.3 | 0 | 0.2 |
| | | Na | 0.3 | 0 | 0.2 |
| | | B | 0 | 0 | 0 |
| | | Al | 0 | 0 | 0 |
| | | Sr | 0 | 0 | 0 |
| | 10~15 minutes | F | 0 | 0 | 0 |
| | | Na | 0 | 0 | 0 |
| | | B | 0 | 0 | 0 |
| | | Al | 0 | 0 | 0 |
| | | Sr | 0 | 0 | 0 |
| Acid neutralizing capacity | After 15 minutes | | 4.1 | 4.1 | 4.1 |
| Foul breath reduction rate (%) | | | 12 | 18 | 16 |

Comparative Examples 9 and 11 which are each the gum composition containing only sodium fluoride as an ion supply source sustained-released the fluoride ion, but the sustained release of the fluoride ion was not continuous, so that the improvement of the acid resistance of the tooth substance is hardly expected. Comparative Example 10 which is the gum composition not containing an ion sustained-release glass filler and a fluoride ion supply material sustained-released no ion. This suggests that the gum composition has no effect of improving the acid resistance of the tooth substance and the like. Comparative Examples 9 to 11 were also found to have no acid neutralizing capacity. Comparative Examples 9 to 11 also showed a low foul breath reduction rate of about 20%, and so are not effective in the suppression of foul breath.

(5) Oral Cavity Care Composition

Examples and comparative examples of the oral cavity care composition are described below.

The following test methods are used to evaluate the performance of the oral cavity care composition prepared in each of the examples and the comparative examples.

[Measurement of Element Content Resulting from Ion Sustained-Released from Oral Cavity Care Composition]

3 g of distilled water with respect to 1 g of the oral cavity care composition was charged into a glass container and mixed. Centrifugation (5000 rpm) was performed for 30 minutes at each of three timings, namely, after 3 minutes, after 1 hour, and after 24 hours, and a supernatant liquid was collected. The element concentration of the supernatant liquid was measured by the same method as the above-mentioned [Measurement of element content resulting from ion sustained-released from ion sustained-release glass and each filler]. In the case where the measured elements were not within the calibration, the measurement was conducted with dilution according to need.

[Evaluation of Acid Neutralizing Capacity of Oral Cavity Care Composition]

The oral cavity care composition (0.02 g) was added in a lactic acid water solution (20 mL, pH=4.0), and the temporal pH change in the lactic acid water solution was measured using a pH meter (pH METER F-22, HORIBA, Ltd.).

[Evaluation of Paste Property of Oral Cavity Care Composition]

The oral cavity care composition was collected on a mixing sheet and spread with a spatula, and whether or not the paste property is uniform was checked.

Each oral cavity care composition was prepared according to the composition shown in Table 9. The result of evaluation using the oral cavity care composition is shown in Table 10.

TABLE 9

| | | | | Composition of oral cavity care composition | | | | | | |
|---|---|---|---|---|---|---|---|---|---|---|
| | | | Example 19 | Example 20 | Example 21 | Example 22 | Example 23 | Comparative Example 12 | Comparative Example 13 | Comparative Example 14 |
| Component (wt %) | Ion sustained-release glass 1 | | 1 | — | — | — | — | — | — | — |
| | Ion sustained-release glass 2 | | — | 1 | — | 5 | 30 | — | — | — |
| | Ion sustained-release glass 3 | | — | — | 1 | — | — | — | — | — |
| | Other filler | SOC5 | — | — | — | — | — | — | 30 | — |
| | | NaF | — | — | — | — | — | — | — | 0.2 |

TABLE 9-continued

Composition of oral cavity care composition

|  |  | Example 19 | Example 20 | Example 21 | Example 22 | Example 23 | Comparative Example 12 | Comparative Example 13 | Comparative Example 14 |
|---|---|---|---|---|---|---|---|---|---|
| Abrasive | Silicic anhydride | 20 | 20 | 20 | 18 | 5 | 21 | 5 | 10 |
|  | Calcium carbonate | — | — | — | — | — | — | — | 10 |
| Thickener | Carboxymethyl-cellulose | 1.4 | 1.4 | 1.4 | 1.1 | 1 | 1.5 | 1.5 | 1.5 |
| Humectant | Glycerin | 15 | 15 | 15 | 15 | 15 | 15 | 15 | 15 |
|  | Sorbit liquid | 30 | 30 | 30 | 30 | 30 | 30 | 30 | 30 |
| pH adjuster | Sodium hydroxide | 0.2 | 0.2 | 0.2 | 0.2 | 0.2 | 0.2 | 0.2 | 0.2 |
|  | Sodium citrate | 0.4 | 0.4 | 0.4 | 0.4 | 0.4 | 0.4 | 0.4 | 0.4 |
| Foaming agent | Sodium laurylsulfate | 1 | 1 | 1 | 1 | 1 | 1 | 1 | 1 |
| Solubilizer | Polyoxyethylene hardened castor oil | 0.5 | 0.5 | 0.5 | 0.5 | 0.5 | 0.5 | 0.5 | 0.5 |
| Sweetener | Dipotassium glycyrrhizinate | 0.1 | 0.1 | 0.1 | 0.1 | 0.1 | 0.1 | 0.1 | 0.1 |
| Solvent | Purified water | Proper quantity | Proper quantity | Proper quantity | Proper quantity | Proper quantity | Proper quantity | Proper quantity | Proper quantity |
| Total |  | 100 | 100 | 100 | 100 | 100 | 100 | 100 | 100 |

TABLE 10

Evaluation result of oral cavity care composition

|  |  |  | Example 19 | Example 20 | Example 21 | Example 22 | Example 23 | Comparative Example 12 | Comparative Example 13 | Comparative Example 14 |
|---|---|---|---|---|---|---|---|---|---|---|
| Element concentration (ppm) | After 3 minutes | F | 110.2 | 180.7 | 154.3 | 180.2 | 144.3 | 0 | 0 | 72.1 |
|  |  | Na | 840.5 | 880.1 | 890.2 | 874.2 | 872.2 | 840.5 | 874.2 | 902.3 |
|  |  | B | 40.8 | 63.2 | 65.2 | 210.2 | 510.2 | 0 | 0 | 0 |
|  |  | Al | 50.2 | 75.4 | 80.2 | 160.2 | 153.4 | 0 | 0 | 0 |
|  |  | Sr | 190.2 | 290.4 | 285.5 | 450.2 | 850.2 | 0 | 0 | 0 |
|  | After 1 hour | F | 161.1 | 250.2 | 230.2 | 304.2 | 234.2 | 0 | 0 | 85.4 |
|  |  | Na | 985.2 | 1214.1 | 1180.1 | 1123.2 | 1224.5 | 985.2 | 952.3 | 1100.2 |
|  |  | B | 53.3 | 80.5 | 82.3 | 350.2 | 802.2 | 0 | 0 | 0 |
|  |  | Al | 78 | 119.2 | 120.5 | 290.2 | 274.2 | 0 | 0 | 0 |
|  |  | Sr | 247.4 | 380.2 | 390.2 | 790.2 | 1353.2 | 0 | 0 | 0 |
|  | After 24 hours | F | 189.7 | 278 | 248 | 323.5 | 245.5 | 0 | 0 | 98.4 |
|  |  | Na | 1201.2 | 1317.2 | 1315.6 | 1324.1 | 1462.9 | 1201.2 | 1229.1 | 1302.2 |
|  |  | B | 55.3 | 85.6 | 85.5 | 409.6 | 1006.4 | 0 | 0 | 0 |
|  |  | Al | 87.2 | 130.2 | 135.7 | 317.2 | 297.9 | 0 | 0 | 0 |
|  |  | Sr | 290.2 | 481.5 | 481.2 | 816 | 1560.8 | 0 | 0 | 0 |
| Acid neutralizing capacity evaluation | After 3 minutes |  | 4.6 | 4.6 | 4.7 | 5.3 | 5.3 | 4.1 | 4.1 | 4.2 |
|  | After 24 hours |  | 5.2 | 5.3 | 5.3 | 6.1 | 6.7 | 4.3 | 4.4 | 4.4 |
| Paste property evaluation | Initial |  | Uniform | Uniform | Uniform | Uniform | Uniform | Uniform | Uniform | Uniform |
|  | After 2 months at 50° C. |  | Uniform | Uniform | Uniform | Uniform | Uniform | Uniform | Uniform | Not uniform and coarse |
| Foul breath reduction rate (%) |  |  | 58 | 52 | 63 | 58 | 72 | 25 | 23 | 16 |

As shown in Table 10, the oral cavity care composition of each of Examples 19 to 23 sustained-released various elements such as fluorine, aluminum, sodium, strontium, and boron. The comparison of the sustained-release amounts of each element after 3 minutes, after 1 hour, and after 24 hours reveals that the sustained-release amount increased with time. This indicates that each element was continuously sustained-released. Moreover, the acid neutralizing capacity evaluation reveals that the oral cavity care composition of each of Examples 19 to 23 has an acid neutralizing capacity, as the pH of the lactic acid water solution increased from 4.0 to 4.6 or more after 3 minutes and exceeded 5.1 after 24 hours. This is expected to produce the effect of dental caries suppression. Further, even after stored at 50° C. for 2 months, the oral cavity care composition of Example 19 had the same paste property as immediately after manufacture. This indicates that, while various ions are sustained-released into the water from the ion sustained-release glass during storage to saturation, there is no precipitation of a reaction product caused by the reaction of components and so excellent storage stability is attained.

On the other hand, the oral cavity care composition of Comparative Example 12 not containing ion sustained-release glass and a filler eluted only elemental sodium resulting from a component other than ion sustained-release glass. Besides, the pH after 24 hours in the acid neutralizing capacity evaluation was about 4.3, indicating that the oral cavity care composition has no acid neutralizing capacity. The oral cavity care composition of Comparative Example 13 containing SOC5 instead of ion sustained-release glass showed the same result as Comparative Example 12 because SOC5 lacks ion sustained releasability. The oral cavity care composition eluted only elemental sodium resulting from a component other than ion sustained-release glass, and had no acid neutralizing capacity. The oral cavity care composition of Comparative Example 14 containing sodium fluoride and calcium carbonate lost uniform paste property after stored at 50° C. for 2 months, and thus has a problem with storage stability. This is probably because the calcium ion sustained-released from the calcium carbonate and the fluoride ion sustained-released from the sodium fluoride reacted with each other and as a result an insoluble material was generated and precipitated. Besides, the pH after 24 hours in the acid neutralizing capacity evaluation was about 4.3, indicating that the oral cavity care composition has no acid neutralizing capacity.

To evaluate the foul breath suppression effect of each of the examples and the comparative examples, the following test was conducted on 5 persons. The oral cavity of each test subject 20 years of age or older whose 28 teeth except wisdom teeth are all healthy was cleaned for 3 minutes using the oral cavity care composition, and the breath after the cleaning was compared with the breath before the cleaning for evaluation. In the breath comparison, the sulfur compound concentration (VSC value) in the oral cavity resulting from hydrogen sulfide, methylmercaptan, dimethyl sulfide, etc. in the breath was measured (XP-Breath-Tron, New Cosmos Electric Co., Ltd.), and the value of VSC(1) in the breath before the application and the value of VSC(2) in the breath 2 hours after the application were compared. The foul breath reduction rate $(\%)=(1-VSC(2)/VSC(1))\times 100$ was calculated based on the evaluation result. The average value of the 5 persons is shown in Table 10.

The oral cavity care composition of each of Examples 19 to 23 achieved a reduction in VSC value by 52% to 72%, indicating that the oral cavity care composition is effective in foul breath suppression. The oral cavity care composition of each of Comparative Examples 12 to 14 showed no significant VSC change as compared with Examples 19 to 23, and so has little foul breath suppression effect.

(6) Thermoplastic Sheet Composition

Examples and comparative examples of the thermoplastic sheet composition are described below.

The following test methods are used to evaluate the performance of the thermoplastic sheet composition prepared in each of the examples and the comparative examples.

[Measurement of Element Content Resulting from Ion Sustained-Released from Thermoplastic Sheet Composition]

The thermoplastic sheet composition was molded in round plate form ($\varphi 20 \times 2$ mm). The round plate sample was immersed in 9.4 mL of distilled water, and taken out after 1 day. The element content resulting from each ion in the extraction solution was measured by the same measurement method mentioned above.

[Evaluation of Acid Neutralizing Capacity of Thermoplastic Sheet Composition]

The thermoplastic sheet composition was molded in round plate form ($\varphi 20 \times 2$ mm). The round plate sample was immersed in 9.4 mL of a lactic acid water solution with pH adjusted to 4.0. The pH of the lactic acid water solution after 24 hours was measured using a pH meter (D-51, HORIBA, Ltd.) for evaluation.

[Evaluation of Molding Lower Limit Temperature of Thermoplastic Sheet Composition]

The thermoplastic sheet composition heated at 100° C. to 200° C. with 10° C. intervals was used to mold an intraorally worn device. The temperature measurement position was the center of the lower surface of the thermoplastic sheet composition, and the temperature was measured using a non-contact thermometer. Whether or not the mold is acceptable was determined in such a manner that the case where the interdental papillae (three portions that are between the central incisors, between the first and second right molars, and between the first and second left molars) of a dentition model are clearly marked on the molded intraorally worn device is acceptable and the case where the interdental papillae are not clearly marked on the molded intraorally worn device is not acceptable. The lowest molding temperature from among the cases determined as acceptable according to this technique was set as the molding lower limit temperature.

[Evaluation of Conformity of Intraorally Worn Device Molded Using Thermoplastic Sheet Composition]

An intraorally worn device was molded using each type of thermoplastic sheet composition. The molding temperature of each type of thermoplastic sheet composition was the molding lower limit temperature evaluated in the above-mentioned test. While attaching the molded intraorally worn device to a gypsum model, the center part of the first right molar was cut in the buccolingual direction. The clearance between the gypsum model and the intraorally worn device in the molar fissure of the cut surface was measured using a digital microscope VH-8000 (Keyence Corporation).

The following shows the names and abbreviations of the components used in the examples of the thermoplastic sheet composition according to the present invention and the comparative examples.

SOC5: silica filler "Admafine SO-C5" (Admatechs)
NaF: sodium fluoride powder (Nacalai Tesque, Inc.)
EVAFLEX EV360: ethylene-vinyl acetate copolymer (Du Pont-Mitsui Chemical Co., Ltd.)

[Mouthguard Thermoplastic Sheet]

Example 24

Mouthguard Thermoplastic Sheet 1

2000 g of EVAFLEX EV360 and 500 g of the ion sustained-release glass 1 were charged into a pressure kneader, and mixed at 110° C. for 10 minutes to obtain a mixture of the ion sustained-release glass and the ethylene-vinyl acetate copolymer. The mixture was wound around a 7-inch oven roll increased to 100° C. beforehand, and processed in sheet form. The sheet workpiece was packed in a mold (300×300×4 mm), and pressure molded at 160° C. for 5 minutes and then cooled to obtain the mouthguard thermoplastic sheet 1.

Example 25

Mouthguard Thermoplastic Sheet 2

The mouthguard thermoplastic sheet 2 was obtained in the same way as Example 24, except that 2000 g of EVAFLEX EV360 and 500 g of the ion sustained-release glass 2 were used.

Example 26

Mouthguard Thermoplastic Sheet 3

The mouthguard thermoplastic sheet 3 was obtained in the same way as Example 24, except that 2000 g of EVAFLEX EV360 and 500 g of the ion sustained-release glass 3 were used.

Example 27

Mouthguard Thermoplastic Sheet 4

The mouthguard thermoplastic sheet 4 was obtained in the same way as Example 24, except that 1500 g of EVAFLEX EV360 and 1000 g of the ion sustained-release glass 3 were used.

Comparative Example 15

Mouthguard Thermoplastic Sheet 5

The mouthguard thermoplastic sheet 5 was obtained in the same way as Example 24, except that 2500 g of EVAFLEX EV360 was used.

Comparative Example 16

Mouthguard Thermoplastic Sheet 6

The mouthguard thermoplastic sheet 6 was obtained in the same way as Example 24, except that 2000 g of EVAFLEX EV360 and 500 g of NaF were used.

Comparative Example 17

Mouthguard Thermoplastic Sheet 7

The mouthguard thermoplastic sheet 7 was obtained in the same way as Example 24, except that 2000 g of EVAFLEX EV360 and 500 g of SOC5 were used.

[Splint Thermoplastic Sheet]

Example 28

Splint Thermoplastic Sheet 1

2000 g of polyethylene terephthalate and 500 g of the ion sustained-release glass 1 were charged into a pressure kneader, and mixed at 200° C. for 30 minutes to obtain a mixture of the ion sustained-release glass and the polyethylene terephthalate. The mixture was processed in sheet form with a thickness of 1 mm by an extruder. The sheet workpiece was cut to 300×300×1 mm to obtain the splint thermoplastic sheet 1.

Example 29

Splint Thermoplastic Sheet 2

The splint thermoplastic sheet 2 was obtained in the same way as Example 28, except that 2000 g of polyethylene terephthalate and 500 g of the ion sustained-release glass 2 were used.

Example 30

Splint Thermoplastic Sheet 3

The splint thermoplastic sheet 3 was obtained in the same way as Example 28, except that 2000 g of polyethylene terephthalate and 500 g of the ion sustained-release glass 3 were used.

Example 31

Splint Thermoplastic Sheet 4

The splint thermoplastic sheet 4 was obtained in the same way as Example 28, except that 1500 g of polyethylene terephthalate and 1000 g of the ion sustained-release glass 3 were used.

Comparative Example 18

Splint Thermoplastic Sheet 5

The splint thermoplastic sheet 5 was obtained in the same way as Example 28, except that 2000 g of polyethylene terephthalate was used.

Comparative Example 19

Splint Thermoplastic Sheet 6

The splint thermoplastic sheet 6 was obtained in the same way as Example 28, except that 2000 g of polyethylene terephthalate and 500 g of NaF were used.

Comparative Example 20

Splint Thermoplastic Sheet 7

The splint thermoplastic sheet 7 was obtained in the same way as Example 28, except that 2500 g of polyethylene terephthalate and 500 g of SOC5 was used.

The evaluation result of each mouthguard thermoplastic sheet composition is shown in Table 11, and the evaluation result of each splint thermoplastic sheet composition is shown in Table 12.

TABLE 11

Evaluation result of mouthguard thermoplastic sheet composition

| | | | Example 24 | Example 25 | Example 26 | Example 27 | Comparative Example 15 | Comparative Example 16 | Comparative Example 17 |
|---|---|---|---|---|---|---|---|---|---|
| Element concentration (ppm) | After 1 day | F | 0.22 | 0.52 | 0.4 | 0.6 | 0 | 9.32 | 0 |
| | | Na | 0.13 | 0.21 | 0.24 | 0.3 | 0 | 10.12 | 0 |
| | | B | 0.31 | 0.53 | 0.74 | 1.38 | 0 | 0 | 0 |
| | | Al | 0.02 | 0.04 | 0.03 | 0.06 | 0 | 0 | 0 |
| | | Sr | 0.28 | 0.78 | 0.61 | 0.92 | 0 | 0 | 0 |
| | After 7 days | F | 0.33 | 0.6 | 0.45 | 0.92 | 0 | 9.18 | 0 |
| | | Na | 0.18 | 0.21 | 0.3 | 0.41 | 0 | 9.84 | 0 |
| | | B | 0.82 | 1.2 | 1.92 | 2.87 | 0 | 0 | 0 |
| | | Al | 0.07 | 0.08 | 0.06 | 0.1 | 0 | 0 | 0 |
| | | Sr | 0.38 | 0.87 | 1.09 | 1.58 | 0 | 0 | 0 |

TABLE 11-continued

Evaluation result of mouthguard thermoplastic sheet composition

|  | Example 24 | Example 25 | Example 26 | Example 27 | Comparative Example 15 | Comparative Example 16 | Comparative Example 17 |
|---|---|---|---|---|---|---|---|
| Acid neutralizing capacity (pH) | 5.7 | 6.3 | 5.9 | 6.1 | 4 | 4 | 4 |
| Conformity with F2 > F1 (Expression 1) | Conforming | Conforming | Conforming | Conforming | Nonconforming | Nonconforming | Nonconforming |
| Molding lower limit temperature (° C.) | 110 | 110 | 110 | 110 | 160 | 160 | 130 |
| Compatibility (μm) | 221 | 266 | 216 | 193 | 421 | 457 | 374 |
| Foul breath reduction rate (%) | 31 | 42 | 37 | 46 | 0 | 0 | 0 |

[Ion Sustained Releasability and Acid Neutralizing Capacity of Mouthguard Thermoplastic Sheet Composition]

The lactic acid water solution (pH 4.0) in which the mouthguard thermoplastic sheet composition containing the ion sustained-release glass (Examples 24 to 27) was immersed increased in pH after 24 hours, indicating that the mouthguard thermoplastic sheet composition has the acid neutralizing capacity. The lactic acid water solution (pH 4.0) in which the mouthguard thermoplastic sheet composition containing the non-ion sustained-release filler (Comparative Examples 15 to 17) was unchanged in pH after 24 hours, indicating that the mouthguard thermoplastic sheet composition does not have the acid neutralizing capacity.

The element content (ion content only in the case of fluoride ion) sustained-released from the mouthguard thermoplastic sheet composition containing the ion sustained-release glass (Examples 24 to 27) conformed to Expression (1). The element content (ion content only in the case of fluoride ion) sustained-released from the mouthguard thermoplastic sheet composition containing the non-ion sustained-release filler (Comparative Examples 15 to 17) did not conform to Expression (1).

[Molding Lower Limit Temperature and Compatibility of Mouthguard Thermoplastic Sheet Composition]

The mouthguard thermoplastic sheet composition containing the ion sustained-release glass (Examples 24 to 27) had a low molding lower limit temperature upon molding and excellent compatibility between the molded intraorally worn device and the gypsum mold, as compared with the mouthguard thermoplastic sheet composition containing the non-ion sustained-release filler (Comparative Examples 15 to 17).

[Evaluation of Foul Breath Suppression Effect of Mouthguard Thermoplastic Sheet Composition]

Purpose: To evaluate the foul breath suppression effect of the mouthguard thermoplastic sheet composition.

Method: To evaluate the foul breath suppression effect of each of the examples and the comparative examples, the following test was conducted on 5 persons. A mouthguard was made using the mouthguard thermoplastic sheet composition according to the present invention. Each test subject wore the mouthguard, and kept it for 5 hours without drinking and eating. The breath before wearing the mouthguard and the breath after wearing the mouthguard for 5 hours were compared for evaluation. In the breath comparison, the sulfur compound concentration (VSC value) in the oral cavity resulting from hydrogen sulfide, methylmercaptan, dimethyl sulfide, etc. in the breath was measured (XP-Breath-Tron, New Cosmos Electric Co., Ltd.), and the value of VSC(1) in the breath before wearing the mouthguard and the value of VSC(2) in the breath after wearing the mouthguard for 5 hours were compared. The foul breath reduction rate=(1−VSC(2)/VSC(1))×100 was calculated based on the evaluation result, from which the average value of the 5 persons is calculated.

The mouthguard thermoplastic sheet composition of each of Examples 24 to 27 showed a decrease in VSC value, indicating that the mouthguard thermoplastic sheet composition is effective in the suppression of foul breath. The mouthguard thermoplastic sheet composition of each of Comparative Examples 15 to 17 showed substantially no change in VSC value, indicating that the mouthguard thermoplastic sheet composition does not have the foul breath suppression effect.

TABLE 12

Splint thermoplastic sheet composition

|  |  |  | Example 28 | Example 29 | Example 30 | Example 31 | Comparative Example 18 | Comparative Example 19 | Comparative Example 20 |
|---|---|---|---|---|---|---|---|---|---|
| Element concentration (ppm) | After 1 day | F | 0.14 | 0.47 | 0.33 | 0.55 | 7.1 | 8.26 | 0 |
| | | Na | 0.09 | 0.18 | 0.15 | 0.19 | 0 | 8.81 | 0 |
| | | B | 0.23 | 0.47 | 0.38 | 0.82 | 0 | 0 | 0 |
| | | Al | 0.01 | 0.02 | 0.02 | 0.04 | 0 | 0 | 0 |
| | | Sr | 0.18 | 0.61 | 0.53 | 0.72 | 0 | 0 | 0 |
| | After 7 days | F | 0.22 | 0.65 | 0.46 | 0.91 | 0 | 8.47 | 0 |
| | | Na | 0.15 | 0.25 | 0.19 | 0.31 | 0 | 8.93 | 0 |
| | | B | 0.51 | 0.92 | 0.71 | 1.48 | 0 | 0 | 0 |
| | | Al | 0.03 | 0.05 | 0.03 | 0.07 | 0 | 0 | 0 |
| | | Sr | 0.35 | 1.23 | 1.18 | 1.65 | 0 | 0 | 0 |
| Acid neutralizing capacity (pH) | | | 5.5 | 6 | 5.8 | 5.9 | 4 | 4 | 4 |
| Conformity with F2 > F1 (Expression 1) | | | Conforming | Conforming | Conforming | Conforming | Nonconforming | Nonconforming | Nonconforming |
| Molding lower limit temperature (° C.) | | | 120 | 120 | 120 | 120 | 140 | 140 | 130 |
| Compatibility (μm) | | | 167 | 143 | 185 | 134 | 388 | 351 | 318 |
| Foul breath reduction rate (%) | | | 24 | 37 | 29 | 41 | 0 | 0 | 0 |

[Ion Sustained Releasability and Acid Neutralizing Capacity of Splint Thermoplastic Sheet Composition]

The lactic acid water solution (pH 4.0) in which the splint thermoplastic sheet composition containing the ion sustained-release glass (Examples 28 to 31) was immersed increased in pH after 24 hours, indicating that the mouthguard thermoplastic sheet composition has the acid neutralizing capacity. The lactic acid water solution (pH 4.0) in which the splint thermoplastic sheet composition containing the non-ion sustained-release filler (Comparative Examples 18 to 20) was unchanged in pH after 24 hours, indicating that the mouthguard thermoplastic sheet composition does not have the acid neutralizing capacity.

The element content (ion content only in the case of fluoride ion) sustained-released from the splint thermoplastic sheet composition containing the ion sustained-release glass (Examples 28 to 31) conformed to Expression (1). The element content (ion content only in the case of fluoride ion) sustained-released from the splint thermoplastic sheet composition containing the non-ion sustained-release filler (Comparative Examples 18 to 20) did not conform to Expression (1).

[Molding Lower Limit Temperature and Compatibility of Splint Thermoplastic Sheet Composition]

The splint thermoplastic sheet composition containing the ion sustained-release glass (Examples 28 to 31) had a low molding lower limit temperature upon molding and excellent compatibility between the molded intraorally worn device and the gypsum mold, as compared with the splint thermoplastic sheet composition containing the non-ion sustained-release filler (Comparative Examples 18 to 20).

[Evaluation of Foul Breath Suppression Effect of Splint Thermoplastic Sheet Composition]

Purpose: To evaluate the foul breath suppression effect of the splint thermoplastic sheet composition.

Method: To evaluate the foul breath suppression effect of each of the examples and the comparative examples, the following test was conducted on 5 persons. A splint was made using the splint thermoplastic sheet composition according to the present invention. Each test subject wore the splint, and kept it for 5 hours without drinking and eating. The breath before wearing the splint and the breath after wearing the splint for 5 hours were compared for evaluation. In the breath comparison, the sulfur compound concentration (VSC value) in the oral cavity resulting from hydrogen sulfide, methylmercaptan, dimethyl sulfide, etc. in the breath was measured (XP-Breath-Tron, New Cosmos Electric Co., Ltd.), and the value of VSC(1) in the breath before wearing the splint and the value of VSC(2) in the breath after wearing the splint for 5 hours were compared. The foul breath reduction rate=$(1-VSC(2)/VSC(1))\times 100$ was calculated based on the evaluation result.

The splint thermoplastic sheet composition of each of Examples 28 to 31 showed a decrease in VSC value, indicating that the mouthguard thermoplastic sheet composition is effective in the suppression of foul breath. The splint thermoplastic sheet composition of each of Comparative Examples 18 to 20 showed substantially no change in VSC value, indicating that the mouthguard thermoplastic sheet composition does not have the foul breath suppression effect.

(7) Two-Component Mixture Ion Sustained-Release Denture Base-Related Material Composition Examples and comparative examples of the two-component mixture ion sustained-release denture base-related material composition are described below.

The following test methods are used to evaluate the performance of the two-component mixture ion sustained-release denture base-related material composition prepared in each of the examples and the comparative examples.

[Machinability of Two-Component Mixture Ion Sustained-Release Denture Base-Related Material Composition]

Purpose: To evaluate the machinability of the hardened material of the two-component mixture ion sustained-release denture base-related material composition.

Method: The powder material and the liquid material of the two-component mixture ion sustained-release denture base-related material composition according to the present invention were mixed and swollen at the ratio of 2:1 so as to be changed into a state called a rice cake-like resin, and then packed into a stainless steel mold ($20\varphi\times 2$ mm: discoid). Polymerization was then performed under the condition according to the purpose of use, to form a sample. The sample was cut by a technical carbide bur, and the machinability was evaluated in the following four levels.

A: Machinability is very good and the operation does not take time.

B: Machinability is good, but the hardened material of the denture base resin slightly sticks to the grinder.

C: Cutting is difficult as the hardened material of the denture base resin sticks to the grinder.

D: Cutting takes time, and the denture surface increases to high temperature.

[Surface Hardness of Two-Component Mixture Ion Sustained-Release Denture Base-Related Material Composition]

Purpose: To evaluate the surface hardness of the hardened material of the two-component mixture ion sustained-release denture base-related material composition.

Method: The powder material and the liquid material of the two-component mixture ion sustained-release denture base-related material composition according to the present invention were mixed and swollen at the ratio of 2:1 so as to be changed into a state called a rice cake-like resin, and then packed into a stainless steel mold ($15\varphi\times 1$ mm: discoid). Polymerization was then performed under the condition according to the purpose of use, to form a sample. The Vickers hardness of the sample surface was measured using a micro Vickers hardness tester (HM-102, Mitutoyo Corporation).

[Measurement and Evaluation of Fluorine Release Amount from Two-Component Mixture Ion Sustained-Release Denture Base-Related Material Composition]

Purpose: To evaluate the fluorine release property from the hardened material of the two-component mixture ion sustained-release denture base-related material composition.

Method: The powder material and the liquid material of the two-component mixture ion sustained-release denture base-related material composition according to the present invention were mixed and swollen at the ratio of 2:1 so as to be changed into a state called a rice cake-like resin, and then packed into a stainless steel mold ($15\varphi\times 1$ mm: discoid). Polymerization was then performed under the condition according to the purpose of use, to form a sample. The sample was put in a plastic container including 5 mL of distilled water, and sealed and left in a 37° C. incubator for 1 week. The container was taken out of the incubator after 1 week, and the amount of fluorine eluted from the discoid sample was measured using a fluoride ion composite electrode (Model 9609, Orion Research Inc.) and an ion meter (Model 720A, Orion Research Inc.). Upon measurement, 0.5 ml of TISABIII (Orion Research Inc.) was added as an ionic strength adjuster. Calibration was performed using standard solutions of 0.02 ppm, 0.1 ppm, 1 ppm, 10 ppm, and 50 ppm. The fluorine release amount is preferably greater than or equal to 0.2 ppm, and more preferably greater than or equal to 0.5 ppm.

[Measurement and Evaluation of Ion Release Amount from Two-Component Mixture Ion Sustained-Release Denture Base-Related Material Composition]

Purpose: To evaluate the ion release property from the hardened material of the two-component mixture ion sustained-release denture base-related material composition.

Method: The powder material and the liquid material of the two-component mixture ion sustained-release denture base-related material composition according to the present invention were mixed and swollen at the ratio of 2:1 so as to be changed into a state called a rice cake-like resin, and then packed into a stainless steel mold (15φ×1 mm: discoid). Polymerization was then performed under the condition according to the purpose of use, to form a sample. The sample was put in a plastic container including 5 mL of distilled water, and sealed and left in a 37° C. incubator for 1 week. The container was taken out of the incubator after 1 week, and the amount of ion eluted from the discoid sample was measured using an ICP emission spectrometer. Each metal ion amount was converted using calibration obtained from standard samples (1 ppm, 2.5 ppm, 5 ppm, 10 ppm) of the ion.

[Evaluation of Acid Neutralizing Capacity of Two-Component Mixture Ion Sustained-Release Denture Base-Related Material Composition]

Purpose: To evaluate the acid neutralizing capacity of the two-component mixture ion sustained-release denture base-related material composition.

Method: The powder material and the liquid material of the two-component mixture ion sustained-release denture base-related material composition according to the present invention were mixed and swollen at the ratio of 2:1 so as to be changed into a state called a rice cake-like resin, and then packed into a stainless steel mold (15φ×1 mm: discoid). Polymerization was then performed under the condition according to the purpose of use, to form a sample. The sample was immersed in 5 mL of a lactic acid water solution (pH adjusted to 4.0). The pH of the lactic acid water solution after 6 hours and after 24 hours was measured using a pH meter (D-51, HORIBA, Ltd.).

[Evaluation of Foul Breath Suppression Effect of Two-Component Mixture Ion Sustained-Release Denture Base-Related Material Composition]

Purpose: To evaluate the foul breath suppression effect of the two-component mixture ion sustained-release denture base-related material composition.

Method: To evaluate the foul breath suppression effect of each of the examples and the comparative examples, the following test was conducted on 5 persons. The powder material and the liquid material of the two-component mixture ion sustained-release denture base-related material composition according to the present invention were mixed and swollen at the ratio of 2:1 so as to be changed into a state called a rice cake-like resin, and then packed into a stainless steel mold (15φ×0.5 mm: discoid). Polymerization was then performed under the condition according to the purpose of use, to form a sample. The sample was fixed to the palatine portion, and kept for 5 hours without drinking and eating. The breath before attaching the sample and the breath after attaching the sample for 5 hours were compared for evaluation. In the breath comparison, the sulfur compound concentration (VSC value) in the oral cavity resulting from hydrogen sulfide, methylmercaptan, dimethyl sulfide, etc. in the breath was measured (XP-Breath-Tron, New Cosmos Electric Co., Ltd.), and the value of VSC(1) in the breath before attaching the sample and the value of VSC(2) in the breath after attaching the sample for 5 hours were compared. The foul breath reduction rate=(1−VSC(2)/VSC(1))×100 was calculated based on the evaluation result, from which the average value of the 5 persons is calculated.

[Polymerization Condition According to Purpose of Use]

Denture base resin: Under the pressure condition of 2.0 t, heating was performed at 70° C. for 30 minutes, and then heating was performed at 100° C. for 30 minutes.

Lining material: Cover glass was placed on both surfaces to apply pressure with glass mixing plates and then left at ambient temperature for 30 minutes, and subsequently immersed in a hardening accelerator water solution of 50° C. to 60° C. for 10 minutes.

Quick cure resin: Cover glass was placed on both surfaces to apply pressure with glass mixing plates, and then left at ambient temperature for 30 minutes.

Base orthodontic resin: Cover glass was placed on both surfaces to apply pressure with glass mixing plates and then left at ambient temperature for 30 minutes, and subsequently immersed in warm water of 50° C. to 60° C. for 30 minutes.

The following shows the names and abbreviations of the components used in the examples of the present invention and the comparative examples.

PMMA100: polymethyl methacrylate (average particle diameter (D50): 100 μm, weight-average molecular weight: 900000, shape: spherical)

PMMA100L: polymethyl methacrylate (average particle diameter (D50): 100 μm, weight-average molecular weight: 400000, shape: spherical)

PMMA100H: polymethyl methacrylate (average particle diameter (D50): 100 μm, weight-average molecular weight: 1700000, shape: spherical)

PEMA40: polyethyl methacrylate (average particle diameter (D50): 40 μm, weight-average molecular weight: 650000, shape: spherical)

PEMA40L: polyethyl methacrylate (average particle diameter (D50): 40 μm, weight-average molecular weight: 350000, shape: spherical)

PEMA4OH: polyethyl methacrylate (average particle diameter (D50): 40 μm, weight-average molecular weight: 1600000, shape: spherical)

Copolymer 50: copolymer of MMA/EMA=50/50 (average particle diameter (D50): 70 μm, weight-average molecular weight: 600000, shape: spherical)

Copolymer 50L: copolymer of MMA/EMA=50/50 (average particle diameter (D50): 70 μm, weight-average molecular weight: 300000, shape: spherical)

Copolymer 50H: copolymer of MMA/EMA=50/50 (average particle diameter (D50): 70 μm, weight-average molecular weight: 1550000, shape: spherical)

Copolymer 80: copolymer of MMA/EMA=80/20 (average particle diameter (D50): 65 μm, weight-average molecular weight: 500000, shape: spherical)

Copolymer 80L: copolymer of MMA/EMA=80/20 (average particle diameter (D50): 65 μm, weight-average molecular weight: 400000, shape: spherical)

Copolymer 80H: copolymer of MMA/EMA=80/20 (average particle diameter (D50): 65 μM, weight-average molecular weight: 1800000, shape: spherical)
F1: ion sustained-release glass 1
F2: ion sustained-release glass 2
F3: ion sustained-release glass 3
MMA: methyl methacrylate
MMES: methyl methacryloyloxyethylsuccinate
BPO: benzoyl peroxide
DMPT: p-N,N-dimethyl-toluidine
1 G: ethyleneglycol dimethacrylate
HX: 1,6-hexanedioldimethacrylate
EtOH: ethanol
PMMA-C: crosslinked polymethyl methacrylate (polymethyl methacrylate made up of 95 parts MMA and 5 parts 1 G, average particle diameter (D50): 10 μm, shape: spherical)

TABLE 13

| | Powder material composition | | | | | | | | | |
|---|---|---|---|---|---|---|---|---|---|---|
| | (I) Noncrosslinked (meth)acrylate polymer | | | | | | | | | |
| | PMMA 100 | PMMA 100L | PMMA 100H | PEMA 40 | PEMA 40L | PEMA 40H | Copolymer 50 | Copolymer 50L | Copolymer 50H | Copolymer 80 |
| P1  | 90  | —   | —   | —   | —  | —  | —   | —   | —   | —   |
| P2  | 80  | —   | —   | —   | —  | —  | —   | —   | —   | —   |
| P3  | 80  | —   | —   | —   | —  | —  | —   | —   | —   | —   |
| P4  | 80  | —   | —   | —   | —  | —  | —   | —   | —   | —   |
| P5  | 80  | —   | —   | —   | —  | —  | —   | —   | —   | —   |
| P6  | 80  | —   | —   | —   | —  | —  | —   | —   | —   | —   |
| P7  | —   | 80  | —   | —   | —  | —  | —   | —   | —   | —   |
| P8  | —   | —   | 80  | —   | —  | —  | —   | —   | —   | —   |
| P9  | 100 | —   | —   | —   | —  | —  | —   | —   | —   | —   |
| P10 | —   | —   | —   | 90  | —  | —  | —   | —   | —   | —   |
| P11 | —   | —   | —   | 80  | —  | —  | —   | —   | —   | —   |
| P12 | —   | —   | —   | 80  | —  | —  | —   | —   | —   | —   |
| P13 | —   | —   | —   | 80  | —  | —  | —   | —   | —   | —   |
| P14 | —   | —   | —   | —   | 80 | —  | —   | —   | —   | —   |
| P15 | —   | —   | —   | —   | —  | 80 | —   | —   | —   | —   |
| P16 | —   | —   | —   | 100 | —  | —  | —   | —   | —   | —   |
| P17 | —   | —   | —   | 80  | —  | —  | —   | —   | —   | —   |
| P18 | —   | —   | —   | —   | —  | —  | 90  | —   | —   | —   |
| P19 | —   | —   | —   | —   | —  | —  | 80  | —   | —   | —   |
| P20 | —   | —   | —   | —   | —  | —  | 80  | —   | —   | —   |
| P21 | —   | —   | —   | —   | —  | —  | 80  | —   | —   | —   |
| P22 | —   | —   | —   | —   | —  | —  | —   | 80  | —   | —   |
| P23 | —   | —   | —   | —   | —  | —  | —   | —   | 80  | —   |
| P24 | —   | —   | —   | —   | —  | —  | 100 | —   | —   | —   |
| P25 | —   | —   | —   | —   | —  | —  | 80  | —   | —   | —   |
| P26 | —   | —   | —   | —   | —  | —  | —   | —   | —   | 90  |
| P27 | —   | —   | —   | —   | —  | —  | —   | —   | —   | 80  |
| P28 | —   | —   | —   | —   | —  | —  | —   | —   | —   | 80  |
| P29 | —   | —   | —   | —   | —  | —  | —   | —   | —   | 80  |
| P30 | —   | —   | —   | —   | —  | —  | —   | —   | —   | —   |
| P31 | —   | —   | —   | —   | —  | —  | —   | —   | —   | —   |
| P32 | —   | —   | —   | —   | —  | —  | —   | —   | —   | 100 |
| P33 | —   | —   | —   | —   | —  | —  | —   | —   | —   | 80  |

| | (I) Noncrosslinked (meth)acrylate polymer | | (a) | | | (n) Polymerization initiator | (p) Filling material |
|---|---|---|---|---|---|---|---|
| | Copolymer 80L | Copolymer 80H | Ion sustained-release glass filler | | | | PMMA-C |
| | | | F1 | F2 | F3 | BPO | |
| P1  | — | — | 10 | —  | —  | 0.5 | —  |
| P2  | — | — | 20 | —  | —  | 0.5 | —  |
| P3  | — | — | —  | 20 | —  | 0.5 | —  |
| P4  | — | — | —  | —  | 20 | 0.5 | —  |
| P5  | — | — | —  | —  | 20 | 0.5 | 10 |
| P6  | — | — | —  | —  | 20 | —   | —  |
| P7  | — | — | —  | —  | 20 | 0.5 | —  |
| P8  | — | — | —  | —  | 20 | 0.5 | —  |
| P9  | — | — | —  | —  | —  | 0.5 | —  |
| P10 | — | — | 10 | —  | —  | 0.5 | —  |
| P11 | — | — | 20 | —  | —  | 0.5 | —  |
| P12 | — | — | —  | 20 | —  | 0.5 | —  |
| P13 | — | — | —  | —  | 20 | 0.5 | —  |
| P14 | — | — | —  | —  | 20 | 0.5 | —  |
| P15 | — | — | —  | —  | 20 | 0.5 | —  |
| P16 | — | — | —  | —  | —  | 0.5 | —  |
| P17 | — | — | —  | —  | 20 | —   | —  |
| P18 | — | — | 10 | —  | —  | 0.5 | —  |
| P19 | — | — | 20 | —  | —  | 0.5 | —  |
| P20 | — | — | —  | 20 | —  | 0.5 | —  |

TABLE 13-continued

| | | Powder material composition | | | | | |
|---|---|---|---|---|---|---|---|
| P21 | — | — | — | — | 20 | 0.5 | — |
| P22 | — | — | — | — | 20 | 0.5 | — |
| P23 | — | — | — | — | 20 | 0.5 | — |
| P24 | — | — | — | — | — | 0.5 | — |
| P25 | — | — | — | — | 20 | — | — |
| P26 | — | — | 10 | — | — | 0.5 | — |
| P27 | — | — | 20 | — | — | 0.5 | — |
| P28 | — | — | — | 20 | — | 0.5 | — |
| P29 | — | — | — | — | 20 | 0.6 | — |
| P30 | 80 | — | — | — | 20 | 0.5 | — |
| P31 | — | 80 | — | — | 20 | 0.5 | — |
| P32 | — | — | — | — | — | 0.5 | — |
| P33 | — | — | — | — | 20 | — | — |

TABLE 14

| | Liquid material composition | | | | | |
|---|---|---|---|---|---|---|
| | monofunctional (meth)acrylate polymerizable monomer | | Polymerization initiator | Multifunctional (meth)acrylate polymerizable monomer | | Organic solvent |
| | MMA | MMES | DMPT | 1G | HX | EtOH |
| L1 | 90 | — | — | 10 | — | — |
| L2 | 99.5 | — | — | 0.5 | — | — |
| L3 | — | 50 | 1 | — | 50 | — |
| L4 | — | 50 | — | — | 50 | — |
| L5 | 90 | — | 1 | 5 | 5 | — |
| L6 | 90 | — | 1 | 7 | — | 3 |
| L7 | 90 | — | — | 5 | 5 | — |
| L8 | 100 | — | 1 | — | — | — |
| L9 | 95 | — | 1 | 5 | — | — |
| L10 | 95 | — | — | 5 | — | — |

(Examples in Denture Base Resin)

TABLE 15

| | | | Test result | | | | | |
|---|---|---|---|---|---|---|---|---|
| | Powder material | Liquid material | Machinability | Surface hardness | Fluorine release amount (ppm) | Foul breath reduction rate | Acid neutralizing capacity | |
| | | | | | | | 6 hours | 24 hours |
| Example 32 | P1 | L1 | ○ | 21 | 0.4 | 29 | 4.5 | 5.2 |
| Example 33 | P2 | L1 | ⊚ | 23 | 0.8 | 34 | 5.1 | 5.6 |
| Example 34 | P3 | L1 | ⊚ | 24 | 1 | 36 | 5.1 | 5.6 |
| Example 35 | P4 | L1 | ⊚ | 24 | 1 | 36 | 4.9 | 5.2 |
| Example 36 | P5 | L1 | ⊚ | 22 | 0.9 | 40 | 5.0 | 5.3 |
| Example 37 | P4 | L2 | ⊚ | 24 | 1.1 | 35 | 5.0 | 5.4 |
| Example 38 | P6 | L1 | ⊚ | 23 | 2 | 35 | 5.3 | 5.8 |
| Example 39 | P7 | L1 | ○ | 21 | 0.4 | 31 | 4.7 | 5.0 |
| Example 40 | P8 | L1 | ⊚ | 23 | 0.2 | 33 | 4.6 | 5.2 |
| Comparative Example 21 | P9 | L1 | X | 19 | 0 | 7 | 4.2 | 4.3 |

TABLE 16

| | ICP measurement result | | | | |
|---|---|---|---|---|---|
| | B | Al | Si | Sr | Na |
| Example 32 | 0.3 | 0.1 | 0.5 | 1.4 | 0.3 |
| Example 33 | 0.5 | 0.1 | 0.9 | 2.8 | 0.5 |
| Example 34 | 0.5 | 0.2 | 1.2 | 3.1 | 0.7 |
| Example 35 | 0.8 | 0.3 | 1 | 3 | 0.8 |
| Example 36 | 0.7 | 0.3 | 0.8 | 2.9 | 0.8 |
| Example 37 | 0.8 | 0.3 | 1 | 3 | 0.8 |
| Example 38 | 1.1 | 0.3 | 1.3 | 3.3 | 1.1 |

TABLE 16-continued

| | ICP measurement result | | | | |
|---|---|---|---|---|---|
| | B | Al | Si | Sr | Na |
| Example 39 | 0.3 | 0.2 | 0.5 | 1.6 | 0.3 |
| Example 40 | 0.1 | 0.1 | 0.3 | 0.8 | 0.2 |
| Comparative Example 21 | 0 | 0 | 0 | 0 | 0 |

Examples 32 to 40 are each the two-component mixture ion sustained-release denture base-related material composition including the noncrosslinked (meth)acrylate polymer, the ion sustained-release glass, the monofunctional (meth) acrylate polymerizable monomer, the polymerization initiator, the multifunctional (meth)acrylate polymerizable monomer, and the filling material. This two-component mixture ion sustained-release denture base-related material composition has favorable machinability and improved surface hardness, as shown in Table 15. Moreover, the inclusion of the ion sustained-release glass has the effect of sustained-releasing 6 types of ions including the fluoride ion, as shown in Table 16. This is expected to suppress decalcification of an abutment tooth which tends to become unclean when a partial denture is used. The acid neutralizing capacity evaluation shows that the two-component mixture ion sustained-release denture base-related material composition neutralized the lactic acid water solution of pH 4.0 to about pH 5 after 6 hours and to about pH 5.5 after 24 hours, indicating high acid neutralization capacity. The foul breath suppression evaluation shows a reduction in VSC value by 30 or more, indicating that the two-component mixture ion sustained-release denture base-related material composition is effective in foul breath suppression.

Example 38 is the two-component mixture ion sustained-release denture base-related material composition not including the polymerization initiator. Since the polymerization initiator at the manufacturing stage remains in the noncrosslinked (meth)acrylate polymer, however, the two-component mixture ion sustained-release denture base-related material composition has favorable machinability and improved surface hardness even though the polymerization initiator is not included.

Example 39 is the ion sustained-release denture base-related material composition in which the noncrosslinked (meth)acrylate polymer is low in weight-average molecular weight. As shown in Table 15, this ion sustained-release denture base-related material composition has slightly lower machinability than the ion sustained-release denture base-related material composition in which the weight-average molecular weight of the noncrosslinked (meth)acrylate polymer is in the range of 500000 to 1500000, but still has favorable machinability and improved surface hardness. Moreover, the inclusion of the ion sustained-release glass has the effect of sustained-releasing 6 types of ions including the fluoride ion, as shown in Table 16. This is expected to suppress decalcification of an abutment tooth which tends to become unclean when a partial denture is used.

Example 40 is the ion sustained-release denture base-related material composition in which the noncrosslinked (meth)acrylate polymer is high in weight-average molecular weight. As shown in Table 15, this ion sustained-release denture base-related material composition has slightly lower ion sustained releasability including the fluorine than the ion sustained-release denture base-related material composition in which the weight-average molecular weight of the noncrosslinked (meth)acrylate polymer is in the range of 500000 to 1500000, but has high machinability.

Comparative Example 21 is the two-component mixture ion sustained-release denture base-related material composition not including the ion sustained-release glass. As shown in Table 15, this two-component mixture ion sustained-release denture base-related material composition has poor machinability and has no ion sustained-releasability including fluorine, as compared with the examples. Besides, the acid neutralizing capacity evaluation indicates that the two-component mixture ion sustained-release denture base-related material composition has little acid neutralizing capacity. The foul breath suppression evaluation shows little change in VSC value, indicating that the two-component mixture ion sustained-release denture base-related material composition does not have the sufficient foul breath reduction effect.

(Examples in Lining Material)

TABLE 17

| | Powder material | Liquid material | Machinability | Surface hardness | Fluorine release amount (ppm) | Foul breath reduction rate | Acid neutralizing capacity 6 hours | 24 hours |
|---|---|---|---|---|---|---|---|---|
| Example 41 | P10 | L3 | ○ | 13 | 0.6 | 31 | 4.7 | 5.1 |
| Example 42 | P11 | L3 | ⊚ | 15 | 1 | 40 | 4.9 | 5.2 |
| Example 43 | P12 | L3 | ⊚ | 17 | 1.2 | 39 | 5.0 | 5.5 |
| Example 44 | P13 | L3 | ⊚ | 16 | 1.3 | 38 | 5.0 | 5.5 |
| Example 45 | P14 | L3 | ○ | 15 | 0.3 | 32 | 4.6 | 5.1 |
| Example 46 | P15 | L3 | ⊚ | 14 | 0.3 | 33 | 4.6 | 5.0 |
| Comparative Example 22 | P16 | L3 | X | 10 | 0 | 10 | 4.3 | 4.5 |
| Comparative Example 23 | P17 | L4 | X | (—) Not measurable | 1.2 | 30 | 4.9 | 5.1 |

TABLE 18

| | ICP measurement result | | | | |
|---|---|---|---|---|---|
| | B | Al | Si | Sr | Na |
| Example 41 | 0.4 | 0.1 | 0.6 | 1.5 | 0.5 |
| Example 42 | 0.9 | 0.3 | 0.9 | 2.8 | 0.9 |
| Example 43 | 1.3 | 0.4 | 1.2 | 3.4 | 1.1 |
| Example 44 | 1 | 0.4 | 1 | 3.3 | 1.2 |
| Example 45 | 1.1 | 0.6 | 1.1 | 3.3 | 1.4 |
| Example 46 | 0.4 | 0.2 | 0.4 | 1.4 | 0.4 |
| Comparative Example 22 | 0 | 0 | 0 | 0 | 0 |
| Comparative Example 23 | 1.4 | 0.6 | 1.2 | 3.3 | 1.3 |

Examples 41 to 46 are each the two-component mixture ion sustained-release denture base-related material composition including the noncrosslinked (meth)acrylate polymer, the ion sustained-release glass, the monofunctional (meth)acrylate polymerizable monomer, the polymerization initiator, and the multifunctional (meth)acrylate polymerizable monomer. This two-component mixture ion sustained-release denture base-related material composition has favorable machinability and improved surface hardness, as shown in Table 17. Moreover, the inclusion of the ion sustained-release glass has the effect of sustained-releasing 6 types of ions including the fluoride ion, as shown in Table 18. This is expected to suppress the adhesion of plaque to remaining teeth and suppress the growth of bacteria and fungi. The acid neutralizing capacity evaluation shows that the two-component mixture ion sustained-release denture base-related material composition neutralized the lactic acid water solution of pH 4.0 to pH 4.5 or more after 6 hours and to pH 5.0 or more after 24 hours, indicating high acid neutralization capacity. The foul breath suppression evaluation shows a reduction in VSC value by 30 or more, indicating that the two-component mixture ion sustained-release denture base-related material composition is effective in foul breath suppression.

Example 45 is the ion sustained-release denture base-related material composition in which the noncrosslinked (meth)acrylate polymer is low in weight-average molecular weight. As shown in Table 17, this ion sustained-release denture base-related material composition has slightly lower machinability than the ion sustained-release denture base-related material composition in which the weight-average molecular weight of the noncrosslinked (meth)acrylate polymer is in the range of 500000 to 1500000, but still has favorable machinability and improved surface hardness. Moreover, the inclusion of the ion sustained-release glass has the effect of sustained-releasing 6 types of ions including the fluoride ion, as shown in Table 18. This is expected to suppress decalcification of an abutment tooth which tends to become unclean when a partial denture is used.

Example 46 is the ion sustained-release denture base-related material composition in which the noncrosslinked (meth)acrylate polymer is high in weight-average molecular weight. As shown in Table 17, this ion sustained-release denture base-related material composition has slightly lower ion sustained releasability including the fluorine than the ion sustained-release denture base-related material composition in which the weight-average molecular weight of the noncrosslinked (meth)acrylate polymer is in the range of 500000 to 1500000, but has high machinability.

Comparative Example 22 is the two-component mixture ion sustained-release denture base-related material composition not including the ion sustained-release glass. As shown in Table 17, this two-component mixture ion sustained-release denture base-related material composition has poor machinability and has no ion sustained-releasability including fluorine. Besides, the acid neutralizing capacity evaluation indicates that the two-component mixture ion sustained-release denture base-related material composition has little acid neutralizing capacity. The foul breath suppression evaluation shows little change in VSC value, indicating that the two-component mixture ion sustained-release denture base-related material composition does not have the sufficient foul breath reduction effect, Comparative Example 23 is the two-component mixture ion sustained-release denture base-related material composition not including the polymerization initiator. As shown in Table 17, this two-component mixture ion sustained-release denture base-related material composition has poor machinability, and also its surface hardness was unable to be measured because of insufficient hardening.

(Examples in Quick Cure Resin)

TABLE 20

ICP measurement result

|  | B | Al | Si | Sr | Na |
|---|---|---|---|---|---|
| Example 47 | 0.2 | 0.1 | 0.3 | 1.5 | 0.3 |
| Example 48 | 0.4 | 0.2 | 0.7 | 2.9 | 0.6 |
| Example 49 | 0.5 | 0.3 | 0.9 | 3.2 | 0.7 |
| Example 50 | 0.8 | 0.2 | 0.8 | 3.4 | 0.8 |
| Example 51 | 0.2 | 0.2 | 0.4 | 1.6 | 0.4 |
| Example 52 | 0.3 | 0.2 | 0.5 | 2.7 | 0.5 |
| Example 53 | 0.4 | 0.2 | 0.8 | 3 | 0.5 |
| Example 54 | 0.7 | 0.3 | 0.9 | 3.1 | 0.6 |
| Example 55 | 0.2 | 0.2 | 0.3 | 1.5 | 0.3 |
| Example 56 | 0.1 | 0.2 | 0 | 1.5 | 0.3 |
| Comparative Example 24 | 0 | 0 | 0 | 0 | 0 |
| Comparative Example 25 | 1.2 | 0.4 | 0.9 | 3.5 | 1.3 |

Examples 47 to 56 are each the two-component mixture ion sustained-release denture base-related material composition including the noncrosslinked (meth)acrylate polymer, the ion sustained-release glass, the monofunctional (meth)acrylate polymerizable monomer, the polymerization initiator, the multifunctional (meth)acrylate polymerizable monomer, and the organic solvent. This two-component mixture ion sustained-release denture base-related material composition has favorable machinability and improved surface hardness, as shown in Table 19. Moreover, the inclusion of the ion sustained-release glass has the effect of sustained-releasing 6 types of ions including the fluoride ion, as shown in Table 20. This is expected to suppress the adhesion of plaque to remaining teeth and suppress the growth of bacteria and fungi. The acid neutralizing capacity evaluation shows that the two-component mixture ion sustained-release denture base-related material composition neutralized the lactic acid water solution of pH 4.0 to about pH 5 after 6 hours and to about pH 5.5 after 24 hours, indicating high acid neutralization capacity. The foul breath suppression evaluation shows a reduction in VSC value by 30 or more, indicating that the two-component mixture ion sustained-release denture base-related material composition is effective in foul breath suppression.

TABLE 19

Test result

|  | Powder material | Liquid material | Machinability | Surface hardness | Fluorine release amount (ppm) | Foul breath reduction rate | Acid neutralizing capacity 6 hours | 24 hours |
|---|---|---|---|---|---|---|---|---|
| Example 47 | P18 | L5 | ○ | 14 | 0.6 | 31 | 4.7 | 5.2 |
| Example 48 | P19 | L5 | ◉ | 16 | 1 | 41 | 5.0 | 5.2 |
| Example 49 | P20 | L5 | ◉ | 17 | 1.3 | 39 | 5.0 | 5.4 |
| Example 50 | P21 | L5 | ◉ | 18 | 1.3 | 42 | 5.1 | 5.5 |
| Example 51 | P18 | L6 | ○ | 14 | 0.7 | 37 | 4.7 | 5.3 |
| Example 52 | P19 | L6 | ◉ | 15 | 0.9 | 45 | 5.0 | 5.4 |
| Example 53 | P20 | L6 | ◉ | 17 | 1.2 | 46 | 5.1 | 5.5 |
| Example 54 | P21 | L6 | ◉ | 17 | 1.3 | 46 | 5.2 | 5.6 |
| Example 55 | P22 | L5 | ○ | 12 | 0.5 | 31 | 4.9 | 5.1 |
| Example 56 | P23 | L5 | ◉ | 15 | 0.4 | 36 | 4.7 | 5.0 |
| Comparative Example 24 | P24 | L5 | X | 13 | 0 | 9 | 4.3 | 4.4 |
| Comparative Example 25 | P25 | L7 | X | (—) Not measurable | 1.5 | 31 | 4.8 | 5.2 |

Example 55 is the ion sustained-release denture base-related material composition in which the noncrosslinked (meth)acrylate polymer is low in weight-average molecular ability, and also its surface hardness was unable to be measured because of insufficient hardening.

(Examples in Base Orthodontic Resin)

TABLE 21

| | Powder material | Liquid material | Machinability | Surface hardness | Fluorine release amount (ppm) | Foul breath reduction rate | Acid neutralizing capacity 6 hours | Acid neutralizing capacity 24 hours |
|---|---|---|---|---|---|---|---|---|
| Example 57 | P26 | L8 | ○ | 11 | 0.5 | 34 | 4.6 | 5.1 |
| Example 58 | P27 | L8 | ⊚ | 13 | 0.9 | 34 | 5.0 | 5.2 |
| Example 59 | P28 | L8 | ⊚ | 13 | 1.2 | 39 | 5.0 | 5.4 |
| Example 60 | P29 | L8 | ⊚ | 13 | 1.4 | 48 | 5.1 | 5.4 |
| Example 61 | P26 | L9 | ○ | 12 | 0.4 | 36 | 4.7 | 5.0 |
| Example 62 | P27 | L9 | ⊚ | 13 | 0.8 | 45 | 4.8 | 5.2 |
| Example 63 | P28 | L9 | ⊚ | 14 | 1 | 45 | 5.0 | 5.4 |
| Example 64 | P29 | L9 | ⊚ | 15 | 1.1 | 47 | 5.0 | 5.4 |
| Example 65 | P30 | L8 | ○ | 10 | 0.4 | 40 | 4.6 | 5.1 |
| Example 66 | P31 | L8 | ⊚ | 1.6 | 0.2 | 39 | 4.5 | 5.1 |
| Comparative Example 26 | P32 | L9 | X | 10 | 0 | 7 | 4.3 | 4.5 |
| Comparative Example 27 | P33 | L10 | X | (—) Not measurable | 1.7 | 34 | 4.9 | 5.3 | weight. As shown in Table 19, this ion sustained-release denture base-related material composition has slightly lower machinability than the ion sustained-release denture base-related material composition in which the weight-average molecular weight of the noncrosslinked (meth)acrylate polymer is in the range of 500000 to 1500000, but still has favorable machinability and improved surface hardness. Moreover, the inclusion of the ion sustained-release glass has the effect of sustained-releasing 6 types of ions including the fluoride ion, as shown in Table 20. This is expected to suppress decalcification of an abutment tooth which tends to become unclean when a partial denture is used.

Example 56 is the ion sustained-release denture base-related material composition in which the noncrosslinked (meth)acrylate polymer is high in weight-average molecular weight. As shown in Table 19, this ion sustained-release denture base-related material composition has slightly lower ion sustained releasability including the fluorine than the ion sustained-release denture base-related material composition in which the weight-average molecular weight of the non-crosslinked (meth)acrylate polymer is in the range of 500000 to 1500000, but has high machinability.

Comparative Example 24 is the two-component mixture ion sustained-release denture base-related material composition not including the ion sustained-release glass. As shown in Table 19, this two-component mixture ion sustained-release denture base-related material composition has poor machinability and has no ion sustained-releasability including fluorine. Besides, the acid neutralizing capacity evaluation indicates that the two-component mixture ion sustained-release denture base-related material composition has little acid neutralizing capacity. The foul breath suppression evaluation shows little change in VSC value, indicating that the two-component mixture ion sustained-release denture base-related material composition does not have the sufficient foul breath reduction effect.

Comparative Example 25 is the two-component mixture ion sustained-release denture base-related material composition not including the polymerization initiator. As shown in Table 19, this two-component mixture ion sustained-release denture base-related material composition has poor machin-

TABLE 22

| ICP measurement result | B | Al | Si | Sr | Na |
|---|---|---|---|---|---|
| Example 57 | 0.5 | 0.1 | 0.6 | 2.1 | 0.5 |
| Example 58 | 1 | 0.2 | 1.4 | 3.8 | 1 |
| Example 59 | 1.2 | 0.3 | 1.7 | 4 | 1.3 |
| Example 60 | 1.4 | 0.4 | 1.6 | 4.2 | 1.2 |
| Example 61 | 0.4 | 0.2 | 0.5 | 2 | 0.3 |
| Example 62 | 0.9 | 0.2 | 1.2 | 3.3 | 0.8 |
| Example 63 | 1.1 | 0.3 | 1.4 | 3.4 | 1 |
| Example 64 | 1.2 | 0.3 | 1.4 | 3.5 | 1 |
| Example 65 | 0.6 | 0.2 | 0.6 | 2 | 0.4 |
| Example 66 | 0.3 | 0.1 | 0.4 | 1.1 | 0.1 |
| Comparative Example 26 | 0 | 0 | 0 | 0 | 0 |
| Comparative Example 27 | 1.3 | 0.4 | 2.1 | 6.1 | 1.6 |

Examples 57 to 66 are each the two-component mixture ion sustained-release denture base-related material composition including the noncrosslinked (meth)acrylate polymer, the ion sustained-release glass, the monofunctional (meth)acrylate polymerizable monomer, the polymerization initiator, and the multifunctional (meth)acrylate polymerizable monomer. This two-component mixture ion sustained-release denture base-related material composition has favorable machinability and improved surface hardness, as shown in Table 21. Moreover, the inclusion of the ion sustained-release glass has the effect of sustained-releasing 6 types of ions including the fluoride ion, as shown in Table 22. This is expected to suppress the adhesion of plaque to remaining teeth and suppress the growth of bacteria and fungi. The acid neutralizing capacity evaluation shows that the two-component mixture ion sustained-release denture base-related material composition neutralized the lactic acid water solution of pH 4.0 to pH 4.5 or more after 6 hours and to pH 5.0 or more after 24 hours, indicating high acid neutralization capacity. The foul breath suppression evaluation shows a reduction in VSC value by 30 or more, indicating that the two-component mixture ion sustained-release denture base-related material composition is effective in foul breath suppression.

Example 65 is the ion sustained-release denture base-related material composition in which the noncrosslinked (meth)acrylate polymer is low in weight-average molecular weight. As shown in Table 21, this ion sustained-release denture base-related material composition has slightly lower machinability than the ion sustained-release denture base-related material composition in which the weight-average molecular weight of the noncrosslinked (meth)acrylate polymer is in the range of 500000 to 1500000, but still has favorable machinability and improved surface hardness. Moreover, the inclusion of the ion sustained-release glass has the effect of sustained-releasing 6 types of ions including the fluoride ion, as shown in Table 22. This is expected to suppress decalcification of an abutment tooth which tends to become unclean when a partial denture is used.

Example 66 is the ion sustained-release denture base-related material composition in which the noncrosslinked (meth)acrylate polymer is high in weight-average molecular weight. As shown in Table 21, this ion sustained-release denture base-related material composition has slightly lower ion sustained releasability including the fluorine than the ion sustained-release denture base-related material composition in which the weight-average molecular weight of the non-crosslinked (meth)acrylate polymer is in the range of 500000 to 1500000, but has high machinability.

Comparative Example 26 is the two-component mixture ion sustained-release denture base-related material composition not including the ion sustained-release glass. As shown in Table 22, this two-component mixture ion sustained-release denture base-related material composition has poor machinability and has no ion sustained-releasability including fluorine. Besides, the acid neutralizing capacity evaluation indicates that the two-component mixture ion sustained-release denture base-related material composition has little acid neutralizing capacity. The foul breath suppression evaluation shows little change in VSC value, indicating that the two-component mixture ion sustained-release denture base-related material composition does not have the sufficient foul breath reduction effect.

Comparative Example 27 is the two-component mixture ion sustained-release denture base-related material composition not including the polymerization initiator. As shown in Table 22, this two-component mixture ion sustained-release denture base-related material composition has poor machinability, and also its surface hardness was unable to be measured because of insufficient hardening.

(8) Two-Component Mixture Ion Sustained-Release Mucosa Modifier Composition

Examples and comparative examples of the two-component mixture ion sustained-release mucosa modifier composition are described below.

The following test methods are used to evaluate the performance of the two-component mixture ion sustained-release mucosa modifier composition prepared in each of the examples and the comparative examples.

[Machinability of Two-Component Mixture Ion Sustained-Release Mucosa Modifier Composition]

Purpose: To evaluate the machinability of the two-component mixture ion sustained-release mucosa modifier composition.

Method: The powder material and the liquid material of the two-component mixture ion sustained-release mucosa modifier composition according to the present invention were mixed and swollen at the ratio of 1.2 g (powder material) to 1 mL (liquid material), and then packed into a stainless steel mold (20φ×2 mm: discoid). This was then pressed by a glass plate via a nylon film and left for 30 minutes, to form a sample. The sample was cut by a technical carbide bur, and the machinability was evaluated in the following four levels.

A: Machinability is very good and the cutting surface has no unevenness.

B: Machinability is good, but the cutting surface has slight unevenness.

C: Cutting is difficult as the mucosa modifier sticks to the grinder. Besides, the cutting surface has unevenness to some extent.

D: Cutting is difficult as the mucosa modifier sticks to the grinder. Besides, the cutting surface has unevenness.

[Measurement and Evaluation of Fluorine Release Amount from Two-Component Mixture Ion Sustained-Release Mucosa Modifier Composition]

Purpose: To evaluate the fluorine release property from the two-component mixture ion sustained-release mucosa modifier composition.

Method: The powder material and the liquid material of the two-component mixture ion sustained-release mucosa modifier composition according to the present invention were mixed and swollen at the ratio of 1.2 g (powder material) to 1 mL (liquid material), and then packed into a stainless steel mold (15φ×1 mm: discoid). This was then pressed by a glass plate via a nylon film and left for 30 minutes, to form a sample. The sample was put in a plastic container including 5 mL of distilled water, and sealed and left in a 37° C. incubator for 1 week. The container was taken out of the incubator after 1 week, and the amount of fluorine eluted from the discoid sample was measured using a fluoride ion composite electrode (Model 9609, Orion Research Inc.) and an ion meter (Model 720A, Orion Research Inc.). Upon measurement, 0.5 ml of TISABIII (Orion Research Inc.) was added as an ionic strength adjuster. Calibration was performed using standard solutions of 0.02 ppm, 0.1 ppm, 1 ppm, 10 ppm, and 50 ppm. The fluorine release amount is preferably greater than or equal to 0.2 ppm, and more preferably greater than or equal to 0.5 ppm.

[Measurement and Evaluation of Ion Release Amount from Two-Component Mixture Ion Sustained-Release Mucosa Modifier Composition]

Purpose: To evaluate the ion release property from the two-component mixture ion sustained-release mucosa modifier composition.

Method: The powder material and the liquid material of the two-component mixture ion sustained-release mucosa modifier composition according to the present invention were mixed and swollen at the ratio of 1.2 g (powder material) to 1 mL (liquid material), and then packed into a stainless steel mold (15φ×1 mm: discoid). This was then pressed by a glass plate via a nylon film and left for 30 minutes, to form a sample. The sample was put in a plastic container including 5 mL of distilled water, and sealed and left in a 37° C. incubator for 1 week. The container was taken out of the incubator after 1 week, and the amount of ion eluted from the discoid sample was measured using an ICP emission spectrometer. Each metal ion amount was converted using calibration obtained from standard samples (1 ppm, 2.5 ppm, 5 ppm, 10 ppm) of the ion.

[Evaluation of Acid Neutralizing Capacity of Two-Component Mixture Ion Sustained-Release Mucosa Modifier Composition]

Purpose: To evaluate the acid neutralizing capacity of the two-component mixture ion sustained-release mucosa modifier composition.

Method: The powder material and the liquid material of the two-component mixture ion sustained-release mucosa modifier composition according to the present invention were mixed and swollen at the ratio of 1.2 g (powder material) to 1 mL (liquid material), and then packed into a stainless steel mold (15φ×1 mm: discoid). This was then pressed by a glass plate via a nylon film and left for 30 minutes, to form a sample. The sample was immersed in 5 mL of a lactic acid water solution (pH adjusted to 4.0). The pH of the lactic acid water solution after 6 hours and after 24 hours was measured using a pH meter (D-51, HORIBA, Ltd.).

[Evaluation of Foul Breath Suppression Effect of Two-Component Mixture Ion Sustained-Release Mucosa Modifier Composition]

Purpose: To evaluate the foul breath suppression effect of the two-component mixture ion sustained-release mucosa modifier composition.

Method: The powder material and the liquid material of the two-component mixture ion sustained-release mucosa modifier composition according to the present invention were mixed and swollen at the ratio of 1.2 g (powder material) to 1 mL (liquid material), and then packed into a stainless steel mold (15φ×0.5 mm: discoid). This was then pressed by a glass plate via a nylon film and left for 30 minutes, to form a sample. The sample was fixed to the palatine portion, and kept for 5 hours without drinking and eating. The breath before attaching the sample and the breath after attaching the sample for 5 hours were compared for evaluation. In the breath comparison, the sulfur compound concentration (VSC value) in the oral cavity resulting from hydrogen sulfide, methylmercaptan, dimethyl sulfide, etc. in the breath was measured (XP-Breath-Tron, New Cosmos Electric Co., Ltd.), and the value of VSC(1) in the breath before attaching the sample and the value of VSC(2) in the breath after attaching the sample for 5 hours were compared. The foul breath reduction rate=(1−VSC(2)/VSC(1))×100 was calculated based on the evaluation result, from which the average value of the 5 persons is calculated.

The following shows the names and abbreviations of the components used in the examples of the two-component mixture ion sustained-release mucosa modifier composition according to the present invention and the comparative examples.

PEMA50: polyethyl methacrylate (average particle diameter (D50): 50 μm, weight-average molecular weight: 300000, shape: spherical)
F1: ion sustained-release glass 1
F2: ion sustained-release glass 2
F3: ion sustained-release glass 3
BB: benzyl benzoate
DBS: dibutyl sebacate
DBP: dibutyl phthalate
EtOH: ethanol
PMMA-C: crosslinked polymethyl methacrylate (polymethyl methacrylate made up of 95 parts MMA and 5 parts 1 G, average particle diameter (D50): 10 μm, shape: spherical)

The powder material and the liquid material were prepared according to the composition shown in Tables 23 and 24.

TABLE 23

| | Powder material composition | | | | |
|---|---|---|---|---|---|
| | Noncross linked (meth)acrylate polymer | Ion sustained-release glass | | | Filling material |
| | PEMA50 | F1 | F2 | F3 | PMMA-C |
| P1 | 90 | 10 | — | — | — |
| P2 | 80 | 20 | — | — | — |
| P3 | 80 | — | 20 | — | — |
| P4 | 80 | — | — | 20 | — |
| P5 | 80 | — | — | 10 | 10 |
| P6 | 100 | — | — | — | — |

TABLE 24

| | Liquid material composition | | | |
|---|---|---|---|---|
| | Plasticizer | | | Organic solvent |
| | BB | DBS | DBP | EtOH |
| L1 | 20 | 70 | — | 10 |
| L2 | — | — | 90 | 10 |
| L3 | 30 | 70 | — | — |

TABLE 25

| | | | | Test result | | | | |
|---|---|---|---|---|---|---|---|---|
| | | | | | | Acid neutralizing capacity | | Foul breath reduction |
| | | | | Fluorine release | | | | |
| | Powder material | Liquid material | Machinability | amount (ppm) | 6 hours | 24 hours | rate (%) | Remarks |
| Example 67 | P1 | L1 | ○ | 1.2 | 4.5 | 5.5 | 34 | |
| Example 68 | P2 | L1 | ⊚ | 1.5 | 4.9 | 5.7 | 44 | |
| Example 69 | P3 | L1 | ⊚ | 2.1 | 5 | 6 | 50 | |
| Example 70 | P4 | L1 | ⊚ | 2 | 5.1 | 6.1 | 51 | |
| Example 71 | P5 | L1 | ○ | 1.9 | 5 | 6 | 48 | |
| Example 72 | P4 | L2 | ⊚ | 2.2 | 5 | 6.1 | 56 | |
| Comparative Example 28 | P6 | L1 | X | 0 | 4.3 | 4.4 | 8 | |
| Comparative Example 29 | P4 | L3 | ※ | ※ | ※ | ※ | ※ | ※ Sample cannot be formed |

TABLE 26

ICP measurement result

| | B | Al | Si | Sr | Na | Remarks |
|---|---|---|---|---|---|---|
| Example 67 | 0.4 | 0.2 | 1 | 3.1 | 0.6 | |
| Example 68 | 0.6 | 0.3 | 2.1 | 5.4 | 1.1 | |
| Example 69 | 0.7 | 0.5 | 1.6 | 5.6 | 1.5 | |
| Example 70 | 1.2 | 0.5 | 1.8 | 5.9 | 1.5 | |
| Example 71 | 1.4 | 0.6 | 1.9 | 5.7 | 1.4 | |
| Example 72 | 1.1 | 0.7 | 2 | 5.8 | 1.6 | |
| Comparative Example 28 | 0 | 0 | 0 | 0 | 0 | |
| Comparative Example 29 | ※ | ※ | ※ | ※ | ※ | ※ Sample cannot be formed |

Examples 67 to 72 are each the two-component mixture ion sustained-release mucosa modifier composition including the noncrosslinked (meth)acrylate polymer, the ion sustained-release glass, the plasticizer, the organic solvent, and the filling material. This two-component mixture ion sustained-release denture base-related material composition has favorable machinability, as shown in Table 25. Moreover, the inclusion of the ion sustained-release glass has the effect of sustained-releasing 6 types of ions including the fluoride ion, as shown in Table 26. This is expected to suppress decalcification of an abutment tooth which tends to become unclean when a partial denture is used. The acid neutralizing capacity evaluation shows that the two-component mixture ion sustained-release mucosa modifier composition neutralized the lactic acid water solution of pH 4.0 to about pH 5 after 6 hours and to about pH 6 after 24 hours, indicating high acid neutralization capacity. The foul breath suppression evaluation shows a reduction in VSC value by 30 or more, indicating that the two-component mixture ion sustained-release mucosa modifier composition is effective in foul breath suppression.

Comparative Example 28 is the two-component mixture ion sustained-release mucosa modifier composition not including the ion sustained-release glass. As shown in Table 25, this two-component mixture ion sustained-release mucosa modifier composition has poor machinability and has no ion sustained-releasability including fluorine. Besides, the acid neutralizing capacity evaluation indicates that the two-component mixture ion sustained-release mucosa modifier composition has no acid neutralizing capacity. The foul breath suppression evaluation shows little change in VSC value, indicating that the two-component mixture ion sustained-release mucosa modifier composition does not have the sufficient foul breath reduction effect.

Comparative Example 29 is the two-component mixture ion sustained-release mucosa modifier composition not including the organic solvent. As shown in Table 25, the sample of this two-component mixture ion sustained-release mucosa modifier composition was unable to be formed.

(9) Dental Resin Temporary Sealing Material Composition

Examples and comparative examples of the dental resin temporary sealing material composition are described below.

The following test methods are used to evaluate the performance of the dental resin temporary sealing material composition prepared in each of the examples and the comparative examples.

[Measurement of Element Concentration Resulting from Ion Sustained-Released from Dental Resin Temporary Sealing Material Composition]

The powder and the liquid were mixed at the ratio shown in Table 4. A stainless-steel mold (15φ×1 mm, disk-shaped) was filled with the mixture, cover glass was placed on both surfaces to apply pressure with glass mixing plates, and the mixture was hardened. After the hardening, the hardened material was taken out of the mold, and put in a plastic container containing 5 ml of distilled water. After sealed, the container was left in a constant temperature box of 37° C. for one week. After one week, the container was taken out of the constant temperature box, and the eluate from which the discoid test piece was removed was collected. The element concentration measurement was performed on the eluate by the same method as the foregoing [Measurement of element content resulting from ion sustained-released from ion sustained-release glass or filler].

[Evaluation of Acid Neutralizing Capacity of Dental Resin Temporary Sealing Material Composition]

The powder and the liquid were mixed at the ratio shown in Table 29. A stainless-steel mold (15φ×1 mm, disk-shaped) was filled with the mixture, cover glass was placed on both surfaces to apply pressure with glass mixing plates, and the mixture was hardened. After the hardening, the hardened material was taken out of the mold, and immersed in 5 ml of a lactic acid water solution (with pH adjusted to 4.0). The pH of the lactic acid water solution after 6 hours and after 24 hours was measured using a pH meter (D-51, HORIBA, Ltd.).

[Removability]

Purpose: To evaluate the removability of the hardened material of the dental resin temporary sealing material composition.

Method: A cavity of 4.5 mm in diameter and 1.6 mm in depth was formed in a coronal portion of an extracted cow tooth, and washed with water and dried. The powder and the liquid were mixed at the ratio shown in Table 4, and the cavity was filled with the mixture. After the temporary sealing material hardened, it was left in water of 37° C. for 24 hours. Each of five dentists then conducted the operation of removing the hardened material (five samples) using a probe, and evaluated the removability on the following 4-point scale. The most frequent grade was set as the result of evaluation of the removability.

A: The material is easily removable as a block.

B: The material is easily removable with no residue on the tooth surface, though not removed as a block.

C: The material is torn during removal, and remains on the tooth surface.

D: The material is hard and is difficult to be removed.

[Sealability]

Purpose: To evaluate the sealability of the hardened material of the dental resin temporary sealing material composition.

Method: A cavity of 4.5 mm in diameter and 1.6 mm in depth was formed in a coronal portion of an extracted cow tooth, and washed with water and dried. The powder and the liquid were mixed at the ratio shown in Table 4, and the cavity was filled with the mixture. After the temporary sealing material hardened, it was left in water of 37° C. for 24 hours. A thermal cycle of immersion in water of 4° C. and 60° C. each for 1 minute was repeatedly performed 50 times. After the thermal cycle ends, the tooth was immersed in a 0.1% basic fuchsin water solution for 2 hours. The filled sample was then removed, and the pigment invasion state was observed. The evaluation was made on the following 4-point scale. Five samples were tested, and the most frequent grade is shown.
A: No pigment penetration.
B: Penetration up to inside enamel.
C: Penetration up to inside dentin.
D: Penetration throughout the cavity.
[Measurement of Shore D Hardness]

Purpose: To evaluate the hardness of the hardened material of the dental resin temporary sealing material composition.

Method: The powder and the liquid were mixed at the ratio shown in Table 29. A stainless-steel mold (15φ×1 mm, disk-shaped) was filled with the mixture, cover glass was placed on both surfaces to apply pressure with glass mixing plates, and the mixture was hardened. After the hardening, the hardened material was taken out of the mold, and put in a plastic container containing ion-exchange water. After sealed, the container was left in a constant temperature box of 37° C. for one week. After one week, the container was taken out of the constant temperature box, and the measurement was performed using a Shore D hardness tester. Five samples produced were each subject to the measurement three times, and the average of all measurements is shown. The measurement conforms to JIS K6253 (vulcanized rubber test method). The Shore D hardness is preferably in the range of 30 to 50. In the case where the Shore D hardness is less than 30, deformation due to biting pressure is likely to occur. In the case where the Shore D hardness exceeds 50, problems such as the difficulty of removal due to hardness arise.

[Evaluation of Foul Breath Suppression Effect of Dental Resin Temporary Sealing Material Composition]

Purpose: To evaluate the foul breath suppression effect of the dental resin temporary sealing material composition.

Method: To evaluate the foul breath suppression effect of each of the examples and the comparative examples, the following test was conducted on 5 persons. The powder material and the liquid material of the dental resin temporary sealing material composition according to the present invention were mixed and swollen at the ratio of 2:1, and then packed into a stainless steel mold (15φ×0.5 mm: discoid). Cover glass was placed on both surfaces to apply pressure with glass mixing plates, and the mixture was hardened. The hardened material was fixed to the palatine portion, and kept for 5 hours without drinking and eating. The breath before attaching the hardened material and the breath after attaching the hardened material for 5 hours were compared for evaluation. In the breath comparison, the sulfur compound concentration (VSC value) in the oral cavity resulting from hydrogen sulfide, methylmercaptan, dimethyl sulfide, etc. in the breath was measured (XP-Breath-Tron, New Cosmos Electric Co., Ltd.), and the value of VSC(1) in the breath before attaching the sample and the value of VSC(2) in the breath after attaching the sample for 5 hours were compared. The foul breath reduction rate=(1−VSC(2)/VSC(1))×100 was calculated based on the evaluation result, from which the average value of the 5 persons is calculated.

The following shows the names and abbreviations of the components used in the examples of the present invention and the comparative examples.

[Noncrosslinked (Meth)Acrylate Polymer]

PEMA1: polyethyl methacrylate (50% average particle diameter: 70 μm, weight-average molecular weight: 950000, shape: spherical)

PMMA1: polymethyl methacrylate (50% average particle diameter: 80 μm, weight-average molecular weight: 1000000, shape: spherical)

PEMA2: polyethyl methacrylate (50% average particle diameter: 4 μm, weight-average molecular weight: 40000, shape: spherical)

PMMA1: polymethyl methacrylate (50% average particle diameter: 160 μm, weight-average molecular weight: 1600000, shape: spherical)

[Filling Material]
Ion sustained-release glass 1
Ion sustained-release glass 2
Ion sustained-release glass 3
Filler 1: sodium fluoride powder (Nacalai Tesque, Inc.)

[Monofunctional (Meth)Acrylate Polymerizable Monomer]
MMA: methyl methacrylate

[Hydrophilic Polymerizable Monomer]
HEMA: 2-hydroxyethyl methacrylate
14EG: polyethylene glycol dimethacrylate (number of cycles: 14)

[Polymerization Initiator]
BPO: benzoyl peroxide
DMPT: N,N-dimethyl p-toluidine

[Plasticizer]
BB: benzyl benzoate

[Hydrophilic Polymerizable Monomer]
3G: triethyleneglycol dimethacrylate

TABLE 27

| Powder material No. | Noncrosslinked (meth)acrylate polymer | | | | Glass | | | | Polymerization initiator |
|---|---|---|---|---|---|---|---|---|---|
| | | | | | Ion sustained-release glass | | | Non-ion sustained release glass | |
| | PEMA1 | PEMA2 | PMMA1 | PMMA2 | 1 | 2 | 3 | (filler 1) | BPO |
| P1 | — | — | 93 | — | 6.5 | — | — | — | 0.5 |
| P2 | 70 | — | — | — | — | 29.5 | — | — | 0.5 |
| P3 | — | — | 98 | — | 1.5 | — | — | — | 0.5 |
| P4 | 63.5 | — | — | — | — | 36 | — | — | 0.5 |
| P5 | 85 | — | — | — | — | 14.5 | — | — | 0.5 |
| P6 | — | — | 85 | — | — | — | 14.5 | — | 0.5 |
| P7 | — | — | 85 | — | — | — | — | 14.5 | 0.5 |
| P8 | 85 | — | — | — | — | — | 10 | 4.5 | 0.5 |
| P9 | — | 80 | — | — | 19.5 | — | — | — | 0.5 |
| P10 | — | — | — | 80 | — | 19.5 | — | — | 0.5 |

TABLE 28

| | Liquid material composition (g) | | | | | |
|---|---|---|---|---|---|---|
| Liquid material No. | Monofunctional (meth)acrylate polymerizable monomer MMA | Plasticizer BB | Hydrophilic polymerizable monomer | | Non-hydrophilic polymerizable monomer 3G | Polymerization initiator DMPT |
| | | | 14EG | HEMA | | |
| L1 | 15 | 69 | 7 | 8 | — | 1 |
| L2 | 44 | 19 | 18 | 18 | — | 1 |
| L3 | 7 | 85 | — | 7 | — | 1 |
| L4 | 50 | 8 | 21 | 20 | — | 1 |
| L5 | 30 | 44 | 12.5 | 12.5 | — | 1 |
| L6 | 30 | 44 | — | — | 25 | 1 |

TABLE 29

| | | | Test result | | | | Acid neutralizing capacity | | Foul breath reduction |
|---|---|---|---|---|---|---|---|---|---|
| | Powder material | Liquid material | Powder/ liquid ratio | Removability | Sealability | Shore D hardness | After 6 hours | After 12 hours | rate (%) |
| Example 73 | P1 | L1 | 2/1 | ⊚ | ○ | 38.3 | 4.6 | 5.1 | 32 |
| Example 74 | P1 | L2 | 2/1 | ○ | ⊚ | 42.6 | 4.5 | 5.1 | 34 |
| Example 75 | P2 | L1 | 2/1 | ○ | ○ | 46.1 | 5 | 5.6 | 50 |
| Example 76 | P2 | L2 | 2/1 | ○ | ⊚ | 44.8 | 5 | 5.7 | 52 |
| Example 77 | P5 | L5 | 2.2/1 | ⊚ | ⊚ | 45.4 | 4.8 | 5.2 | 45 |
| Example 78 | P5 | L5 | 1.8/1 | ⊚ | ⊚ | 44 | 4.9 | 5.7 | 42 |
| Example 79 | P5 | L5 | 2/1 | ⊚ | ⊚ | 44.5 | 5.1 | 5.8 | 43 |
| Example 80 | P6 | L5 | 2/1 | ⊚ | ⊚ | 44.8 | 4.9 | 5.9 | 44 |
| Example 81 | P8 | L5 | 2/1 | ⊚ | ⊚ | 45.5 | 4.7 | 5.1 | 37 |
| Comparative Example 30 | P3 | L3 | 2/1 | X | X | 28.3 | 4.2 | 4.5 | 9 |
| Comparative Example 31 | P3 | L4 | 2/1 | X | X | 32 | 4.3 | 4.7 | 11 |
| Comparative Example 32 | P4 | L3 | 2/1 | X | Δ | 50.5 | 5.2 | 5.9 | 55 |
| Comparative Example 33 | P4 | L4 | 2/1 | X | Δ | 53.2 | 5.3 | 5.9 | 58 |
| Comparative Example 34 | P5 | L6 | 2/1 | Δ | X | 43.8 | 4.4 | 5.2 | 10 |
| Comparative Example 35 | P9 | L5 | 2/1 | X | X | 39 | 5.1 | 5.8 | 40 |
| Comparative Example 36 | P10 | L5 | 2/1 | X | X | 45.3 | 4.8 | 5.5 | 41 |

TABLE 30

| | Element concentration (ppm) | | | | | |
|---|---|---|---|---|---|---|
| | F | B | Al | Si | Sr | Na |
| Example 73 | 0.7 | 2 | 0.8 | 1 | 2.8 | 0.6 |
| Example 74 | 0.7 | 2.1 | 0.9 | 1.3 | 2.6 | 0.8 |
| Example 75 | 3.6 | 6.2 | 2.8 | 3 | 7.8 | 1.9 |
| Example 76 | 3.8 | 6.5 | 3 | 2.8 | 7.9 | 2.1 |
| Example 77 | 2 | 3.9 | 2.5 | 2.3 | 4.4 | 1 |
| Example 78 | 1.7 | 3.6 | 2.2 | 2.1 | 4.8 | 1 |
| Example 79 | 1.8 | 3.8 | 2.3 | 2.3 | 4.6 | 1.1 |
| Example 80 | 2 | 4 | 2.5 | 2.1 | 4.8 | 1 |
| Example 81 | 4.2 | 4.1 | 2.3 | 2.5 | 4.4 | 3.3 |
| Comparative Example 30 | 0.3 | 0.8 | 0.4 | 0.3 | 0.9 | 0.2 |
| Comparative Example 31 | 0.4 | 0.8 | 0.5 | 0.5 | 1.1 | 0.3 |
| Comparative Example 32 | 4.3 | 6.8 | 3.3 | 3.1 | 8.1 | 2 |
| Comparative Example 33 | 4 | 6.8 | 3.5 | 3.3 | 8.2 | 2.3 |
| Comparative Example 34 | 0.3 | 1 | 0.5 | 0.2 | 0.2 | 0.1 |
| Comparative Example 35 | 1.6 | 3.5 | 1.9 | 2.4 | 4.3 | 1.2 |
| Comparative Example 36 | 1.5 | 3.3 | 1.8 | 2.3 | 4.1 | 1.1 |

Examples 73 to 81 are each the dental resin temporary sealing material composition including the noncrosslinked (meth)acrylate polymer, the ion sustained-release glass, the monofunctional (meth)acrylate polymerizable monomer, the hydrophilic polymerizable monomer, the polymerization initiator, and the plasticizer. As shown in Table 29, in the case where the formed cavity was temporarily sealed, pigment invasion was hardly observed, demonstrating excellent sealability. In addition, their proper hardness indicates excellent removability. Examples 77 and 78 respectively have the powder-liquid ratios of 2.2/1 and 1.8/1 assuming clinical fluctuations, but exhibited favorable sealability and removability as temporary sealing materials.

As shown in Table 30, Examples 73 to 81 released six types of ions including the fluoride ion. The fluoride ion is expected to strengthen the temporarily sealed cavity wall tooth substance. Moreover, in Examples 73 to 81, six types of ions were observed from the ion sustained-release glass to exhibit the acid neutralizing capacity. Therefore, not only the tooth substance strengthening effect by the fluoride ion but also the synergic effects with the other ions, such as tooth substance decalcification inhibition, can be expected. The foul breath suppression evaluation shows a reduction in VSC value by 30 or more, indicating that the dental resin temporary sealing material is effective in foul breath suppression.

Comparative Examples 30 to 33 exhibited poor removability, sealability, or Shore D hardness because each component is not in its preferable range. Comparative Example 34 is a system not including a hydrophilic polymerizable monomer, and exhibited poor sealability due to its low wettability with the tooth substance.

Comparative Examples 35 and 36 exhibited poor sealability and removability because the molecular weight and average particle diameter of PMMA or PEMA are not in their preferable ranges.

The invention claimed is:

1. A neutralization promoting ion sustained-release dental film consisting of:
    an ion sustained-release glass (a);
    a film forming material (e); and
    optionally one or more selected from the group consisting of a fluoride ion supply material, a saliva secretion promoter, a saliva buffering capacity improver, an antibacterial agent and a sweetener,
    wherein the ion sustained-release glass (a) is fluoroaluminoborosilicate glass having a composition range of:
    15% to 35% by mass $SiO_2$;
    15% to 30% by mass $Al_2O_3$;
    5% to 20% by mass $B_2O_3$;
    20% to 45% by mass SrO;
    5% to 15% by mass F; and
    0% to 10% by mass $Na_2O$;
    wherein the ion sustained-release glass (a) is surface-coated with a silane compound (c) to form a polysiloxane coating thereon, then surface treated with an acid polymer (d) by reacting the polysiloxane-coated ion sustained-release glass with the acid polymer (d), wherein an amount of the acid polymer (d) is 1% to 7% by weight relative to the weight of the polysiloxane-coated ion sustained-release glass, and thereafter mixed with the film forming material (e).

2. The neutralization promoting ion sustained-release dental film according to claim 1,
    wherein the ion sustained-release glass (a) sustained-releases a fluoride ion, and further sustained-releases at least one ion selected from the group consisting of a strontium ion, an aluminum ion, and a borate ion.

3. The neutralization promoting ion sustained-release dental film according to claim 1,
    wherein the neutralization promoting ion sustained-release dental film has a thickness of 15 μm to 500 μm.

4. The neutralization promoting ion sustained-release dental film according to claim 1,
    wherein a content of the ion sustained-release glass (a) is in a range of 1% to 35% by weight with respect to the neutralization promoting ion sustained-release dental film.

5. The neutralization promoting ion sustained-release dental film according to claim 1,
    wherein the film forming material (e) is one or more selected from the group consisting of polyvinylpyrrolidone, polyvinylalcohol, polyethyleneglycol, sodium polyacrylate, carboxymethylcellulose, hydroxypropylcellulose, ethylcellulose, hydroxyethylcellulose, hydroxypropylmethylcellulose, hydroxypropylmethylcellulose phthalate, cellulose acetate phthalate, carboxymethylethylcellulose, carboxymethylcellolose potassium, carboxymethylcellulose sodium, carboxymethylcellulose calcium, starch, xanthan gum, karaya gum, alginate sodium, methylcellulose, carboxyvinyl polymer, agar, amylose, pullulan, chitosan, starch, rosin, sodium carboxymethyl starch, plantago testa, galactomannan, Eudragit, casein, alginate alkyl ester, gelatin, hydroxyethylmethyl cellulose, ethyl methacrylate/chloridized trimethylammonium ethyl methacrylate copolymer, dimethylaminoethyl methacrylate/methyl methacrylate copolymer, pullulan, and acrylic acid/methyl methacrylate copolymer.

6. The neutralization promoting ion sustained-release dental film according to claim 1, wherein a blending quantity of the film forming material (e) is 60% to 90% by weight.

7. The neutralization promoting ion sustained-release dental film according to claim 1,
    wherein the fluoride ion supply material is a fluoride salt and/or a plant-derived fluorine compound.

8. The neutralization promoting ion sustained-release dental film according to claim 7,
    wherein the fluoride salt is one or more selected from the group consisting of lithium fluoride, sodium fluoride, potassium fluoride, rubidium fluoride, cesium fluoride, beryllium fluoride, magnesium fluoride, calcium fluoride, strontium fluoride, barium fluoride, aluminum fluoride, manganese(II) fluoride, iron(II) fluoride, iron (III) fluoride, silver(I) fluoride, diammine silver fluoride, sodium hydrogenfluoride, potassium hydrogenfluoride, sodium fluorophosphates, potassium hexafluorotitanate, sodium hexafluorosilicate, sodium hexafluorophosphate, pentafluoro-2-sodium stannate (II), and potassium hexafluorozirconate.

9. The neutralization promoting ion sustained-release dental film according to claim 1,
    wherein a blending quantity of the fluoride ion supply material is 0.1% to 10% by weight.

10. The neutralization promoting ion sustained-release dental film according to claim 1,
    wherein the saliva secretion promoter is one or more organic acid selected from the group consisting of citric acid, tartaric acid, fumaric acid, malic acid, succinic acid, and lactic acid.

11. The neutralization promoting ion sustained-release dental film according to claim 1,
    wherein a blending quantity of the saliva secretion promoter is 0.05% to 1% by weight.

12. The neutralization promoting ion sustained-release dental film according to claim 1,
    wherein the saliva buffering capacity improver is one or more selected from the group consisting of sodium hydrogencarbonate, disodium hydrogenphosphate, calcium hydrogenphosphate, tricalcium phosphate, sodium carbonate, and a basic amino acid.

13. The neutralization promoting ion sustained-release dental film according to claim 1,
wherein a blending quantity of the saliva buffering capacity improver is 5% to 20% by weight.

14. The neutralization promoting ion sustained-release dental film according to claim 1,
wherein the antibacterial agent is one or more selected from the group consisting of a cationic antibacterial agent and a nonionic antibacterial agent,
wherein the cationic antibacterial agent is one or more selected from the group consisting of chlorhexidine, cetylpyridinium chloride, benzethonium chloride, benzalkonium chloride, and dequalinium chloride, and
wherein the nonionic antibacterial agent is one or more selected from the group consisting of isopropylmethylphenol and halogenated diphenyl ether.

15. The neutralization promoting ion sustained-release dental film according to claim 1,
wherein the sweetener is one or more selected from the group consisting of xylitol, maltitol, aspartame, sorbitol, saccharin sodium, sucralose, reduced palatinose, palatinose, mannitol, erythritol, and cyclodextrin.

16. The neutralization promoting ion sustained-release dental film according to claim 1,
wherein an area of the neutralization promoting ion sustained-release dental film is 0.5 $cm^2$ to 25 $cm^2$.

17. The neutralization promoting ion sustained-release dental film according to claim 1, having a multilayer structure.

* * * * *